United States Patent [19]

Earl et al.

[11] Patent Number: 5,300,642
[45] Date of Patent: Apr. 5, 1994

[54] α, α-DISUBSTITUTED AROMATICS AND HETEROAROMATICS AS COGNITION ENHANCERS

[75] Inventors: Richard A. Earl; Melvyn J. Myers, both of Wilmington, Del.; Victor J. Nickolson, Hermelijnedreef, Netherlands

[73] Assignee: The Du Pont Merck Pharmaceutical Company, Wilmington, Del.

[21] Appl. No.: 953,274

[22] Filed: Sep. 30, 1992

Related U.S. Application Data

[60] Division of Ser. No. 234,382, Aug. 23, 1988, Pat. No. 5,173,489, which is a continuation-in-part of Ser. No. 105,156, Oct. 6, 1987, abandoned, which is a continuation-in-part of Ser. No. 944,953, Jan. 5, 1987, Pat. No. 4,760,083, which is a continuation-in-part of Ser. No. 850,015, Apr. 10, 1986, abandoned.

[51] Int. Cl.$^5$ ............... C07D 401/08; C07D 403/08
[52] U.S. Cl. .................... 544/238; 540/522; 544/294; 544/296; 544/319; 544/331; 544/333; 544/357; 544/405; 544/336; 546/256; 546/268; 546/269; 546/270; 546/271; 546/272; 546/274; 546/285
[58] Field of Search ............ 544/238, 294, 357, 405, 544/296, 333, 331, 319; 546/255, 256, 268, 279, 283, 284, 269, 270, 271, 272, 274, 285; 540/522

[56] References Cited

U.S. PATENT DOCUMENTS

| 3,574,232 | 4/1971 | Canas-Rodriguez et al. | 260/326.11 |
| 4,760,083 | 7/1988 | Myers et al. | 514/333 |
| 5,173,489 | 12/1992 | Earl et al. | 514/252 |

FOREIGN PATENT DOCUMENTS

| 0005143 | 11/1979 | European Pat. Off. |
| 147805 | 12/1983 | European Pat. Off. |
| 3405332 | 2/1984 | Fed. Rep. of Germany |
| 49-085073 | 12/1972 | Japan |
| 54-125662 | 3/1978 | Japan |
| 56-073073 | 11/1979 | Japan |
| 56-077263 | 11/1979 | Japan |
| 55-129284 | 10/1980 | Japan |
| 59-98896 | 6/1984 | Japan |
| 61-282348 | 6/1985 | Japan |
| 443344 | 12/1964 | Switzerland |
| 656378 | 5/1983 | Switzerland |
| 897052 | 3/1959 | United Kingdom |
| 936782 | 3/1959 | United Kingdom |
| 936783 | 3/1959 | United Kingdom |

OTHER PUBLICATIONS

Research Disclosures, 184, pp. 446–454 (1979); Adin et al.
J. Heterocyclic Chem., 19, pp. 1013–1016 (1982); Daisley et al.
Eur. J. Med. Chem.—Chem. Ther. 16(4), pp. 373–378 (1981); Ogata et al.

*Primary Examiner*—Joseph Paul Brust
*Attorney, Agent, or Firm*—Gerald J. Boudreaux

[57] ABSTRACT

Cognitive defeciencies or neurological dysfunction in mammals are treated with α,α-disubstituted aromatic or heteroaromatic compounds. The compounds have the formula:

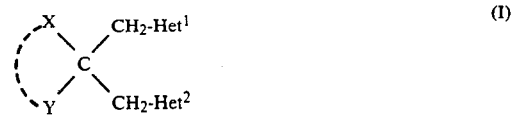

or a salt thereof
wherein X and Y are taken together to form a saturated or unsaturated carbocyclic or heterocyclic first ring and the shown carbon in said ring is α to at least one additional aromatic ring or heteroaromatic ring fused to the first ring;
one of Het$^1$ or Het$^2$ is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.

1 Claim, No Drawings

α, α-DISUBSTITUTED AROMATICS AND HETEROAROMATICS AS COGNITION ENHANCERS

This is a division of application Ser. No. 07/234,382, Aug. 23, 1988, U.S. Pat. No. 5,173,489, which is continuation-in-part of Ser. No. 105,156, Oct. 6, 1987, abandoned, which is a continuation-in-part of Ser. No. 06/944,953, Jan. 5, 1987, U.S. Pat. No. 4,760,083, which is a continuation-in-part of Ser. No. 850,015, Apr. 10, 1986, abandoned.

BACKGROUND OF THE INVENTION

1. Field Of Invention

This invention relates to α,α-disubstituted aromatic and heteroaromatic compounds, to pharmaceutical compositions containing them, processes for preparing them, and methods of using them in mammals to treat cognitive deficiencies and/or neurological dysfunction and/or mood disturbances such as found, for example, in degenerative nervous system diseases.

2. Background Including Prior Art

There is a steadily growing need for effective treatment for Nervous System Disorders causing cognitive and neurological deficiencies. Many of these diseases, of which the incidence generally rises with increasing age, are due to degenerative changes in the nervous system. Although in early stages of some diseases certain systems are rather specifically affected (e.g., cholinergic systems in Alzheimer's Disease, and Myasthenia Gravis, the dopaminergic system in Parkinson's Disease, etc.), multiple neurotransmitter system deficiencies (acetylcholine, dopamine, norepinephrine, serotonin) are generally found at later stages of diseases such as senile dementia, multi-infarct dementia, Huntington's disease, mental retardation, etc. This may explain the generally observed multiple symptomatology which includes cognitive, neurological and affective/psychotic components (see Gottfries, *Psychopharmacol.* 86, 245, 1985). Deficits in the synthesis and release of acetylcholine in the brain are generally thought to be related to cognitive impairment (see Francis et. al., *New England J. Med.*, 313, 7, 1985) whereas neurological deficits (e.g., Parkinsonian symptoms) and mood/mental changes may be related to impairment of dopaminergic and serotonergic systems, respectively. Other neurological deficits (e.g., Myasthenia Gravis) are related to cholinergic deficiencies in the peripheral nervous system.

Treatment strategies employed hitherto encompass vasoactive drugs like vincamine and pentoxifylline; "metabolic enhancers" like ergoloid mesylates, piracetam and naftidrofuryl; neurotransmitter precursors like 1-DOPA, choline and 5-hydroxytryptamine; transmitter metabolizing enzyme inhibitors like physostigmine; and neuropeptides like adrenocorticotropic hormone and vasopressin-related peptides. Except for 1-DOPA treatment in Parkinson's disease and cholinesterase inhibitor treatment in Myasthenia Gravis, these treatment strategies have generally failed to produce clinically significant improvements (Hollister, *Drugs*, 29, 483, 1985). Another strategy to treat these multiple symptoms is to enhance the residual function of the affected systems by enhancing the stimulus-induced release of neurotransmitters. Theoretically, such an enhancement would improve the signal-to-noise ratio during chemical transmission of information, thereby reducing deficits in processes related to cognition, neurological function and mood regulation.

To date, there are not many patent or literature references which describe 3,3-heterocyclic disubstituted indolines. Most pertinent are Japanese Patent 55-129284, issued Oct. 6, 1980 and M. Ogata et. al., *Eur. J. Med. Chem-Chim. Ther.*, 16(4), 373-378 (1981), which describe antifungal compounds having the formula:

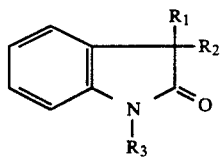

wherein
R is H, halogen, alkyl, or alkoxy;
$R^1$ is H, alkyl, aryl or acyl; and
$R^2$ is thienyl, or imidazole, amongst non-heterocyclic groups.

R. W. Daisley, et. al., *J. Heterocyclic Chem.*, 19, 1913-1916, (1982), report 1-methyl-3,3-dipiperidinoindol-2-(3H)-one as product from the reaction of the corresponding (Z) or (E) 1-arylmethylidene-indol-3(2H)-one with ethyl cyanoacetate in the presence of excess piperidine. No utility for the compound is described.

Japanese Patent 59-98896 describes high sensitivity, high stability recording medium containing a 3,3-disubstituted-2-oxo-2,3-dihydroindole derivative of the formula shown below as a near infrared absorber.

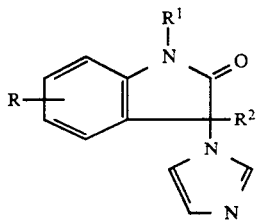

wherein
$R_1$, $R_2$, same or different, are a saturated heterocyclic ring including morpholino, pyrrolidinyl, amongst others containing at least one nitrogen atom; and
$R_3$ is H or alkyl.

3,3-bis(morpholino)oxoindole is also disclosed in U.S. Pat. No. 4,273,860, to A. Adin, Jun. 16, 1981 and in A. Adin, et. al., *Research Disclosures*, 184, 446-454 (1979), as a destabilizer material in a photoinhibitor composition utilizing cobalt (III) complexes.

The above references, other than J55-129184, and M. Ogata et. al., *Eur. J. Med. Chem-Chim, Ther.*, 16(4), 373-378 (1981) all describe 3,3-disubstituted indolines wherein the heterocyclic groups are both saturated rings. In all of the above references, the heterocyclic ring is attached to the indoline by a ring nitrogen. Furthermore, in the references other than J55-129284, there is no suggestion of pharmaceutical utility for these 3,3-disubstituted indolines.

SUMMARY OF THE INVENTION

It has now been found that certain aromatic and heteroaromatic compounds having a broad ring core structure and pendant α,α-disubstituted heterocyclic groups enhance the stimulus-induced release of neurotransmitters, specifically acetylcholine and, in addition, dopamine and serotonin in nervous tissue and improve processes involved in learning and memorization of an active avoidance task.

More particularly, according to the present invention there is provided a pharmaceutical composition consisting essentially of a pharmaceutically suitable carrier and an effective amount of a compound of the formula

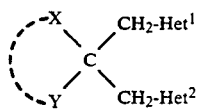

or a salt therof
wherein X and Y are taken together to form a saturated or unsaturated carbocyclic or heterocyclic first ring and the shown carbon in said ring is α to at least one additional aromatic ring or heteroaromatic ring fused to the first ring;
one of $Het^1$ or $Het^2$ is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.

Additionally provided is a method for the treatment of a neurological disorder in a mammal which comprises: administering to the mammal a therapeutically effective amount of a compound of Formula (I).

Further provided are particular novel classes of compounds within Formula (I) which are active in treating a neurological disorder in a mammal. These compounds are as follows:

(1) A compound having the formula:

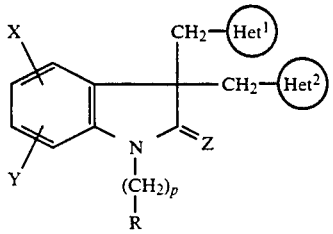

wherein:
p is 0 or 1;
Z is O or S;
R is $C_1-C_{10}$ alkyl, $C_3-C_8$ cycloalkyl, 2-pyridyl, 3-pyridyl, 4-pyridyl, or

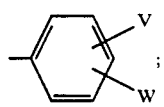

V, W, X, and Y independently are H, halo, $C_1-C_3$ alkyl, $OR^1$, $NO_2$, $CF_3$, CN or $NR^1R^2$;
$R^1$ and $R^2$ independently are H or $C_1-C_3$ alkyl;
$Het^1$ and $Het^2$ independently are 6-membered heterocyclic aromatic rings containing one or two nitrogen atoms as part of the ring optionally substituted with one substituent selected from the group $C_1-C_3$ alkyl, halo, $OR^1$ or $NR^1R^2$; or
an N-oxide or pharmaceutically suitable acid addition salt thereof.

(2) A compound having the formula:

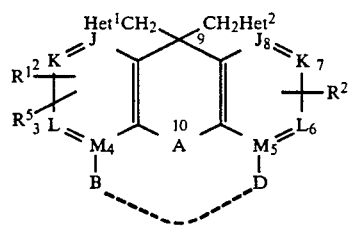

or a salt thereof
wherein each J, K, L and M independently are N, $CR^1$, $CR^5$ or $CR^2$ with the proviso that when either $M_4$, $M_5$ or both is N, then B, D or both cannot be $R^1$ or $R^2$;

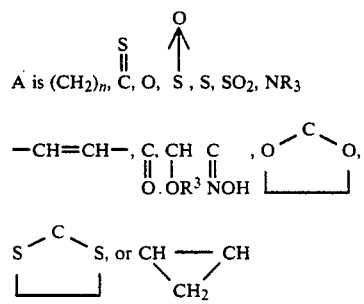

n is 0, 1, 2 or 3;
$R^1$ and $R^2$ independently are H, halo, alkyl of 1-3 carbon atoms, acyl, $OR^3$, $NO_2$, CN, $NR^3R^4$, or fluoroalkyl of 1-3 carbon atoms;
$R^3$ and $R^4$ independently are H, alkyl of 1-3 carbon atoms, or acyl;
B and D independently are $R^1$ or $R^2$ or, when A is $(CH_2)_o$ can be taken together to form —CH=CH—, or —$CH_2$—$CH_2$—;
$R^5$ independently is H, or is taken together with $R^1$ to form a 2,3- or a 3,4-fused benzo ring;
one of $Het^1$ or $Het^2$ is 2, 3, or 4-pyridyl or 2, 4 or 5-pyrimidinyl and the other is selected from:
(a) 2, 3 or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.

(3) A compound having the formula:

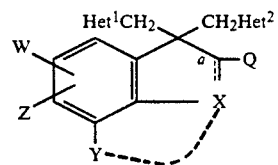

or a salt thereof
wherein a is a single bond or double bond; X independently when a is a single bond is O, S, $CR^1R^2$, CQ, $C(R^1)OR^3$, or —($CH_2$—)$_n$ where n is 1, 2 or 3;

X independently when a is a double bond is CR$^2$ or COR$^3$;

X and Y taken together when a is a single bond is

X and Y taken together when a is a double bond is

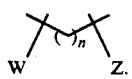

where n is 1 or 2;

Q when a is a single bond is =O, =S, H$_2$, OR$^3$, =NOR$^1$,

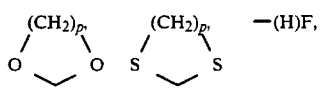

F$_2$, (R$^1$)OR$^3$, =CR$^1$R$^2$;

Q when a is a double bond is R$^2$, OR$^3$ or halo;

p is 2 or 3;

R$^1$ is H, alkyl of 1-10 carbon atoms, cycloalkyl of 3-8 carbon atoms, or

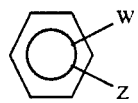

R$^2$ is R$^1$, NO$_2$, CN, CO$_2$R$^1$,

or halo;

R$^3$ is R$^1$ or

W, Y, Z independently are H, halo, alkyl of 1-3 carbon atoms, OR$^3$, NO$_2$, CF$_3$, fluoroalkyl, CN, or N(R$^1$)$_2$; and Het$^1$ and Het$^2$ are as defined in (2) above.

(4) A compound having the formula:

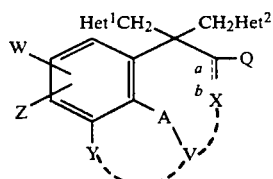

or a salt thereof
wherein a is a single bond or double bond;

b is a single bond or double bond, provided one of a or b is a single bond;

X independently when a and b are single bonds is O, S, CR$^1$R$^2$, CQ, C(R$^1$)OR$^3$, or —(—CH$_2$—)—$_n$ where n is 1, 2 or 3, N(CH$_2$)$_p$R$^3$ where p is O or 1, or NCOR$^1$;

X independently when one of a or b is a double bond is CR$^2$, COR$^3$, or N;

V independently when b is a single bond is CQ;

V independently when b is a double bond is CR$^2$ or COR$^3$;

A is a single bond, —(—CR$_2^1$—)$_n$—, —X—, —(—CR$_2^1$—)$_n$—X, where n is 1, 2 or 3 and X is as defined above when a is a single bond;

Y and V taken together when A and b are single bond is

Y and V taken together when A is a single bond is —CH$_2$—(—CH$_2$—)$_m$—CH$_2$— where m is 1 or 2;

provided that when Y and V are connected, then V and X are not connected;

V and X taken together when b is a double bond is C—CH=CH—CH=CH—C—, or —C—(—CH$_2$—)$_p$—C;

provided that when V and X are connected, then Y and V are not connected;

Q when a is a single bond is =O, =S, H$_2$, OR$^3$, =NOR$^1$,

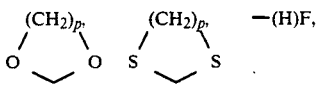

F$_2$, (R$^1$)OR$^3$, =CR$^1$R$^2$;

Q when a is a double bond is R$^2$, OR$^3$ or halo;

p is 2 or 3;

R$^1$ is H, alkyl of 1-10 carbon atoms, cycloalkyl of 3-8 carbon atoms, or

R$^2$ is R$^1$, NO$_2$, CN, CO$_2$R$^1$,

or halo;

R$^3$ is R$^1$ or

W, Y, Z each independently is H, halo, alkyl of 1-3 carbon atoms, OR$^3$, NO$_2$, CF$_3$, CN, or N(R$^1$)$_2$; and Het$^1$ and Het$^2$ are as defined in (2) above.

PREFERRED EMBODIMENTS

Preferred Het$^1$ and Het$^2$ in a compound of Formula (I) is where one is 2, 3 or 4-pyridyl or 2, 4, or 5-pyrimidinyl and the other is 2, 3, or 4-pyridinyl, 2, 4, or 5-pyrimidinyl, or 2, or 3-tetrahydrofuranyl.

Het¹ and Het² are most preferably selected from:
(a) 4-pyridinyl and 4-pyridinyl,
(b) 4-pyrimidinyl and 4-pyrimidinyl,
(c) 4-pyridinyl and 4-pyrimidinyl,
(d) 4-pyridinyl and 3-tetrahydrofuranyl.

Preferred compounds of Formula (4) are those where:
p is o; or
Z is O; or
X and Y are H; or
R is $CH_3$, phenyl or m-chlorophenyl; or
Het¹ and Het² are each pyridyl attached by a ring carbon atom.

Specifically preferred compounds of Formula (4) are:
3,3-Bis(2-pyridylmethyl)-1-phenylindolin-2-one;
3,3-Bis(3-pyridylmethyl)-1-phenylindolin-2-one;
3,3-Bis(4-pyridylmethyl)-1-phenylindolin-2-one;
3,3-Bis(4-pyridylmethyl)-1-methylindolin-2-one;
3,3-Bis(4-pyridylmethyl)-1-(3-chlorophenyl)-indolin-2-one;
and pharmaceutically suitable acid addition salts thereof.

Preferred compounds of Formula (II) are:
(a) those compounds of Formula (II) where:
A is a bond, i.e., is $(CH_2)_n$ where n is 0; B and D are $R^1$ and $R^2$; 0 to 2 of J, $K_2$, $L_3$ and $M_4$ are N and the remainder are $CR^1$ or $CR^5$; and 0 to 2 of $J_8$, $K_7$, $L_6$ and $M_5$ are N and the remainder are $CR^2$, with the proviso that when either $M_4$, $M_5$ or both is N, then B, D or both cannot be $R^1$ or $R^2$; or
$R^1$ and $R^5$ are H; or
$R^2$ is H, halo, alkyl or 1-3 carbon atoms, $OR^3$, $NH_2$, or fluoroalkyl of 1-3 carbon atoms; or
Het¹ and Het² are as preferred for compounds of Formula (I).
Specifically preferred compounds of Formula (II) (a) are:
5,5-Bis(4-pyridinylmethyl)cyclopenta[2,1-b:3,4-b']dipyridine;
9,9-Bis(4-pyridinylmethyl)indeno-[1,2-b]pyridine;
5,5-Bis(4-pyridinylmethyl)cyclopenta[2,1-c:3,4-c']dipyridine;
9,9-Bis(4-pyridinylmethyl)cyclopenta[1,2-c:4,3-c']dipyridine;
9,9-Bis(4-pyridinylmethyl)cyclopenta[1,2-b:3,4-b']dipyridine.
(b) those of Formula (II) where:
B and D are both H; and J, K, L and M are carbon atoms; or
A is $(CH_2)_n$ where n is 0-3, $$\overset{O}{\underset{}{\overset{\|}{C}}},$$

CHOH, C=NOH, O, S, $NR^3$,

or $SO_2$; or
$R^1$ and $R^5$ are H; or
$R^2$ is H, halo, alkyl of 1-3 carbon atoms, $OR^3$, $NH_2$, or fluoroalkyl of 1-3 carbon atoms; or
Het¹ and Het² are as preferred for compounds of Formula (I).

Specifically preferred compounds of Formula (II)(b) are:
9,9-bis(4-pyridylmethyl)anthrone dihydrochloride;
9,9-bis(4-pyridylmethyl)fluorene dihydrochloride;
9,9-bis(4-pyridylmethyl)xanthene;
9,9-bis(4-pyridylmethyl)anthrone dihydrochloride;
(c) those of Formula (II) where:
A is a bond, i.e., is $(CH_2)_n$ where n is 0; and J, K, L and M are carbon atoms; or
B and D are taken together to form —CH=CH— or —$CH_2$—$CH_2$—
$R^1$ and $R^5$ are H; or
$R^2$ is H, halo, alkyl of 1-3 carbon atoms, $OR^3$, $NH_2$, or fluoroalkyl of 1-3 carbon atoms; or
Het¹ and Het² are as preferred for compounds of Formula (I).

Specifically preferred compounds of Formula (II)(c) are:
9,9-bis(4-pyridinylmethyl)cyclopenta[def]phenanthrene;
9,9-bis(4-pyridinylmethyl)-4,5-dihydrocyclopenta[def]phenanthrene.

Preferred compounds of Formula (III) are:
(a) those of Formula (III) where:
a is a single bond; and
X independently is O, $CR^1R^2$, or $C(R^1)OR^3$;
W, Y and Z independently are H or $OCH_3$; or
Q is =O, =S, $H_2$, $OR^3$, =$CR^1R^2$, or $C(R^1)OR^3$; or
Het¹ and Het² are as preferred for compounds of Formula (I).
Specifically preferred compounds of Formula (III)(a) where a is a single bond are:
4-((2,3-dihydro-3-phenyl-1-(4-pyridinylmethyl)-1H-inden-1-ylmethyl))-pyridine dihydrochloride;
1,1-bis(4-pyridinylmethyl)-1,3-dihydro-2H-inden-2-one;
3,3-bis(4-pyridinylmethyl)-2,3-dihydro-1-phenyl-1H-indene-1,2-diodiacetate dihydrochloride;
3,3-bis(4-pyridinylmethyl)-2(3H)-benzofuranone dihydrochloride.
(b) those of Formula (III) where:
a is a double bond; and
X independently is $CR^2$; or
W, Y and Z independently are H or $CH_3$; or
Q is $R^2$; or
Het¹ and Het² are as preferred for compounds of Formula (I).
A specifically preferred compound of Formula (III)(b) where a is a double bond is: 1,1-bis(4-pyridinylmethyl)-3-phenyl-1H-indene-bismethanesulfonate.
(c) those of Formula (III) where:
a is a single bond; and
X and Y are taken together; and
Q is =O, =S, $H_2$, =$CR^1R^2$, or $C(R^1)OR^3$; or
W and Z are each H or $OCH_3$; or
Het¹ and Het² are as preferred for compounds of Formula (I).
Specifically preferred compounds of Formula (III)(c) are:
2,2-bis(4-pyridinylmethyl)-1(2H)acenaphthylenone dihydrochloride;
4-((1,2-dihydro-2-methylene-1-(4-pyridinylmethyl)-1-acenaphthylene-1-ylmethyl)) pyridine dihydrochloride.

Preferred compounds of Formula (IV) are:
(a) those of Formula (IV) where:
A is a single bond, and X and Y are taken independently; and
a and b are single bonds; or Q is =O, =S, =CR$^1$R$^2$, H$_2$ or C(R$^1$)OR$^3$; or
X is CR$^1$R$^2$, O, or NR$_3$; or
V is —CH$_2$—, CQ, or CR$^1$; or
W, Y and Z each is H or OCH$_3$; or
Het$^1$ and Het$^2$ are as preferred for compounds of Formula (I); or
R$^1$ is H, CH$_3$ or phenyl; or
R$^2$ is H; or
R$^3$ is H or $$\overset{CR^1}{\underset{O}{\|}}$$

Specifically preferred compounds of Formula (IV)(a) where a and b are single bonds are:
1,1-bis(4-pyridinylmethyl)-2-(1H)-naphthalenone;
4,4-bis(4-pyridinylmethyl)-2-phenyl-1,3(2H, 4H)-isoquinolinedione.
(b) those of Formula (IV) where:
A is a single bond, and X and Y are taken independently; and
a is a single bond and b is a double bond; or
Q is H$_2$ or =O; or
X is N or CR$^2$; or
V is CR$^2$; or
W, Y and Z each is H or OCH$_3$; or
Het$^1$ and Het$^2$ are as preferred for compounds of Formula (I); or
R$^2$ is H or phenyl.
A specifically preferred compound of Formula (IV)(b) where a is a single bond and b is a double bond is: 4,4-bis(4-pyridinylmethyl)-3,4-dihydro-6,7-dimethoxy-1-phenyl isoquinoline.
(c) those of Formula (IV) where:
A is a single bond, and Y and V are taken together, and b is a single bond; and
a is a single bond; or
Q is =O, =S, =CR$^1$R$^2$, or C(R$^1$)OR$^3$; or
X is CR$^1$R$^2$, O, or NR$^3$;
W and Z each is H or OCH$_3$; or
Het$^1$ and Het$^2$ are as preferred for compounds of Formula (I); or $$\overset{CR^1}{\underset{O}{\|}},$$

or phenyl.
A specifically preferred compound of Formula (IV)(c) where a is a single bond is: 3,3-bis(4-pyridinylmethyl)-naphtho[1,8-b,c]pyran-2-one.
(d) those of Formula (IV) where:
V and X are taken together, and a is a single bond, and b is a double bond; and
A is (CH$_2$)$_n$, (CH$_2$)$_n$—X where X is O, S, SO$_2$, $$\overset{O}{\underset{S}{\overset{\uparrow}{\|}}},$$

or NH$^3$ where R$^3$ is H, alkyl of 1–3 carbon atoms or acyl, and n is 0, 1 or 2; or
Q is =O, =S, =CR$^1$R$^2$, or C(R$^1$)OR$^3$; or
W, Y and Z each is H or OCH$_3$; or
Het$^1$ and Het$^2$ are as preferred for compounds of Formula (I); or
R$^1$ is H, CH$_3$ or phenyl; or
R$^2$ is H; or
R$^3$ is H or $$\overset{O}{\underset{CR^1}{\|}}.$$

A specifically preferred compound of Formula (IV)(d) is: 11,11-bis(4-pyridinylmethyl)-5H-dibenzo[a,d]cyclohepten-10(11H)-one dihydrochloride.

DETAILED DESCRIPTION OF THE INVENTION

Synthesis

Most of the oxindole compounds of this invention are prepared by the synthetic sequence represented by Scheme 1.

Scheme 1

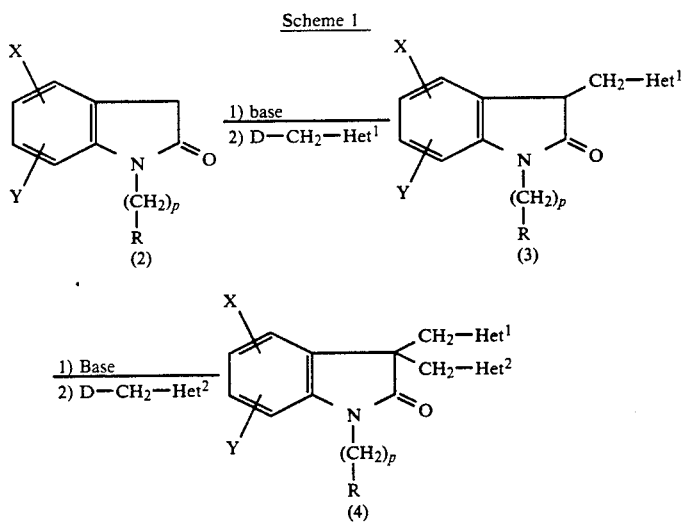

R$^1$ is H, CH$_3$ or phenyl; or
R$^2$ is H; or
R$^3$ is H,

X, Y, p, R, —Het$^1$, and —Het$^2$ are as defined above, D represents a displaceable group such as halogen (I, Br, Cl, or F) or methanesulfonate or p-toluenesulfonate.

These reactions result from formation of an anion at the 3-position of the oxindole of Formula (2) by reaction of the oxindole with a suitable base followed by displacement of D by the anion and formation of the 3-mono-substituted compound (3). This mono-substituted product (3) can then either be isolated prior to the next step or, preferably, especially when —Het$^1$ and —Het$^2$ are the same, treated again with another equivalent of base without prior isolation, to give the 3,3-disubstituted oxindole (4).

Suitable bases for forming the anion include sodamide, lithium diisopropylamide, sodium hydride, potassium tert-butoxide, sodium alkoxide, potassium alkoxide, lithium alkoxide, potassium hydride, lithium 2,2,6,6-tetramethylpiperidide, butyl lithium, sec-butyl lithium, tert-butyl lithium, and lithium, sodium or potassium hexamethyldisilazide. The reaction is run in an aprotic solvent, generally in an ether such as diethylether, glyme, tetrahydrofuran or dioxane. However, if the oxindole is soluble in a nonpolar solvent, the reaction may be run in a hydrocarbon such as hexane, heptane, cyclohexane, methylcyclohexane, benzene or toluene.

In running the reaction, the oxindole is dissolved in an appropriate solvent, and, depending upon the strength of the base, the solution is cooled to a temperature between −40° C. and room temperature. When a more reactive base such as lithium diisopropylamide (LDA) is used, the solution is cooled to a temperature of −30° C. and a solution of the LDA in an appropriate solvent, such as tetrahydrofuran, is added dropwise over a period of 15 minutes to one hour, while maintaining the temperature at approximately −30° C.

If one chooses to use sodamide instead of LDA, benzene is the preferred solvent. The sodamide is added to a solution of the indolinone in benzene at room temperature. In order to drive the reaction to completion, the solution is refluxed until ammonia can no longer be detected evolving from the reaction.

A solution of the electrophile D—CH$_2$—Het$^1$ is then added to the indolinone anion. Again, if a very reactive base such as LDA is used to generate the anion, the reaction is cooled to −30° C. and the electrophile is added dropwise. If a less active base is used to generate the anion, the electrophile is added at a temperature between 0° C. and room temperature and then the reaction mixture is refluxed.

The bisubstituted product (4) can be prepared by generation of a second anion at the three position of the indolinone. The anion formation followed by alkylation can be done in the same manner as described above for the preparation of a mono-substituted compound of Formula (3).

Instead of running the reaction sequentially, one may at times, add two equivalents of base to the indolinone, followed by two to three equivalents of the alkylating agent. In some cases, especially those where —Het$^1$ is the same as —Het$^2$, it may be convenient to accomplish alkylation of the oxindole under phase transfer conditions, e.g., using a base such as sodium hydroxide dissolved in water, a water immiscible solvent such as benzene or toluene, a phase transfer catalyst such as benzyltriethylammonium chloride and two molar equivalents of the alkylating agent D—CH$_2$—Het$^1$. Under such conditions, vigorous stirring and elevated reaction temperatures, e.g., 60°–80° C., may facilitate conversion to the 3,3-dialkylated oxindole.

When the reaction is complete as evidenced by thin layer chromatography, excess anion is decomposed with saturated ammonium chloride solution, and the reaction is taken through an acid-base cycle to remove neutral starting materials. Purification of the basic product generally involves conventional purification techniques such as flash chromatography followed by recrystallization if necessary. The pure base (one spot on thin layer chromatography and analytical HPLC) is converted to the dihydrochloride by adding a slight excess of 25% hydrochloric acid in a solvent such as ethanol. Generally, adding an equal volume of acetone to the boiling solution affords a crop of pure colorless crystals upon cooling. Other methods that will be obvious to one skilled in the art can be used to obtain a crystalline product. The hydrochloride salt can be recrystallized from isopropanol, 1-propanol, ethanol, 95% ethanol, methanol, or mixtures of an alcohol with acetone, ethyl acetate, isopropyl acetate, or acetonitrile.

The hydrochloride salt can be converted to the corresponding free base by treatment with an inorganic base, e.g., sodium hydroxide, potassium hydroxide, sodium phosphate, ammonium hydroxide, or potassium carbonate, and then can be taken up in an organic solvent such as methylene chloride, ether, or ethyl acetate, and reprecipitated as a salt with some other pharmacologically acceptable acid such as maleic acid, methanesulfonic acid, napthalene-2-sulfonic acid, tartaric acid, hydrogen bromide, etc.

Alternatively, thallium (I) ethoxide can be used as the base as illustrated by Scheme 2. The indolinone is dissolved in a suitable solvent, preferably warm benzene, and an equimolar quantity of thallium (I) ethoxide is added rapidly to it. The organothallium compound (5) which precipitates out as a poisonous, yellowish, crystalline stable solid, is filtered affording the thallium compound in yields of 85–95%. Care must be exercised in handling thallium compounds because of their toxicity.

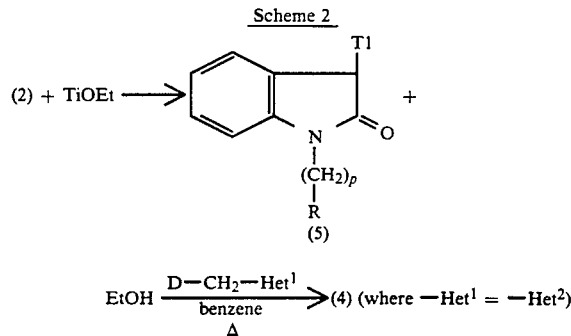

Organothallium compounds generally react with electrophiles to form the monoalkylated products. However, with very reactive electrophiles such as picolyl chlorides, benzyl bromide or the like, the 3,3-bis-alkylated products are obtained, as shown in Scheme 2, and as is exemplified by Example 1.

The thallium indoline (5) is heated with an electrophile such as picolyl chloride in an inert solvent, such as benzene or toluene, at 30° C. to the boiling point of the solvent, for several hours to 24 hours. Preferred is a temperature of 80° C. for 24 hours. When the reaction is complete as indicated by thin layer chromatography and the precipitated thallium chloride is filtered off, the remaining organic solution is taken through an acid-base cycle and purification, and optional salt formation is carried out as described above.

Preparation of the starting oxindole (2) represented in Scheme 1 and Scheme 2 can be carried out by one or more of a large number of general synthetic methods described in the chemical literature. For instance the reaction of an N-substituted anile (6) with chloroacetyl chloride to form an amide (7) is a well known reaction. This is illustrated in Scheme 3.

Scheme 3

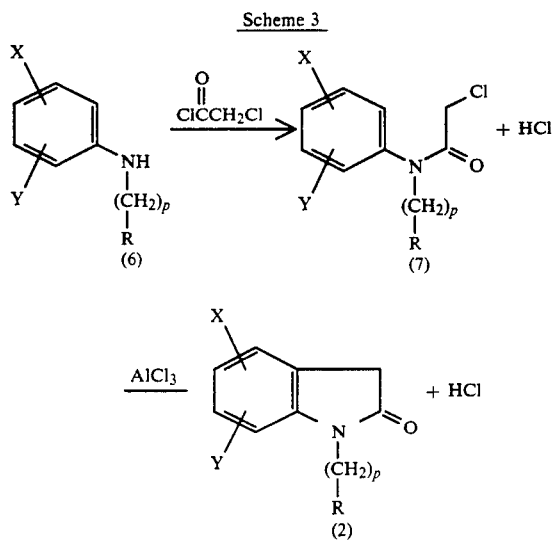

Requisite diarylamine syntheses (6; where p=0, R=substituted phenyl) are widely known in the chemical literature. Many involve conversion of N-arylphenyl-enediamine by diazotization and for example Sandmeyer reaction with the appropriate substituted diarylamine. Again, one skilled in the art of organic synthesis can select a suitable synthesis for preparation of the appropriate diarylamine required to extend the Examples to the related compound of this invention. Recent useful syntheses include those described by Katritzsky et al., *J. Chem Soc., Perkin. Trans. I*, 2611 (1983), Gorwin et al., *Chem. Commun.*, 4, 238 (1985), and Malz et al. in U.S. Pat. No. 4,431,841A (1984).

Other N-substituted anilines (6; where p=1) can be made by conventional synthetic methods commonly used in organic chemistry, e.g., by reaction of a suitable carboxylic acid chloride with an aniline to afford an amide which is then reduced by lithium aluminum hydride or diborane in tetrahydrofuran at about 67° C. to afford the N-substituted aniline (6), as depicted in Scheme 4 below.

Scheme 4

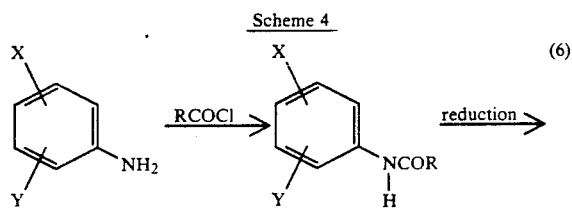

-continued
Scheme 4

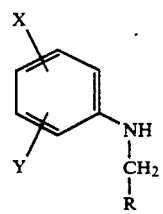

(where p = 1)

The starting oxindole (2) can then be prepared by Friedel-Crafts ring closure of an amide of Formula (7) in the presence of a Lewis acid such as aluminum chloride ($AlCl_3$). Other Lewis acids such as tin tetrachloride ($SnCl_4$) or boron trifluoride ($BF_3$) can be used depending on the chemical structure of the amide (7). Choice of solvent if any is dependent on the actual compound of Formula (7) to be cyclized and on the Lewis acid used. Nitrobenzene, tetrachloroethane, ethylene dichloride and methylene chloride are often used as solvents. Generally, the use of $AlCl_3$ without a solvent is preferred.

If substituents X and Y are electron withdrawing and deactivate the aromatic ring to which they are attached towards electrophilic substitution and if V and W are electron donating or activate the ring (where R is substituted phenyl) other methods may be more convenient for synthesis of oxindoles (2). These methods will be known to one skilled in the art of organic synthesis who is familiar with the literature of oxindole synthesis.

For example, in addition to the Friedel-Crafts cycloalkylation illustrated by Scheme 2, X and Y substituted oxindoles can be made by the general "azasulfonium ion" rearrangement methods of Gassman [U.S. Pat. Nos. 3,897,451 (1975), 3,996,264 (1976), and 3,972,894 (1976); see also *J. Am. Chem. Soc.*, 96, 5512 (1974) etc.] or in some instances from o-nitrophenyl acetic acid [see Walker, *J. Am. Chem. Soc.*,77, 3544 (1955) and Hardigger et al., *Helv. Chim. Acta.*, 39, 514 (1956)].

Compounds of the Formula (4) are preferably prepared as shown in (Scheme 5) by reaction of a substituted isatin (8) with an alkyl pyridine, such as 4-picoline, in acetic acid at 120°–130° C. to yield the aldol addition product (9). The reaction can also be performed in 4-picoline and the product isolated via dilution with methylene chloride followed by filtration and recrystallization of the product. Other high boiling solvents such as xylene or toluene containing an excess of 4-picoline may also be used for this reaction. Substituted isatins (8) are well described in the literature. 1-Phenyl isatin is prepared from diphenylamine and oxalyl chloride as described in *Ber.*,46 3915 (1914). Condensation of alkyl pyridines with carbonyl compounds is described in E. Klingsberg, et.al., *Pyridines and Its Derivatives*, Pt. II, 191–197 (1961).

Scheme 5

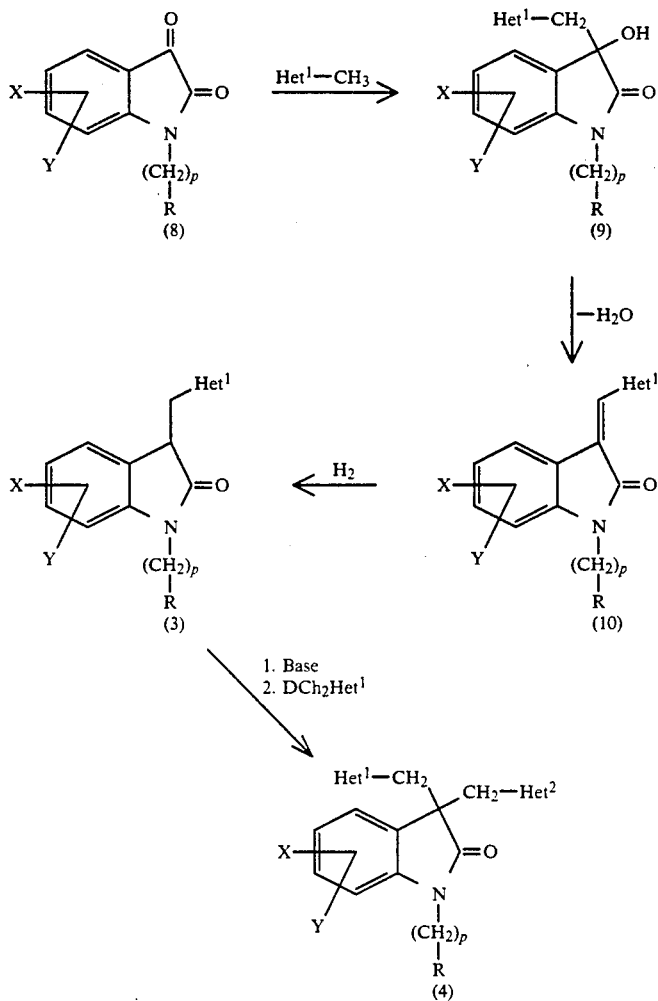

Dehydration of (9) to produce (10) preferably is executed with acetic anhydride between 100°-130° C. This reaction can also be performed in the presence of acetic acid. Other aprotic solvents such as toluene or xylene at elevated temperatures may also be used for the above transformation. Other methods of dehydration familiar to one skilled in the art include zinc chloride, other acid anhydrides, phosphorus pentoxide, potassium bisulfate, and sulfuric acid as described in J. March, *Advanced Organic Chemistry*, 901-903, (1985). Dehydration of carbinols (9) resulting from the condensation of alkyl pyridines with carbonyl compounds is described in E. Klingsberg, et al., *Pyridine and Its Derivatives*, Pt. II, 203 (1961).

Compounds of the Formula (3) are obtained via reduction of (10). Treatment of (10) with sodium borohydride in methanol is the preferred method for conversion of (10) to (3). This method is illustrated in *J. Org. Chem.*, 31, 620 (1966). (3) may also be obtained via transfer hydrogenation as described in *Chem. Rev.*, 85, 129-170 (1985) or via catalytic hydrogenation in acetic acid or ethyl acetate under standard conditions known to one skilled in the art.

The conversion of (3) to (4) is preferably performed in a methanol-water mixture using sodium hydroxide as the preferred base, followed by the reaction of the resultant anionic species with a compound of the formula D—$CH_2$—$Het^2$ where D is preferably halogen, methanesulfonate or p-toluenesulfonate. Other alcohols such as ethanol, isopropanol, n-propanol can be substituted for methanol as described above. Other bases such as potassium hydroxide, lithium hydroxide, and quaternary amines such as N-benzyltrimethyl ammonium hydroxide are also acceptable. Preparation of (4) from (3) can also be accomplished under phase-transfer catalysis using toluene-50% sodium hydroxide as the solvents and hexadecyltributyl phosphonium bromide as the catalyst.

Other more direct synthesis of 3,3-disubstituted 2-oxindoles can be carried out by use of the Brunner reaction of N-arylhydrazides [*Org. Synthesis*, 37, 60 (1957); Rohrscheidt et al., *Liebigs Ann. Chem.*, 680 (1978)] and by processes involving direct oxidation of substituted indoles [Lawson et al., *J. Org. Chem.*, 26, 263 (1961); R. L. Hinman et al., ibid, 29, 1206 (1964); Lawson et al., *J. Am. Chem. Soc.*, 82, 5918 (1960); Szabo-Pusztag et al., *Synthesis*, 276 (1979). Other methods for making oxindoles are described by A. P. Kozikowski, et al., *J. Am. Chem. Soc.*, 43 (10), 2083 (1978); T. Nakashima, et al., *Chem. Pharm. Bull.*, 17 (11), 2293 (1969); Y. Tamura, et al., *Synthesis*, 534 (1981); J. F. Bunnett, *J. Org. Chem.*, 28 (1), 1 (1963); R. R. Goehring, *J. Am. Chem. Soc.*, 107 (z), 435 (1985); T. Hamada, et. al., Chem. Pharm. Bull., 29 (1), 128 (1981); D. Ben-Ishai, et al., Tet. Lett., 21 (6), 569-72 (1980); J. F. Wolfe, J. Am. Chem. Soc., 112 (10), 3646 (1980); J. G. Atkinson, Tet. Lett., (31), 3857 (1979); M. Mori, et al., Tet. Lett., (21) 1807 (1976); P. Parimoo, Indian J. Chem., 10 (17), 764 (1972); D. Klamann, et al., Chem Ber., 100 (6), 1870 (1967).

This bibliographic list is intended to be illustrative of the great variety of methods available to make the 2-oxindole intermediates useful in this invention.

The 2-thiooxindoles (11) of this invention can be made by reaction of the oxindoles with Lawesson's reagent or with phosphorus pentasulfide ($P_4S_{10}$) as is illustrated in Scheme 6.

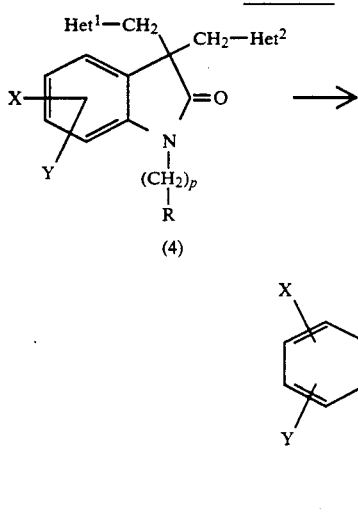

Scheme 6

(4)

(11)

Lawesson reagent is 2,4-bis(4-methoxyphenyl)-1,3-dithia-2,4-diphosphetane-2,4-disulfide. Its use in the thiation of carboxamides and lactams is well known, as is the use of phosphorus pentasulfide for similar reactions. The reactions are customarily carried out in methylene chloride, benzene, toluene, acetonitrile, or piperidine depending on the solvent power and reaction temperature required for the particular oxindole involved. Usually the $P_4S_{10}$ works better if it is first purified by extraction into methylene chloride by Soxhlet extraction. Ordinarily thiation reactions can be carried out at mild temperatures (25°-80° C.) and the products can be isolated by chromatography or crystallization.

The nitrogen-containing heterocyclic compounds $D-CH_2-Het^1$ used as intermediates in Schemes 1 and 2 are available by methods described in standard works on heterocyclic chemistry such as Katritzsky and Rees, Comprehensive Heterocyclic Chemistry, Vols. 2-5, Pergamon Press, N.Y., 1984. In some instances the preparation of the corresponding hydroxy compounds (D=OH) is described in the literature; these can be converted to the corresponding halo compounds (e.g. D=Br) for the alkylation reaction indicated in Schemes 1 and 2 by mild reagent (such as $Ph_3P,CBr_4$). Alternatively the hydroxy compounds can be converted to the corresponding sulfonate esters (e.g. $D=CH_3SO_2O$) by reaction with the corresponding sulfonylchloride in the presence of pyridine or triethylamine at cold temperatures. Generally, temperatures of about 0° C. to −20° C. are preferred for formation of these sulfonates.

Compounds of the Formula (14) (Scheme 7), particularly where $Het^1$ is the same as $Het^2$, can be prepared by treatment of indene (12) with a suitable base followed by displacement of D by the resultant anion forming the 3-substituted indene (13). Indene (13) can then either be isolated prior to the next step or treated again with another equivalent of base and alkylating reagent without prior isolation to give the 3,3-substituted indene (14). D in $DCH_2Het^1$ represents a displaceable group as described in Scheme 1.

Suitable bases for forming the anion include those described for Scheme 1. The reaction is run in an aprotic solvent such as diethylether, glyme, tetrahydrofuran, or dioxane.

In addition to the bases listed previously, other suitable bases are n-butyllithium, tert-butyllithium, sec-butyllithium, methyllithium, and phenyllithium. Starting material (12), where W, Z=H, Q=H, and $R^2$=Ph, can be prepared via addition of phenylmagnesium bromide to 1-indanone, followed by dehydration, Parham and Wright, J. Org. Chem., 22, 1473 (1957).

Other general methods for the preparation of indenes are described in the chemical literature, Parham and Sayed, Synthesis, 116-7 (1976); Greifenstein, et. al., J. Org. Chem., 46, 5125-32 (1981).

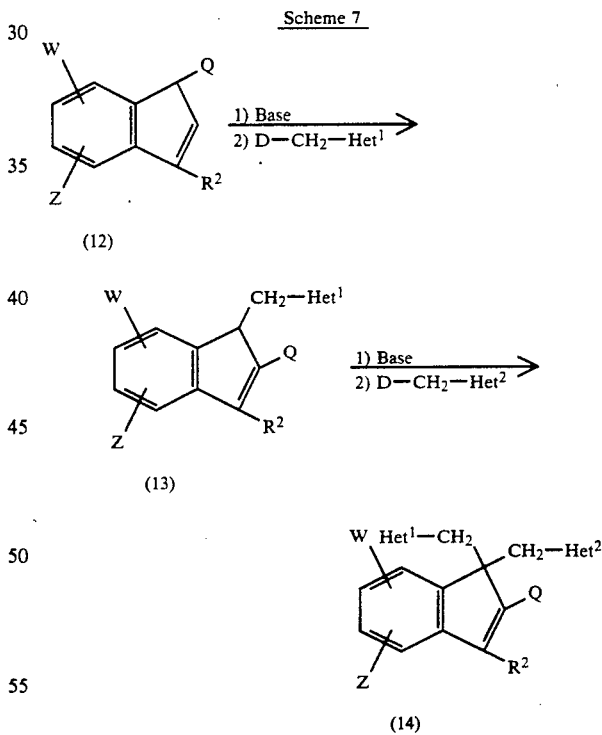

Scheme 7

(12)

(13)

(14)

Compounds of the formula (16) (Scheme 8), where Q and $R^2$ are described above, can be prepared via catalytic reduction of the multiple bond in olefin (14) with hydrogen in the presence of a catalyst such as palladium on carbon (15) or platinum on carbon. This method is limited to compounds in which $R^2$, W or Z is not $NO_2$. Other methods of reduction may be found in House, H. O., Modern Synthetic Reactions, second edition, W. A. Benjamin, Inc., Menlo Park, Calif., 1972.

Scheme 8

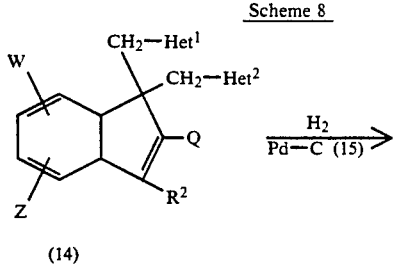

(14)

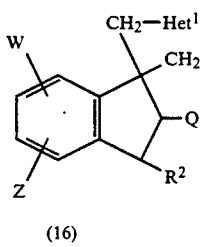

(16)

Compounds of the formula (18) and (19) can be prepared using the methods outlined in Scheme 9. Hydroxylation of the double bond in indene (17) is conveniently achieved with osmium tetroxide, either stoichiometrically or catalytically in the presence of an oxidant such as hydrogen peroxide or N-methyl morpholine-N-oxide, Schroder, *Chem. Rev.* 80, 187 (1980). The diol (18) can be further elaborated into the esters or ethers (19) via methods described in the chemical literature.

Scheme 9

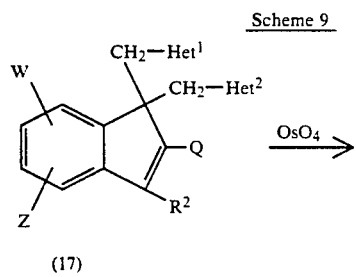

(17)

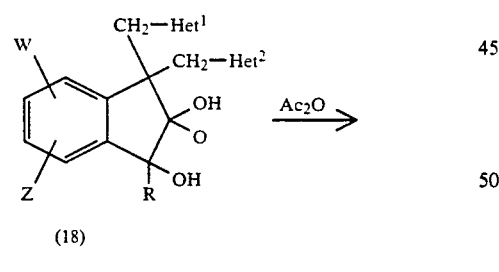

(18)

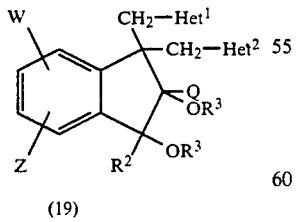

(19)

Compounds of the formula (24) can be prepared using the sequence outlined in Scheme 10. The 2-methoxyphenyl acetonitrile (20) can be dialkylated with D—CH$_2$—Het$^1$ and D-CH$_2$—Het$^2$ via the general methods described for Scheme 1. Het$^1$ and Het$^2$ may be different or the same. If they are the same, the phase-transfer technique described for Scheme 5 is the most convenient method to prepare compounds of the formula (22). The nitrile group in (22) is subsequently hydrolyzed to the acid (23) using basic conditions available in the chemical literature. Lactonisation to compound (24) is achieved by demethylation of (23), followed by dehydration. Demethylation reagents include boron tribromide, Benton and Dillon, *J. Am. Chem. Soc.*, 64, 1128 (1942), McOmie and Watts, *Chem. Ind.*, 1658 (1963); mercaptide ions, Vowinkel, *Synthesis*, 430 (1974); or acids such as hydrogen chloride, hydrogen bromide, and hydrogen iodide, Fieser and Fieser, *Reagents for Organic Synthesis*, Vol. 1-12, Wiley, 1967-1986. This method is limited to compounds in which W or Z is not CN or OR$^3$.

Scheme 10

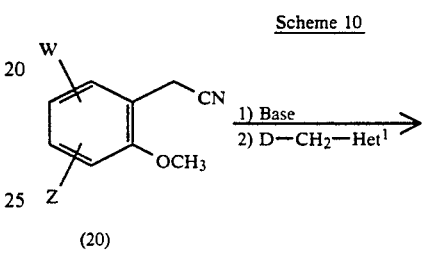

(20)

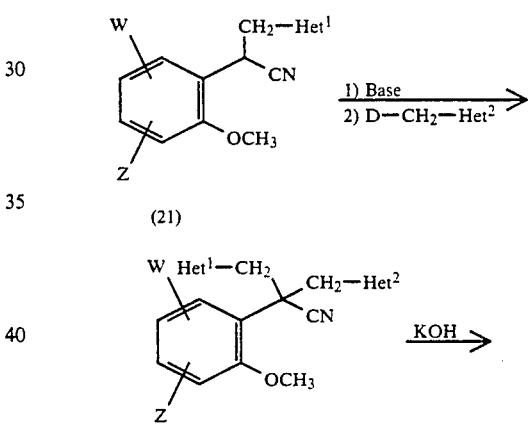

(21)

(22)

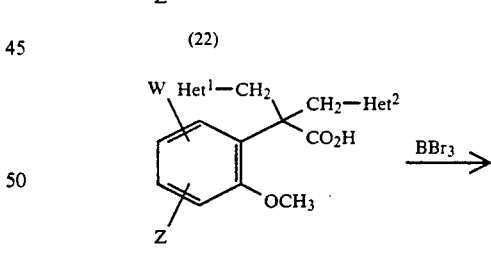

(23)

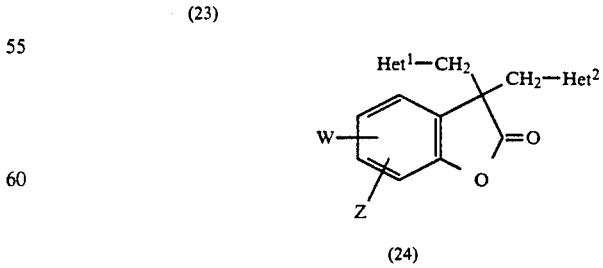

(24)

Compounds of the formula (27), where n is 1 or 2, may be prepared as outlined in Scheme 11, using the reagents and conditions previously described for Scheme 1.

Scheme 11

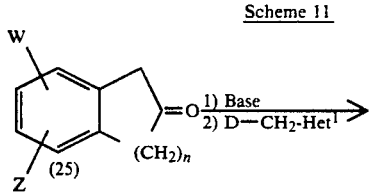

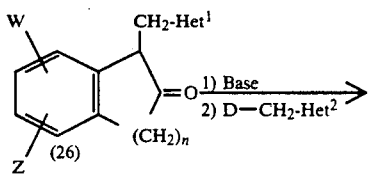

Scheme 12

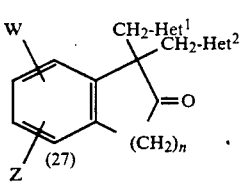

The ketone group in compound (27) can be elaborated to the derivatives as shown in Scheme 12. Compounds of the formula (28) can be prepared via treatment of the ketone (27) with a reagent such as an alkylidene triarylphosphorane (32) (the Wittig reaction) yielding the olefin (28). Olefin (28) can be reduced via catalytic hydrogenation in the presence of a catalyst such as palladium on carbon, or platinum on carbon to yield (29). Compounds of the formula (30) can be prepared via reduction of the ketone with a hydride reagent such as sodium borohydride. Subsequent treatment of alcohol (30) with an acid chloride, or formation of the alkoxide followed by treatment with an alkylating reagent, produces the ester or the ether (31), respectively.

Other ketone derivatives such as oximes, ketals, acetals, thioketals, thioacetals, thioketones, etc., can be prepared via methods described in the chemical literature. The ketone function in (27) can also be reduced to the methylene compound with hydrazine by methods described by Hudlicky, *Reductions in Organic Chemistry*; Halsted Press, N.Y., 1984, or converted into the geminal difluoride with diethylaminosulfur trifluoride as described by W. J. Middleton, *J. Org. Chem.*, 40, 574 (1975). Other ketone derivatives are available to anyone skilled in the art.

Compounds of formula (36), particularly where $Het^1$ is the same as $Het^2$, can be prepared by the synthetic sequence represented by Scheme 13. D represents a displaceable group as described for Scheme 1. Ketone (34) can be prepared via the oxidation of the alcohol (33) with a chromium salt. An example of this technique is reported by E. J. Corey et al., *Tetrahedron Letters*, 2467 (1975). The alkylations result from formation of an anion at the 2-position of the ketone (34) by treatment of the ketone with a suitable base followed by displacement of D by the anion and formation of the 2-monosubstituted ketone (35).

Suitable bases and solvents used for forming the anion include those described for Scheme 1. This mono-substituted ketone (35) can then either be isolated prior to the next step or treated again with another equivalent of base and alkylating reagent without prior isolation, to give the 2,2-disubstituted acenaphthenone (36).

In some cases, especially those where $Het^1$ and $Het^2$ are the same, it may be convenient to accomplish alkylation of the acenaphthenone under phase-transfer conditions, e.g., using a base such as sodium hydroxide dissolved in water, a water immiscible solvent such as benzene or toluene, a phase transfer catalyst such as benzyltriethylammonium chloride and two molar equivalents of the alkylating agent D—CH$_2$—Het. Suitable procedures are described by Stark and Liotta; *Phase Transfer Catalysis. Principles and Techniques*; Academic Press: N. Y., 1978. Under such conditions, vigorous stirring and elevated reaction temperatures, e.g., 50°-80° C., may facilitate conversion to the 2,2-dialkylated acenaphthenone.

Purification of the product generally involves column chromatography followed by recrystallization if necessary. The pure material can be converted to the hydrochloride salt if desired.

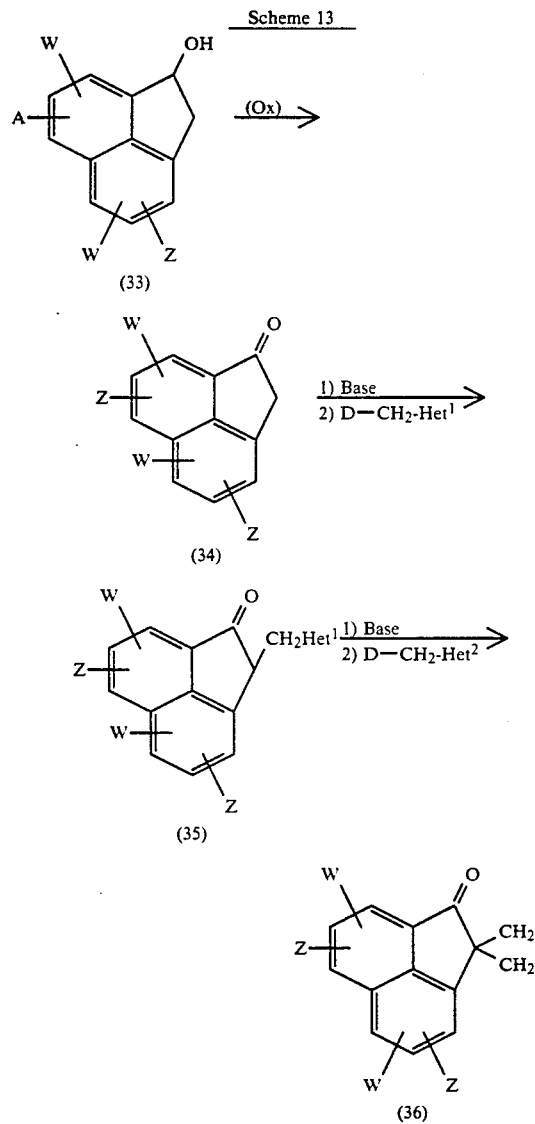

An alternative method of synthesis is illustrated by Scheme 14. Aldol condensation of ketone (34) with the appropriately substituted aldehyde (39) under basic conditions yields the unsaturated ketone (37). An example of this conversion is described by O. Tsuge et al., *Bulletin of the Chemical Society of Japan*, 42, 181-185 (1969). Catalytic reduction of the multiple bond in ketone (37) is performed with hydrogen in the presence of a catalyst such as palladium on carbon. Alkylation of the intermediate ketone with an equivalent of D—CH$_2$—Het$^2$ under the conditions described above or other standard methods described in the chemical literature yield the ketones (38). The required heterocyclic aldehydes (39) are either available commercially, or may be prepared using techniques and methods reported in the chemical literature.

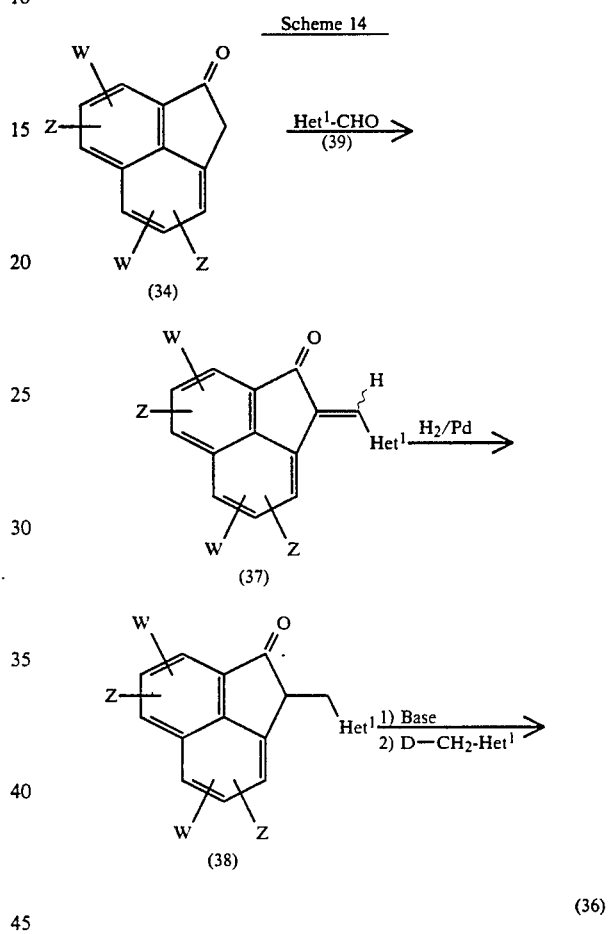

Compounds of the formula (40), where R$^1$ and R$^2$ are as described above, can conveniently be prepared via the method shown in Scheme 15. Treatment of ketones (36) with a reagent such an as alkylidene triarylphosphorane (32) (the Wittig reaction) provides the olefins (40). This method is limited to compounds where W or Z is not COR$^1$. When R$^1$ and R$^2$ are not H, the Z or the E isomer, or a mixture of the two, may be obtained from these reactions.

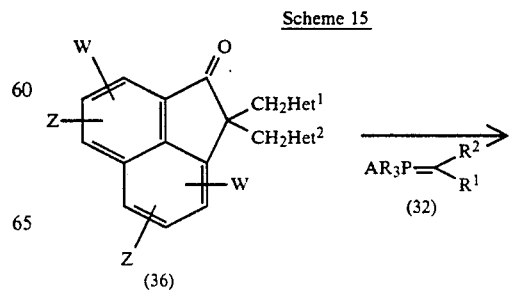

-continued
Scheme 15

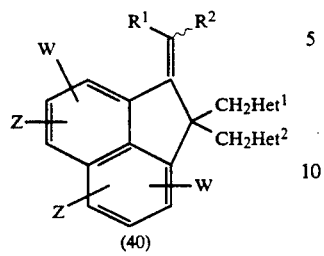

(40)

Compounds of the formula (41), where $R^1$ and $R^2$ are described above, can be prepared via catalytic reduction of the multiple bond in olefin (40) with hydrogen in the presence of a catalyst such as palladium on carbon, or platinum on carbon (Scheme 16). This method is limited to compounds in which W or Z is not $NO_2$. Other methods of reduction can be found in House, H. O., *Modern Synthetic Reactions*, second edition, W. A. Benjamin, Inc., Menlo Park, Calif., 1972.

Scheme 16

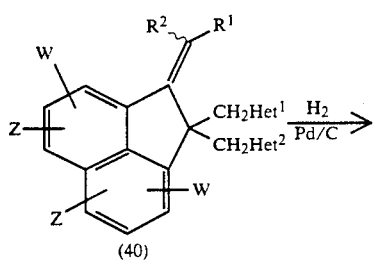

(40)

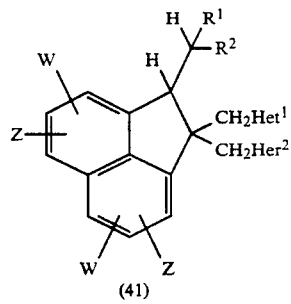

(41)

Compounds of the formula (43), where $R^3$ is as described above, may be obtained via the methods shown in Scheme 17. Reduction of the ketone (36) with a hydride reagent such as lithium aluminum hydride provides the alcohol (42). Treatment of (42) with an acid chloride, or formation of the alkoxide followed by treatment with an alkylating reagent, produces the ester or the ether, respectively.

Scheme 17

(36) $\xrightarrow{\text{LiAlH}_4}$

-continued
Scheme 17

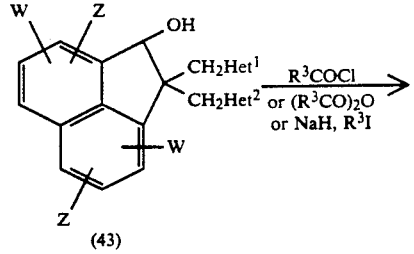

(43)

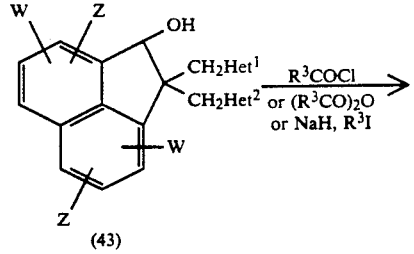

(43)

Compounds of the formula (49) are prepared using the sequence outlined in Scheme 18. The substituted phenylacetonitrile (44) can be dialkylated with D—$CH_2$—$Het^1$ and D—$CH_2$—$Het^2$ via the general methods described for Scheme 1. $Het^1$ and $Het^2$ may be different or the same. If they are the same, the phase-transfer technique described for Scheme 5 is the most convenient method to prepare compounds of the formula (45). The nitrile group in (45) is subsequently reduced to the amine (46) as described by C. Kaiser and P. A. Dandridge, et. al., *J. Med. Chem.* 28, 1803 (1985), or by similar methods outlined in the chemical literature. The amine (46) is converted into the amide (47) using an acid chloride or acid anhydride. Conversion to the dihydroisoquinoline (48) is accomplished using phosphorus oxychloride or other reagents known to affect Bischler-Napieralski cyclization; W. M. Whaley and T. R. Govindachari, *Org. Reactions* 6, 74 (1951). Catalytic reduction over palladium or platinum provides compounds of the formula (49).

Scheme 18

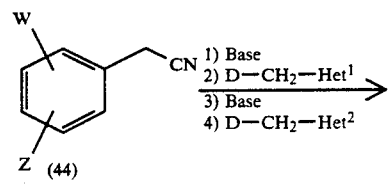

(44)

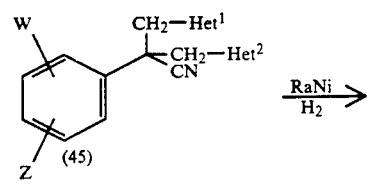

(45)

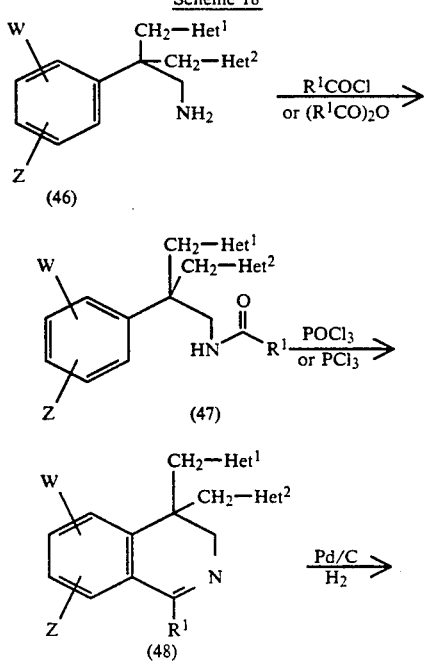

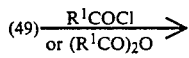

Compounds of the formula (49) can also be prepared as outlined in Scheme 19. Condensation of amine (46) with an aldehyde under Pictet-Spengler reaction conditions; W. M. Whaley and T. R. Govindachari, *Org. Reactions* 6, 151 (1951), Abramovich, *Adv. Heterocyclic Chem.* 3, 79 (1964), Stuart, et. al., *Heterocycles* 3, 223 (1975) will produce compound (49).

Scheme 19

(46) —R¹CHO→ (49)

Compounds of the formula (50) are prepared by treating (49) with an acid anhydride or an acid chloride (Scheme 20) as previously described for Scheme 17.

Scheme 20

(49) —R¹COCl or (R¹CO)₂O→

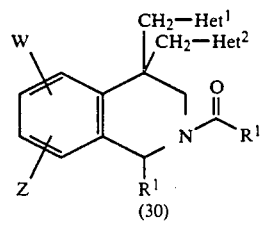

Compounds of the formula (55) can be prepared using the sequence outlined in Scheme 21. The benzyl amine starting material (51) can be prepared from the corresponding benzaldehyde, through reduction to the benzyl alcohol followed by conversion to the benzyl halide and amination with dimethylamine. Alternatively, (51) can be prepared via a Mannich reaction directly on the aromatic substrate with formaldehyde and dimethylamine; F. F. Blick, *Org. Reactions* 1, 303 (1942). Amine (51) can be converted into protected benzyl alcohol (52) through treatment with a strong base, such as butyllithium or lithium diisopropylamine, addition of formaldehyde, and introduction of a protecting group such as trimethylsilyl or 2-tetrahydropyranyl. Compound (52) can then be converted into the phenylacetonitrile (53) via treatment with ethyl chloroformate followed by potassium cyanide; R. S. Mali, et. al., *Indian J. Chem.* 22B, 256 (1986). Compound (53) is then dialkylated with D—CH₂—Het¹ and D—CH₂—Het² via the general methods described for Scheme 1. Hydrolysis of the resulting product (54), followed by deprotection of the alcohol group provides compounds of the formula (55).

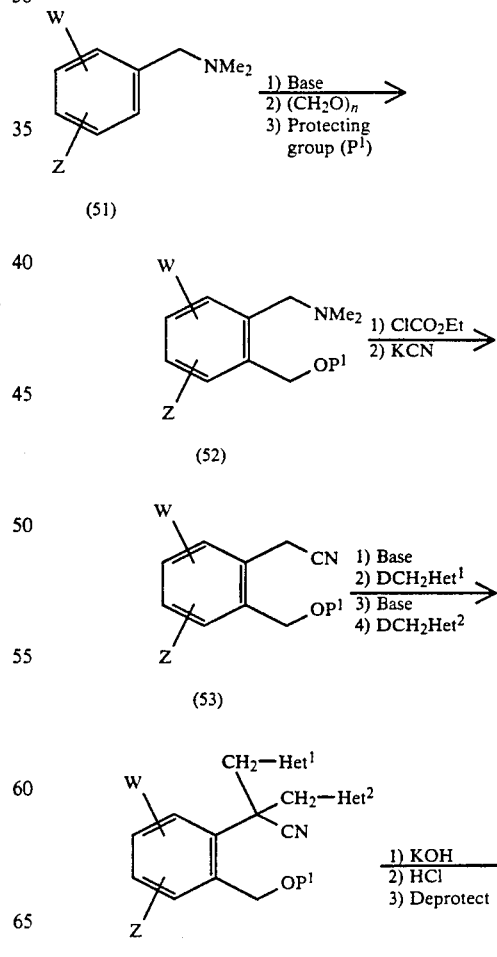

Scheme 21 -continued

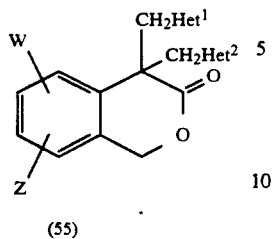

(55)

Compounds of the formula (56) can be prepared by treating (55) with a primary amine. Heat is usually required for this transformation (Scheme 22).

Scheme 22

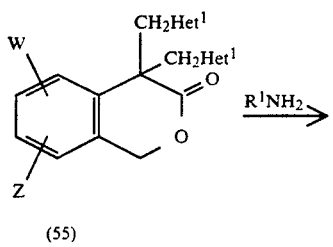

(55)

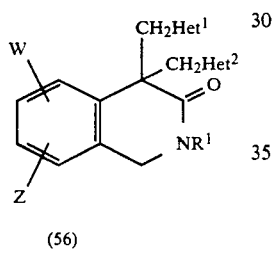

(56)

Compounds of the formula (60) can be prepared according to the sequence outlined in Scheme 23. Treatment of (51) with a strong base such as butyllithium or lithium diisopropylamine, followed by ethyl chloroformate provides (57). This compound is then carried through the same series of reactions described in Scheme 21 to produce anhydrides (60).

Scheme 23

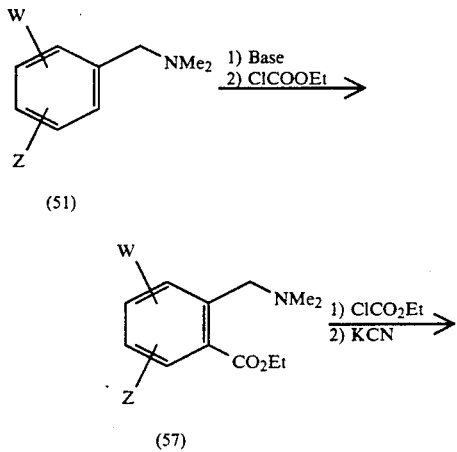

Scheme 23 -continued

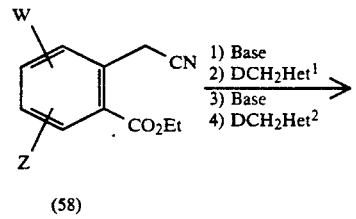

(58)

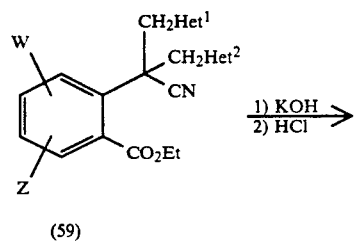

(59)

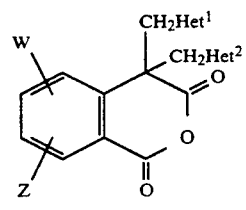

(60)

Compounds of the formula (61) can be prepared by heating anhydrides (60) with a primary amine (Scheme 24).

Scheme 24

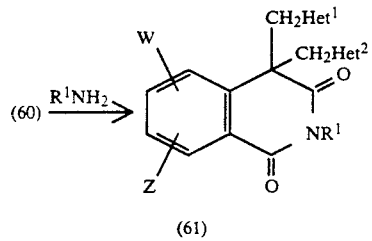

(61)

Compounds of the formula (60) can also be prepared according to Scheme 25. Hydrolysis of the nitrile (58) provides anhydride (62), which is then dialkylated with D—CH$_2$—Het$^1$ and D—CH$_2$—Het$^2$ via the general methods described for Scheme 1.

Scheme 25

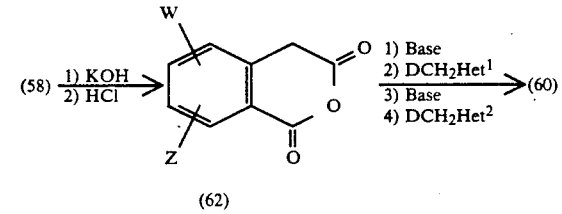

(62)

Compounds of the formula (61) are also prepared according to Scheme 26. Treatment of anhydride (62) with a primary amine produces imide (63); Ueda, et. al, *J. Polym. Sci., Polym. Chem. Ed.* 17, 2459 (1979). This compound is dialkylated with D—CH$_2$—Het$^1$ and D—CH$_2$—Het$^2$ via the general methods described for Scheme 1.

Scheme 26

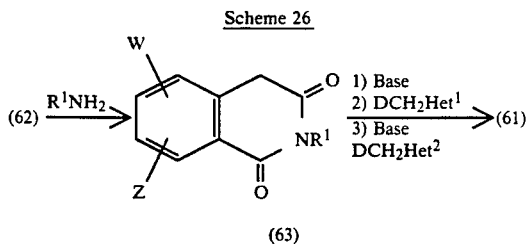

(63)

Scheme 28

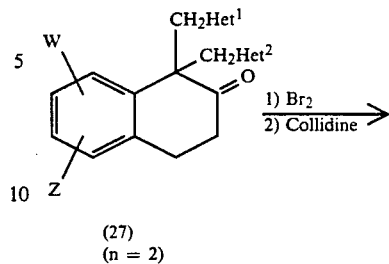

Compounds of the formula (64) can be prepared via reduction of the nitrile portion of compound (59), followed by hydrolysis of the ester and ring closure (Scheme 27).

Scheme 27

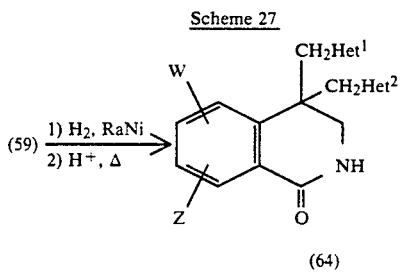

(64)

Compounds of the formula (65) can be prepared according to Scheme 28. Treatment of tetralone (27, n=2) with bromine, followed by dehydrohalogenation with collidine produces naphthalenones (65).; Marvell and Stephenson, *J. Am. Chem. Soc.* 77, 5177 (1955). These compounds may also be prepared via the sequence described in Scheme 23. 2-Naphthols (66) can be treated with a strong base such as lithium tert-butoxide in the presence of alkylating agent D—CH$_2$—Het$^1$ to produce (65); Bram, et. al., *J. Chem. Soc., Chem. Commun.*, 325 (1980), Bram, et. al., *Tetrahedron Lett.* 25, 5035 (1984). This method seems to be limited to those cases where Het$^1$ and Het$^2$ are the same.

(65)

Scheme 29

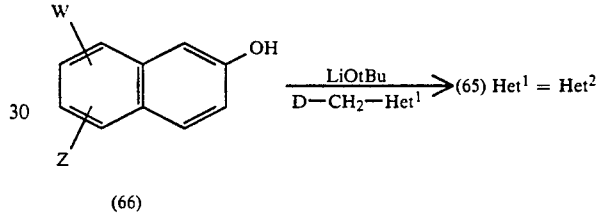

(66)

Derivatives of (65) can be prepared via the general reactions described in Scheme 30. Treatment of (65) with Lawesson's reagent provides thioketone (67); Rao and Ramamurthy, *J. Org. Chem.* 50, 5009 (1985). Treatment of (65) with a phosphonium ylid or similar compound produces olefin (68). Reactions of this type are well known in the chemical literature. Alternatively, (68) can be prepared from (65) via an aldol-type reaction with, e.g. a nitroalkane, alkylcyanide, or alkyl ester. Compounds of the formula (69) can be prepared via reduction of the ketone with diisobutylaluminum hydride; Mathur, et. al., *Tetrahedron* 41, 1509 (1985). The alcohol may be converted into the ester (70) via methods described previously for Scheme 17.

Scheme 30

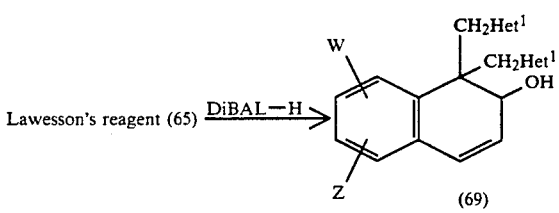

Scheme 30

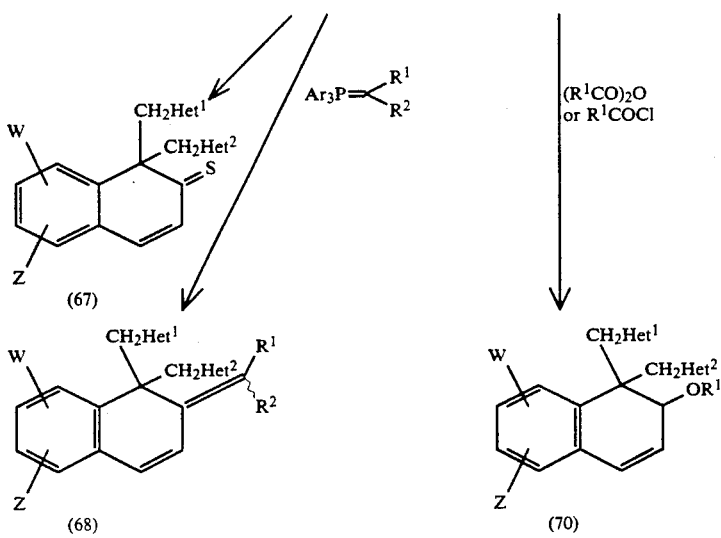

Compounds of the formula (72) are prepared according to Scheme 31. Lactone (71) is prepared from the acenaphthenone according to O'Brien and Smith, *J. Chem. Soc.* 2907–17 (1963). This compound is dialkylated with D—CH$_2$—Het$^1$ and D—CH$_2$—Het$^2$ via the general methods described for Scheme 1. A phase transfer method described by Chan and Huang, *Synthesis,* 452 (1982) proved to be particularly useful in cases where Het$^1$ and Het$^2$ are the same.

Compounds of the formula (75) can be prepared according to Scheme 32. Amide (73) can be prepared from the acenaphthenone according to O'Brien and Smith, *J. Chem. Soc.* 2907–17 (1963). Alkylation or arylation on nitrogen provides (74); Renger, *Synthesis,* 856 (1985). This compound is then dialkylated with D—CH$_2$—Het$^1$ and D—CH$_2$—Het$^2$ via the general methods described for Scheme 1.

Scheme 31

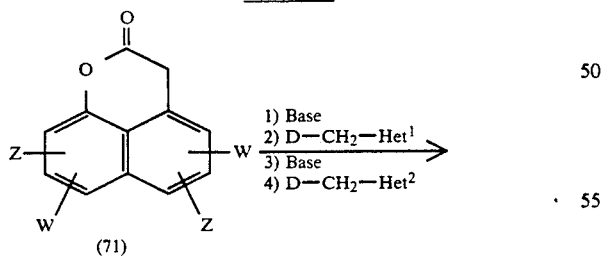

Scheme 32

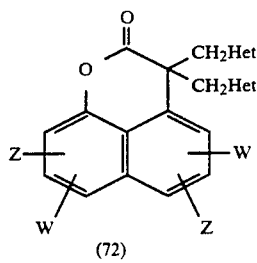

Compounds of the formula (77) can be prepared according to Scheme 33. Phenalenes (76) are prepared according to the literature; Bauld, et. al., *Tetrahedron Lett.,* 2865 (1979), Jorgensen and Thomsen, *Acta Chem. Scand. B* 38, 113 (1984). This compound is then dialkylated with D—CH$_2$—Het$^1$ and D—CH$_2$—Het$^2$ via the general methods described for Scheme 1. The ketone group in (77) can be converted into the thioketone, olefin, alcohol, or ester according to Scheme 30 or by other methods described in the chemical literature.

Other ketone derivatives are available to anyone skilled in the art.

Compounds of the formula (78) and (79) can be prepared according to Scheme 34. Treatment of (77) with base, followed by addition of an alkylating agent such as methyl iodide, ethyl iodide, etc. produces enol ether (78). Addition of an organometallic species such as phenylmagnesium bromide to (77), followed by dehydration, provides olefin (79).

Compounds of the formula (81) can be prepared according to Scheme 35. The ketones (80) can be dialkylated with D—CH$_2$—Het$^1$ and D—CH$_2$—Het$^2$ via the general methods described for Scheme 1. The starting materials are prepared via literature methods: —A— is —CH$_2$— or —CH$_2$CH$_2$—, Leonard, et. al., *J. Am. Chem. Soc.* 77, 5078 (1955); —A— is —O—, Ikuo, et. al., *Chem. Pharm. Bull. Japan* 23, 2223 (1975), Protiva, et. al., *Coll. Czech. Chem. Commun.* 34, 2122 (1969); —A— is —S—, Protiva, et. al., *Monatsh. Chem.* 96, 182 (1965), Kimoto, et. al., *Yakugaku Zasshi* 88, 1323 (1968), Protiva, et. al., *Coll. Czech. Chem. Commun.* 34, 1015 (1969); —A— is —NR$^3$—, Allais, et. al., *Eur. J. Med. Chem.—Chim. Ther.* 17, 371 (1982), Schindler and Blattner, U.S. Pat. Nos. 3,144,400 and 3,130,191. The ketone group in (81) can be converted into the thioketone, olefin, alcohol, or ester according to Scheme 30 or by other methods described in the chemical literature. Other ketone derivatives are available to anyone skilled in the art.

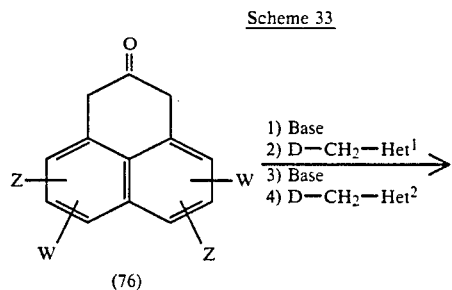

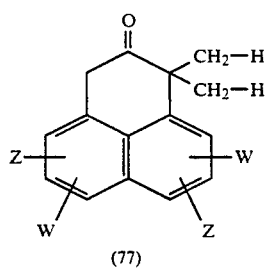

$A = S, O, NR_3, —CH_2—, —CH_2—CH_2—$

Compounds of the Formula (83) (Scheme 36) can be prepared from anthra-9,10-quinones (82) by catalytic reduction with nickel or chemical reduction with tin, tin chloride, iron, aluminum or copper in sulfuric, hydrochloric, and acetic acid as described in *Chem. Berichte* 20, 1854 (1887); *Ann.* 379, 55 (1911); *Chem. Be-*

*richte*, 58, 2675 (1925), and *Bull. Soc. Chim. France* [4], 33, 1094 (1923).

The following Schemes 36-63 show the preparation of core ring structures with active methylene sites (compounds 83, 86, 87, 89, 91, 97, 100, 102, 116, 121, 124, 127, 128, 130, 131, 133). These compounds are then alkylated via the methods described for Scheme 1.

Scheme 36

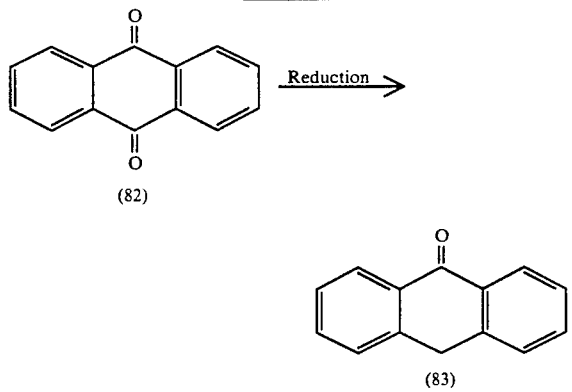

Compounds of the formula (83) can also be prepared via ring closure of benzyl benzoic acids (84) under Friedel-Crafts conditions (Scheme 37) as described by the following: *Ann.*, 234, 235 (1886); U.S. Pat. No. 21,053,430; *J. Org. Chem.*, 23, 1786 (1958); U.S. Pat. No. 2,174,118.

Scheme 37

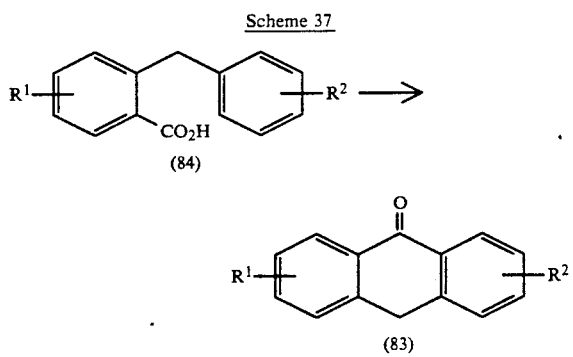

Alkyl and halogen substituted anthrones can be prepared via reduction of the corresponding anthraquinone. 1-Chloro-9,10-anthraquinone (85) is reduced to 1-chloroanthrone (87) via reduction with iron and iron chloride (Scheme 38) as described in German Pat. 249,124. 4-Chloroanthrone (86) is produced via reduction of (85) with aluminum in sulfuric acid as described in *FIAT Final Report Nr*, 1313 II, 105(1948).

Scheme 38

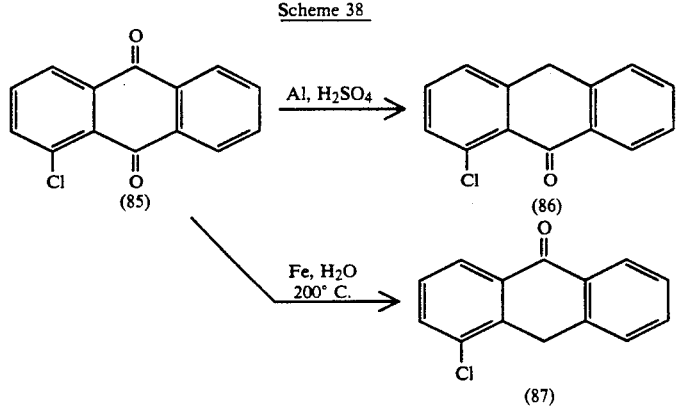

Other halo- and alkyl anthrones are described by the following: German Pat. 598,476; Ber., 66, 1876 (1933); J. Chem. Soc., 123, 2549 (1923).

Hydroxy-anthrones (89) are prepared from hydroxy-9,10-anthraquinones (88) by reduction with tin in acetic and hydrochloric acids (Scheme 39) as described in *J. Am. Chem. Soc.*, 52, 4887 (1930) or by reduction with zinc (German Pat. 296,091; 301,452). Further hydroxy-anthrones are described by the following: Ann., 212, 28 (1882); Brit. Pat. 353,479.

Scheme 39

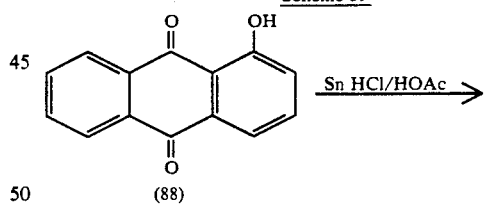

Methoxy-anthrones are prepared as above via reduction of the corresponding anthraquinone described in *J. Chem. Soc.*, 2726, (1949). Amino-and acetamido-anthrones are prepared via reduction of the corresponding anthraquinone (German Pat. 201,542).

Compounds of the Formula (91), can be prepared by the addition of ten parts methylene chloride to a mixture of fifteen parts biphenyl (90) and one part aluminum chloride as described by Adam, *Annales de Chimie*, [6], 15, 235 (Scheme 40).

Scheme 40

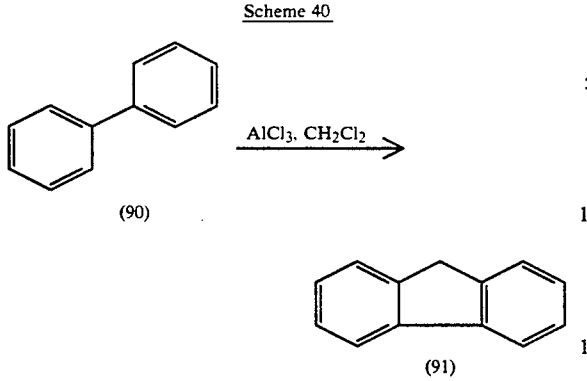

Also, conversion of 2-aminodeiphenylmethane (92) to the corresponding diazonium salt and subsequent cyclization at elevated temperatures yields (91) (Scheme 41) (Ber, 27, 2787).

Scheme 41

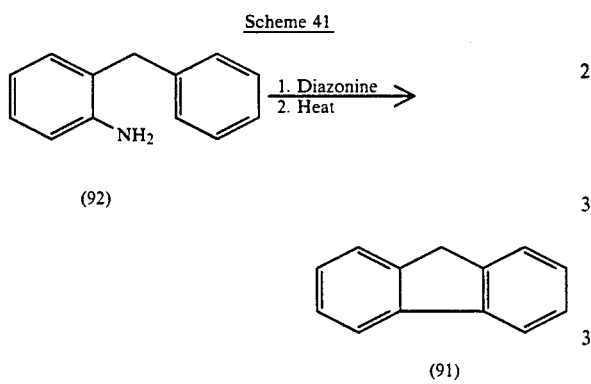

Halogenated derivatives of (91) are readily available. 2-Chlorofluorene is prepared by heating the corresponding diazonium salt with cuprous chloride in concentrated mineral acid (Bull. Soc. Chem. France, [4], 41, 1626). Bromination of (91) in chloroform yields 2-bromofluorene (J. Chem. Soc. 43, 165, (1883). Iodination of (91) occurs by heating fluorene-2-diazonium iodide with cuprous iodide in hydroiodic acid (Bull. Soc. Chem. France, [4], 41, 1626). Nitration of (91) with nitric acid in acetic acid yields 2-nitrofluorene as described by Kuhn, Org. Syn., 13, 74, (1933).

Further nitration or halogenation of the above species may occur as described in Ann., [10], 14; J. Chem. Soc., 43, 170, (1883); Ann., [10], 14, 104 (1930). Reduction of nitrofluorenes with zinc in boiling alcohol-water mixtures yields the corresponding amino-fluorene as described by Diels, Ber., 34, 1759 (1901).

Carboxylated derivatives of (91) are known. Fluorene-2-carboxaldehyde is produced via treatment of (91) with hydrogen cyanide and aluminum chloride in chlorobenzene as described by Hinkel, J. Chem. Soc., 339, (1936). Treatment of (91) with acetic anhydride and aluminum chloride yields 2-acetylfluorene as described by Bochmann, J. Amer. Chem. Soc., 62, 2687 (1940).

Compounds of the formula (91) may also be prepared by the reduction of fluorenone (93) (Scheme 42) with hydroiodic acid in the presence of phosphorus (Ber., 36, 213) or under standard WolffKischner conditions using hydrazine in the presence of potassium hydroxide.

Scheme 42

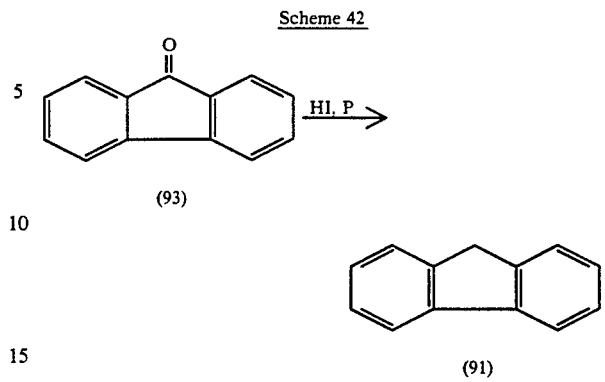

Treatment of fluorene with acetic anhydride and AlCl$_3$ in CS$_2$ yields 2-acetylfluorene, (Ray, J. Amer. Chem. Soc., 65 836 [1943]; Org. Synth., Coll. Vol. III, 23 [1955]; Bachmann, J. Am. Chem. Soc. 62, 2687–2688 [1940]. Treating 2-nitrofluorene with acetylchloride and AlCl$_3$ in nitrobenzene at 40°–55° yields 7-nitro-2-acetylfluorene (Oehlschlaeger, J. Am. Chem. Soc. 71, 3223 [1949].

Fluorenone (93) is prepared in quantitative yield by treating diphenyl-2-carboxylic acid chloride (94) with AlCl$_3$ in benzene (Scheme 43)

Scheme 43

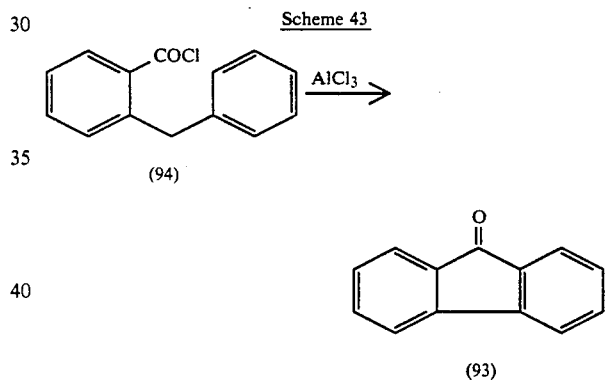

(Ann., 464 33) or by treating it with phosphorus pentachloride (Bachmann, J. Am. Chem. Soc., 49, 2093) or thionylchloride (Bell, J. Chem. Soc., 3247 (1928).

Substituted fluorenones are prepared as follows: 1-bromofluorenone is prepared from 2,6-dibromobenzophenone (Rec. Trav. Chem., 32, 167). 2,4-Dibromobenzophenone yields 1,3-dibromofluorenone (Rec. Trav. Chem., 32, 173). Treating 9,9-Dichloro-2,7-dibromofluorene with PCl$_5$ at 210°–220° C. yields 2,7-dibromofluorenone (Annalen der Chemie, 387, 156). Treating 2,9,9-trichlorofluorene with water yields 2-chlorofluorenone (Ber., 54, 2073). Preparation of 2-nitrofluorenone is described in (Rec. Trav. Chem., 48, 897); (Annalen der Chemie, 43, 65). 4-Nitrofluorenone is described by Morgan, J. Chem. Soc., 2696, 1926. 1,8-Dinitrofluorenone is described by Huntress, J. Am. Chem. Soc., 54, 827, (1932). Preparation of 2,5-dinitrofluorenone by nitration is described by Morgan, J. Chem. Soc., 1926, 2696. 1,4-dimethylfluorenone is prepared from 2,5-dimethylbenzophenone-2-diazonium sulfate and copper powder (Ber., 53, 1395). 2-Fluorofluorenone is prepared by treating the 2-diazonium salt of fluorenone with HBF$_4$ and heating the tetrafluoroborate salt to 180° C. (Ber. 66, 46, S2 [1933]. 2-Chlorofluorenone is prepared from 4-chlorobiphenyl-2-carboxylic acid or from 4-chlorobiphenyl-2-carboxylic acid in conc. H₂SO₄ at 50° C. (*J. Chem. Soc.*, 113, (1950). Heating 4-Bromobiphenyl carboxylic acid with conc. sulfuric acid produces 2-bromofluorenone (*J. Chem. Soc.*, 113, (1938). Treatment of 1-aminofluorenone with nitrous acid and potassium iodide yields 1-iodofluorenone *J. Am. Chem. Soc.*, 64, 2845, (1942). The treatment of 4-nitrobiphenyl carboxylic acid with H₂SO₄ yields 2-nitrofluorenone (*J. Chem. Soc.*, 113, (1938), and 5-nitrobiphenyl carboxylic acid yields 3-nitrofluorenone (*J. Chem. Soc.*, 70, 1492 [1948]). 7-Bromo-2-nitrofluorenone is produced from 9-bromofluorene and nitric acid (*J. Chem. Soc.*, 1607, (1935). 2,5-dinitrofluorenone and 2,7-dinitrofluorenone are produced by nitric acid on fluorenone (*J. Chem. Soc.*, 68 2489, [1946]). Treatment of 2-amino-3,4-dimethylbenzophenone with sodium nitrite in hydrochloric acid and warming the reaction yields 2,3-dimethylfluorenone (*J. Chem. Soc.*, 63, 2564-2566 [1941]). Reacting 2-bromofluorenone with ammonium hydroxide in the presence of Cu(I)Cl yields 2-aminofluorenone (*Bull. Soc. Chem. France*, [4] 41 61). Dimethylsulfate reacts with 2-aminofluorenone to produce 2,2-dimethylamino fluorenone (*Monats.*, 41, 209), and treatment with acetic anhydride produces 2-acetamido fluorenone (*Monats.*, 41, 207). Treating 3-hydroxydiphenyl-2-carboxylic acid with H₂SO₄ produces 1hydroxy-fluorenone (*Ber.*, 28, 113), and further reaction with methyliodide yields 1-methoxy fluorenone (*J. fur prakt. Chem.*, 59 453). Prep of 4 cyanofluorenone is described (Ber., 47, 2825) and vacuum distillation of 2-cyanodiphenyl carboxylic acid chloride produce 4-cyanofluorenone (*J. Chem. Soc.*, 3248, (1928). All other positional isomers may be prepared in a similar manner to those transformations described above.

Other fluorenone preparations are described by *J. Fur. Prakt. Chem.*, [27] 123 331; *Comptes Rendue* 184, 608*Ber.*, 53 2243; *Bull. Soc. Chim. France*, [43], 41 71; Annalen 436 5; (*J. Chem. Soc.*, 2696, (1926); (*J. Chem. Soc.*, 54, 827 (1932); (*J. Chem. Soc.*, 2694, (1926); (*J. Chem. Soc.*, 20, 3958, (1948); (*J. Chem. Soc.*, 65,836 (1943); (*J. Chem. Soc.*, 62, 2687, (1940).

Azafluorenes (97) can be prepared via reduction of azafluorenones (96) by hydrogen iodide in the presence of phosphorus. Azafluorenones (96) are prepared by cyclization of 2-(2-phenylcarboxylic acid)-pyridine-3-carboxylic acid (95) (Scheme 44) as described in *Monatsh.*, 4, 472; Ber., 23, 1237; *J. Chem. Soc.*, 125, 2369.

(99) followed by cyclization with sulfuric acid (*J. Fur Prakt. Chem.*, 54, 217 [1896]) (Scheme 45).

Scheme 45

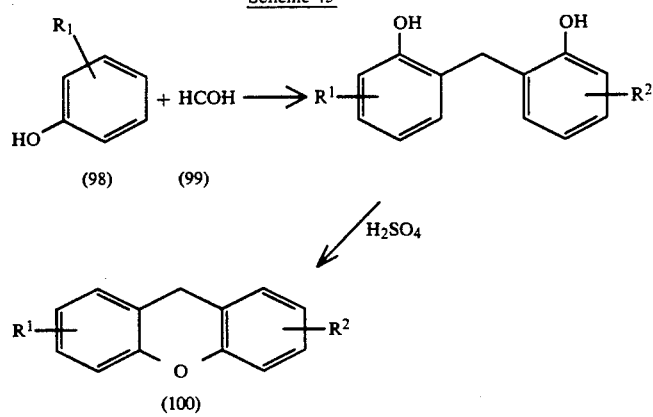

Alkylxanthenes are prepared by distillation of cresols (*Ber.* 49 169 [1916]). Treating 2'-chloro-2-hydroxy-5-methylbenzophenone (101) with hydrazine hydrate produces 2-methyl xanthene (102), (Scheme 46) (*J. Am. Chem. Soc.*, 73, 2483 [1951]).

Scheme 46

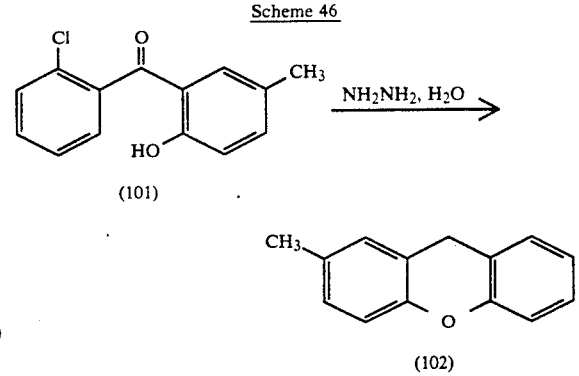

Xanthene (100) may also be repared by reducing xanthen-9-ones with sodium or hydrogen iodide in the presence of red phosphorus (*J. Chem. Soc.*, 812, (1956) or by Wolff-Kischner conditions as described in U.S. Pat. No. b 2,776,299.

Scheme 44

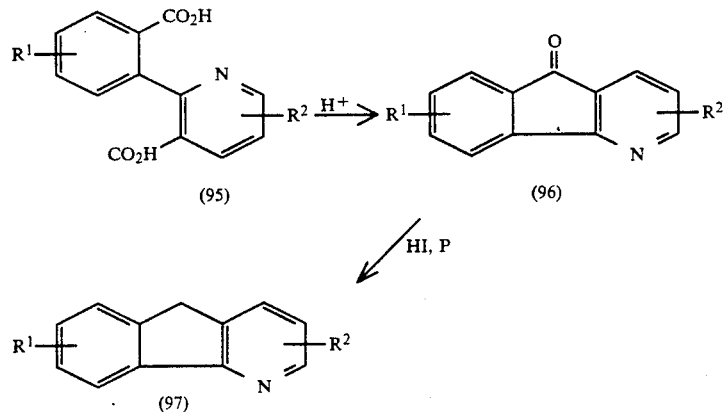

Compounds of the Formula (100) are prepared by reacting substituted phenols (98) with formaldehyde Xanthones (104) can be prepared by acid catalyzed cyclization of substituted-diphenylether-2-carboxylic acids (103) (Scheme 47).

Scheme 47

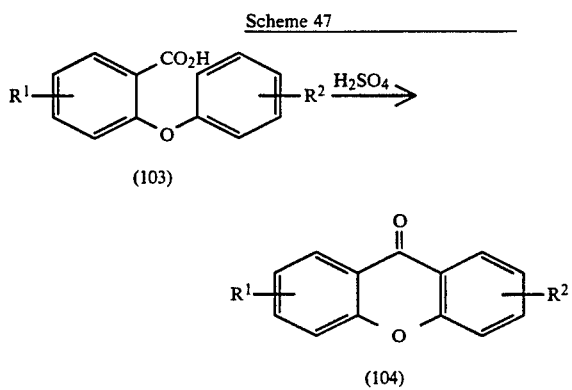

(103)

(104)

For example, 2-chloroxanthone is formed from heating 4 chlorodiphenylether-2-carboxylic acid in sulfuric acid at 100° C. (*Annalen.* 355 366, 371 388). The haloisomers may be prepared in a similar manner (*Annalen.* 370 183, 371 389). Haloxanthones can be prepared by direct halogenation of xanthone as described in *J. Chem. Soc.*, 109, 745 (1916).

Substituted xanthones can be prepared from substituted salicylic acids (105) and acetic anhydride (Scheme 48) and from treating substituted 2-hydroxybenzophenones (106) with a base such as sodium hydroxide (Scheme 49) (*Ber.*, 38 1488, 1494, 39 2361; *Ann.*, 254 284).

Scheme 48

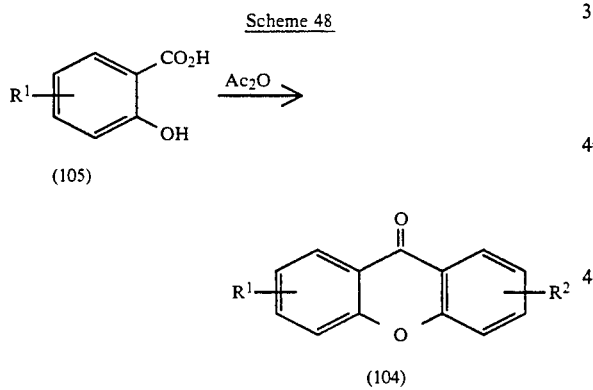

(105)

(104)

Scheme 49

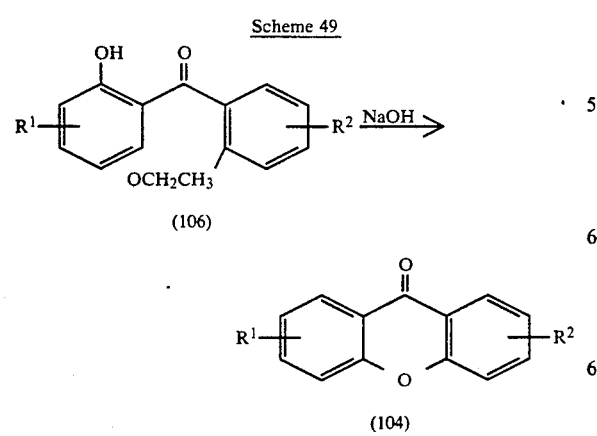

(106)

(104)

Fluoroxanthones are prepared from 2-[fluorophenoxy]-benzoic acids, (*Tetrahedron*, 6 315 [1959]). Haloxanthones may also be prepared from the xanthondiazonium salts (*J. Chem. Soc.*, 1958 4234, 4238). Halo-substituted-xanthones can then be reduced to halo-xanthenes by lithium aluminum hydride, sodium in alcohol, and hydrogen iodide in the presence of red phosphorus, (*J. Am. Chem. Soc.*, 77 5121, 5122 [1955]). Further preparations of haloxanthones are described J. Org. Chem., 28 3188, 3193 [1963]; *J. Am. Chem. Soc.*, 77 543, 546 [1955]. Nitroxanthones can be prepared by direct nitration of xanthone or by cyclization of 2-(nitro-phenoxy)-benzoic acid with sulfuric acid and acetic anhydride or phosphoryl chloride, *J. Am. Chem. Soc.*, 56 120 [1934].

Aminoxanthenes can be prepared by reduction of nitroxanthenes or nitroxanthones with tin (II) chloride in hydrochloric/acetic acids, or metallic tin in acid, (*J. Chem. Soc.*, 109 747). Acylation of the amino-xanthene or xanthones produces acylaminoxanthene or xanthones, *J. Pharm. Soc. Japan*, 74, 610 [1954]. Hydroxy and alkoxyxanthenes (109) and xanthones are prepared by reacting salicyclic acid (107) with resorcinol (108) and zinc chloride at 180° C. (Scheme 50).

Scheme 50

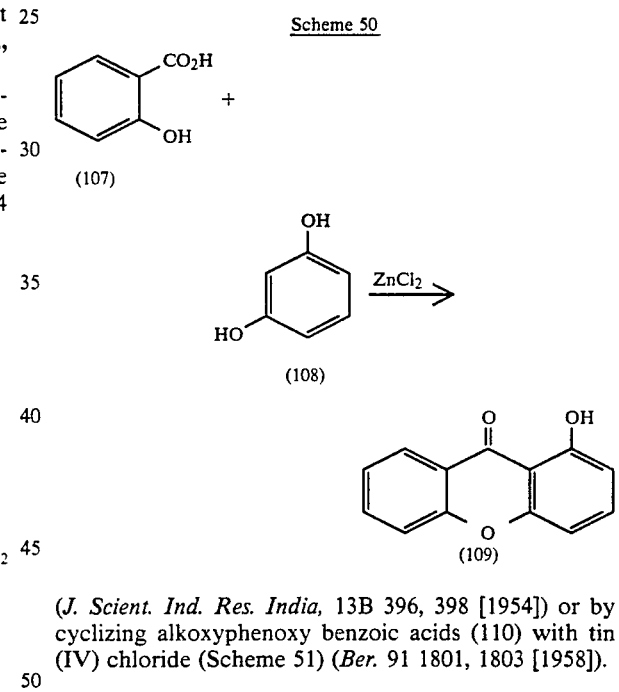

(107)

(108)

(109)

(*J. Scient. Ind. Res. India*, 13B 396, 398 [1954]) or by cyclizing alkoxyphenoxy benzoic acids (110) with tin (IV) chloride (Scheme 51) (*Ber.* 91 1801, 1803 [1958]).

Scheme 51

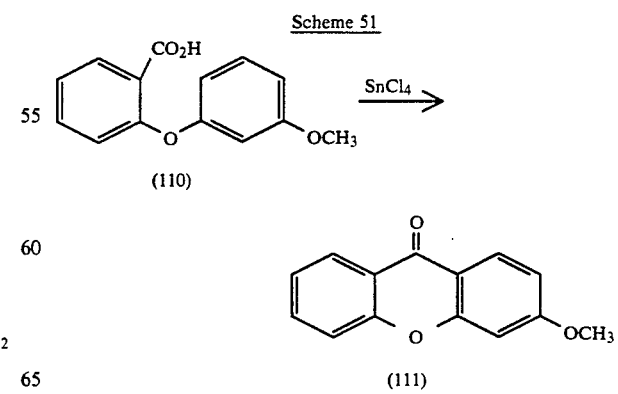

(110)

(111)

*Ber.* 81 19, 24 [1948]). Hydroxyxanthenes can be reacted with dimethylsulfate or alkyliodide to yield alkoxy-xanthenes (*J. Am. Chem. Soc.*, 79 2225, 2229 [1957]. Cyanoxanthones (113) are prepared by ring closure of cyanophenoxybenzoic acid (112) (Scheme 52) (*J. Chem. Soc.*, 4227, (1958).

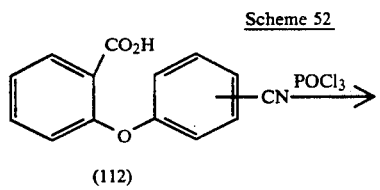

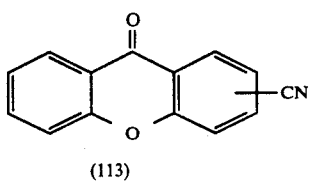

Compounds of the Formula (116) can be prepared by reduction of thioxanthones (115) by sodium in alcohol, hydrogen iodide in the presence of phosphorus, and Wolff-Kishner conditions using hydrazine hydrate and ethylene glycol. Thioxanthones are prepared by cyclizing phenylmercaptobenzaldehydes (114) (Scheme 53).

with sulfuric acid (Scheme 54), to yield (118), (*J. Org. Chem. Soc.*, 24 1914 [1959]).

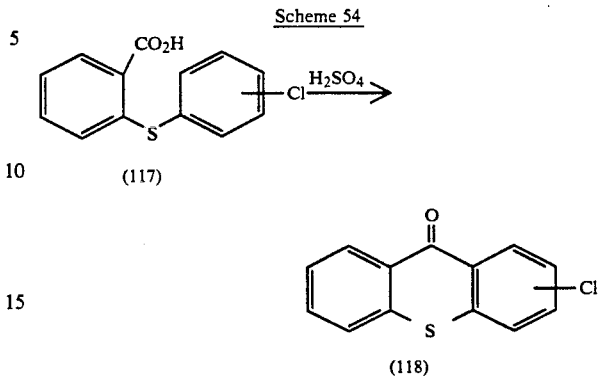

Nitrothioxanthones are prepared in the same manner (*J. Am. Chem. Soc.*, 69 1925, 1928 [1947]).

Similarly, amino-thioxanthones (120) can be reduced to aminoxanthenes (121). Aminothioxanthones (120) are prepared by cyclization of aminodiphenylsulfide-2-carboxylic acids (119) (Scheme 55) (*Ber.* 42, 3065). They are converted to acetamido derivatives by well-known methods (*Ber.*, 42, 3057).

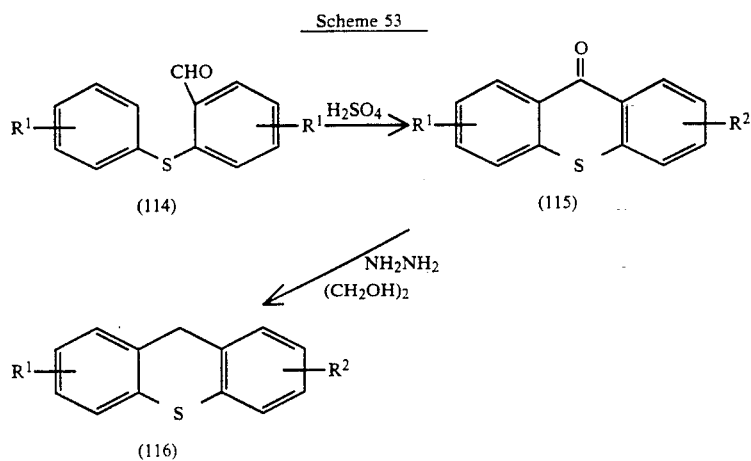

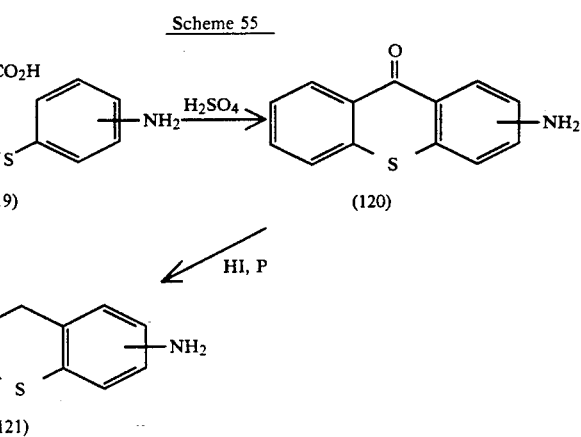

(*J. Chem. Soc.*, 747, 1941). Haloxanthones can be prepared by cyclizing phenylmercaptobenzoic acids (117)

Hydroxythioxanthones (123) are likewise prepared from S-hydroxy-substituted-phenylthiosalicyclic acids (122) with sulfuric acid (Scheme 56).

Scheme 56

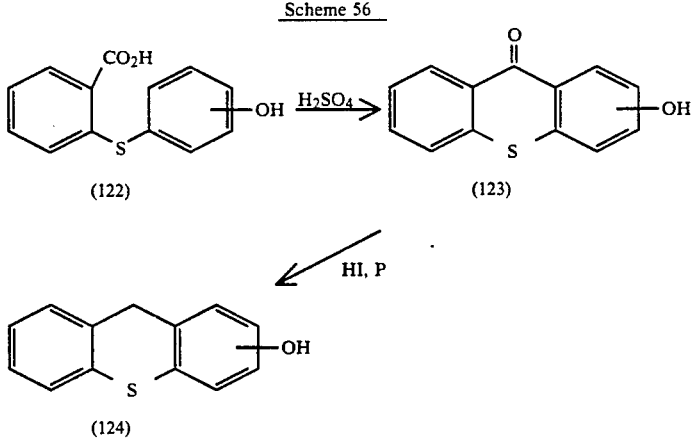

Alkoxy substituted thioxanthones are prepared in the same manner from S-alkoxy substituted phenylthiosalicylic acids (*J. Chem. Soc.*, 869 (1929). Thioxanthenes (124) are prepared by reducing thioxanthones with hydrogen iodide in the presence of red phosphorus.

Thioxanthon-S.S-dioxides (126) are prepared as above by cyclization of diphenylsulfoncarboxylic acids (125) (Scheme 57) or by oxidation (Scheme 58) of the thioxanthone with hydrogen peroxide, or metachloroperbenzoic acid.

Scheme 57

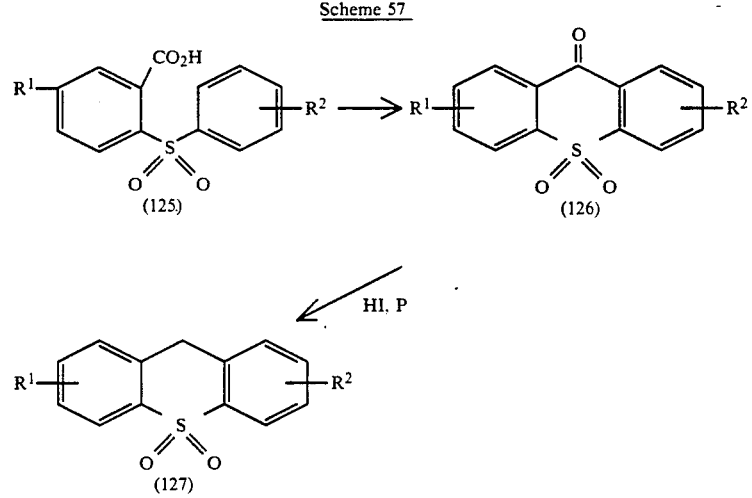

Scheme 58

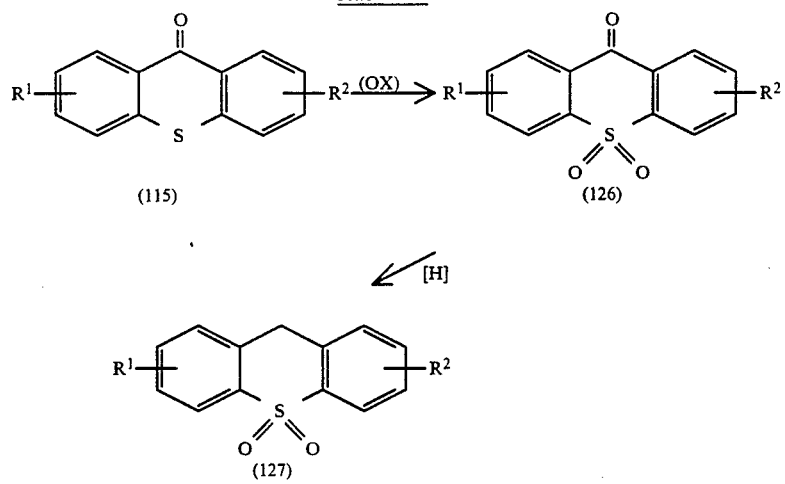

The carbonyl in (126) is then reduced by hydriodic acid in the presence of red phosphorus as described above to the thioxanthen-S,S-dioxide. Also, the thioxanthene (116) may be oxidized to the thioxanthen-S-oxide (128) (Scheme 59).

Scheme 59

(116)

(128)

Dibenzosuberenes (130) are prepared by oxidative cyclization of the bis-Wittig reagent (129) prepared from the corresponding dibromide (Scheme 60) (*Angew. Chem.*, 76 226 [1964]; Ber., 99 2848 [1966]). Catalytic hydrogenation of (130) yields dibenzosuberane (131).

Scheme 60

(129)

(130)

(131)

9,10-Dihydroacridines (133) are prepared by reduction of acridines (132) with sodium amalgam in alcohol, or zinc in hydrochloric acid (Scheme 61).

Scheme 61

(132)

-continued
Scheme 61

(133)

(*Annalen*, 158 278; Ber., 16 1818, 1972). 9,10-Dihydroacridines are also prepared by the reduction of 9,10-dihydro-9-acridones with sodium in alcohol, (Ber. 40 2521), or by reduction of the quaternary acridinium halide (Ber., 35 2536).

Substituted acridines (132) can be prepared by reacting a 2-halo-benzaldehyde (134) with substituted anilines (135) (Scheme 62) (Ber. 50 1312, 52 1648). Substituted 9,10-dihydroacridines are described: (*Ber.*, 62, 4161 *Annalen*, 463 301; *J. Chem. Soc.*, 125 1775; *J. Am. Chem. Soc.*, 49 1051, 1052).

Scheme 62

(134) + (135) $\xrightarrow{\text{1. Na}_2\text{CO}_3, \text{Cu}}{\text{2. H}_2\text{SO}_4}$ (132)

Acridones (137) can be prepared by cyclizing substituted-diphenylamine-2-carboxylic acids (136) with sulfuric acid or phosphorus pentachloride (Scheme 63) (Annalen, 355 345, 346, 344, 371).

Scheme 63

(136) $\xrightarrow{\text{H}^+}$ (137)

Heteroderivatives of fluorene, such as azafluorenes and diazafluorenes are alkylated under similar conditions as fluorene and substituted-fluorenes, (Schemes 64 and 65)

Scheme 64

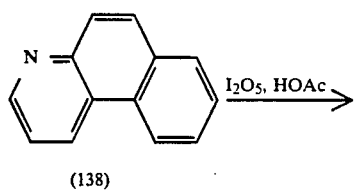

(138)

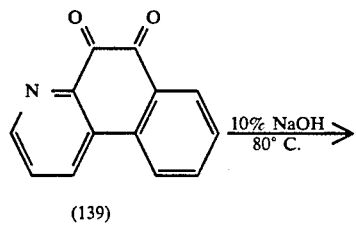

(139)

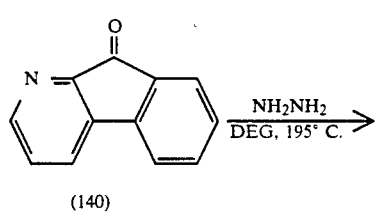

(140)

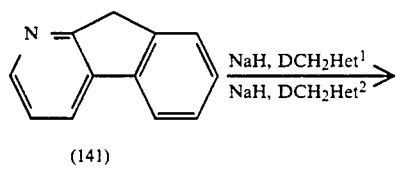

(141)

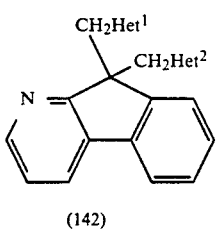

(142)

Scheme 65

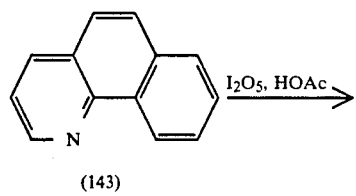

(143)

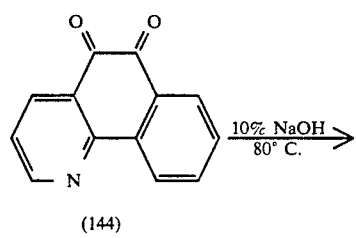

(144)

-continued
Scheme 65

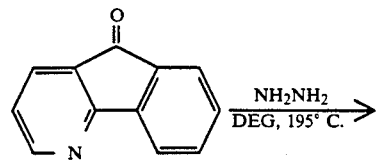

(145)

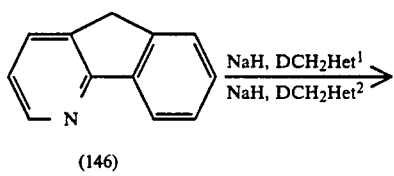

(146)

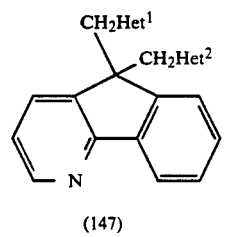

(147)

Monoazafluorenes are generally prepared from the commercially available 4-azaphenanthrene (138) or 1-azaphenanthrene (143). These are oxidized with iodine pentoxide in acetic acid (glacial) to yield the corresponding 4- and 1-azaphenanthren-5,6-dione (139,144). Basic rearrangement of these 5,6-diones with sodium hydroxide solutions in water yield the corresponding 1-azafluorenone (140) and 4-azafluorenone (145). Reduction with hydrazine in diethyleneglycol at 180°–225° occurs rapidly to produce the desired 1-azafluorene (141) and 4-azafluorene (146). Alkylation produces the target compound (147).

Syntheses of monoazafluorenes are described by: K. Kloc, et al., *J. Fur. Prakt. Chem.*, 319, 959-967 (1977); L. J. Henderson, Jr., et al., *J. Amer. Chem. Soc.*, 106, 5876-5879 (1984); K. Kloc, et. al., *Heterocycles*, 9, 849-852 (1978); J. Mtochonski and Z. Szule, *Polish J. Chem.*, 57, 33-39 (1983).

Diazafluorenes are generally prepared from phenanthrolines, which are most often prepared by a double Skraup synthesis or by an oxidative photocyclization of a diazastilbene.

In a Skraup synthesis, a phenylene diamine (148) or a nitroaniline is reacted with glycerine (149) and sulfuric acid or arsenic acid and an oxidizing agent, such as m-nitrobenzene sulfonic acid (Scheme 66).

Scheme 66

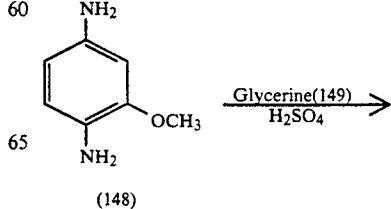

(148)

Scheme 66 -continued

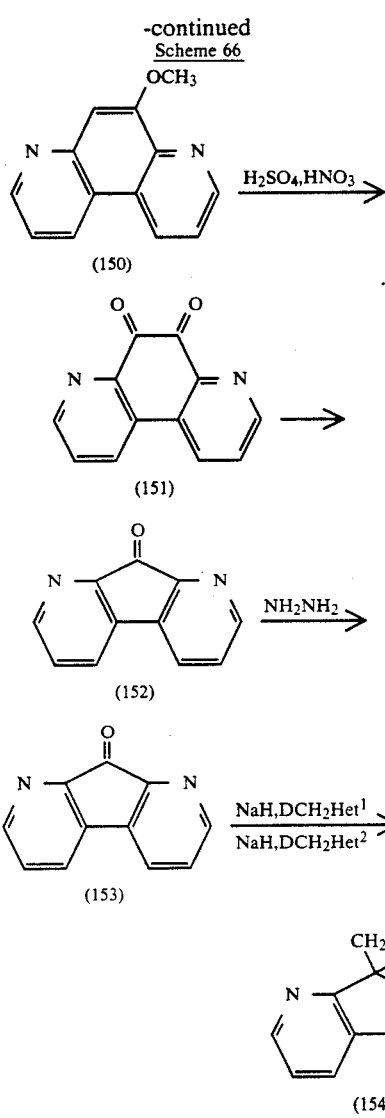

An intermediate amino- or nitro-quinoline or isoquinoline is produced. In the case of the amino-quinoline, it is not isolated, as it reacts immediately with excess reagents to yield the phenanthroline. If a nitro-aniline has been used to produce a nitroquinoline, it is isolated and purified if necessary. This often removes large amounts of tars produced by the Skraup synthesis. The nitro group is then reduced by standard conditions to yield an aminoquinoline. The aminoquinoline is then subjected to another Skraup reaction (sulfuric or arsenic acid, or both, glycerine and m-nitrobenzenesulfonic acid) to yield the phenanthroline.

Some phenanthrolines are very reluctant to undergo the usual basic oxidative rearrangement to the corresponding diazafluorenone. This is true of 4,7-phenanthroline, for instance. In this case, one uses 2-methoxyparaphenylenediamine in a double Skraup synthesis to produce the enoether, 5-methoxy-4,7-phenanthroline (150). Reaction of it with concentrated sulfuric acid and fuming nitric acid yields 4,7-phenanthrolin-5,6-quinone (151). The quinone undergoes oxidative rearrangement to produce 1,8-diazafluoren-9-one (152). Hydrazine reduction produces 1,8-diazafluorene (153) which is alkylated to the target compound, 9,9-bis(4-pyridinylmethyl)-1,8-diazafluorene (154). Other diazafluorenes produced by this method include 1,5-diazafluorene, (Scheme 67, 157), 1,6-diazafluorene, 2,5-diazafluorene, 3,5-diazafluorene, and 4,5-diazafluorene. See references for Scheme 64 and: French patent 1,382,542; French patent 1,369,626, U.S. Pat. No. 2,640,830, Swiss patent 275,433.

Scheme 67

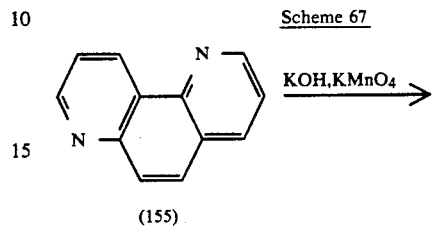

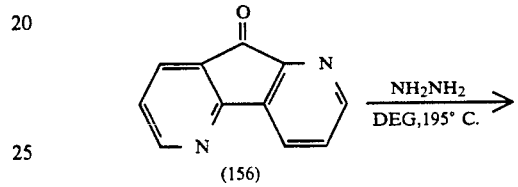

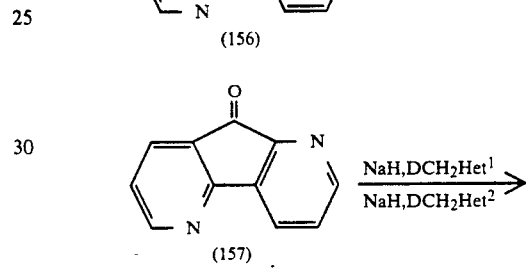

Phenanthrolines may also be prepared by an oxidative photocyclization of diazastilbenes (Scheme 68).

Scheme 68

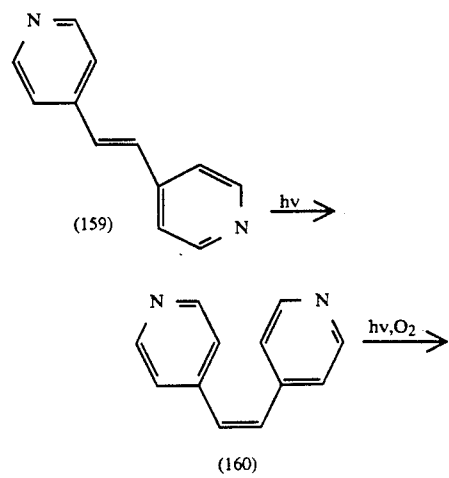

Scheme 68

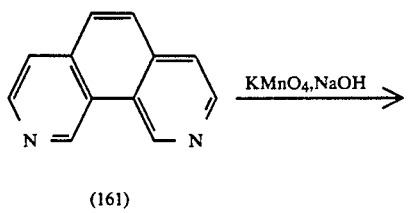

(161) →KMnO4,NaOH→

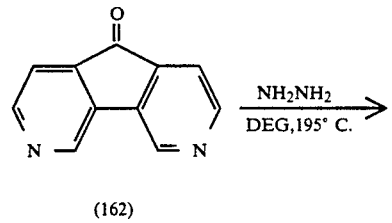

(162) →NH2NH2, DEG,195° C.→

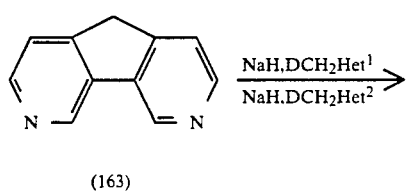

(163) →NaH,DCH2Het¹ / NaH,DCH2Het²→

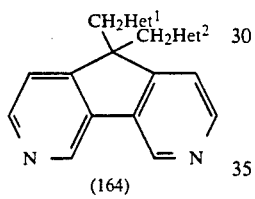

(164)

Scheme 69

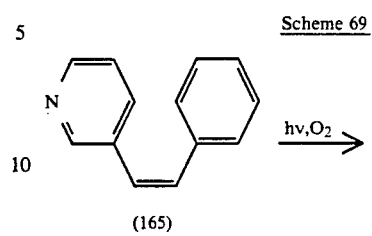

(165) →hv,O2→

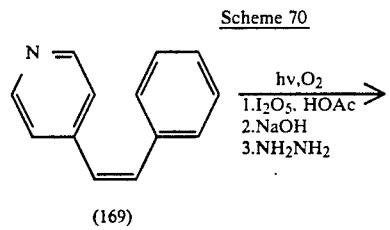

(166) 
1. I2O5,HOAc
2. NaOH
3. NH2NH2
→

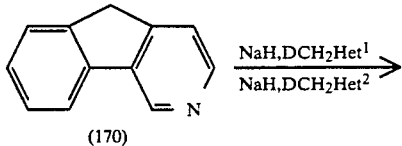

(167) →NaH,DCH2Het¹ / NaH,DCH2Het²→

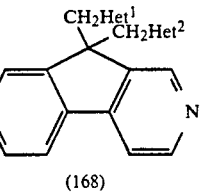

(168)

Commercially available trans-1,2-di(4-pyridinyl)ethene (159) in the presence of medium pressure ultraviolet light (200 watts to 1200 watts) isomerizes to the cis-isomer which, in the same reactor absorbs another photon producing dihydro-2,9-phenanthroline (161). In the presence of air, the material is quickly oxidized to 2,9-phenanthroline. Oxidative rearrangement in the presence of base yields 3,6-diazafluoren-9-one (162). Hydrazine reduces it to 3,6-diazafluorene (163). Alkylation by the usual methods described above yield the target 5,5-Bis(4-pyridinylmethyl)cyclopenta[2,1-c:3,4-c']dipyridine (164). Pertinent references are the following: *J. Org. Chem.*, 52 3975–79 (1987); *Ann.*, 696 1–14 (1966) for the preparation of phenanthrolines, which when rearranged to diazafluorenes yield the following: 1,8-diazafluorene; 1,5-; 1,7-; 1,6-; 2,7-; 2,5-; 4,5-; 2,6-; 3,5-; and 3,6-diazafluorenes.

The preparation of 2-azafluorene begins with the photocyclization of 3-styrylpyridine (165) to the 3-azaphenanthrene (166) described by G. Galiazzu, et al., *Tet. Letters*, 3717 (1966) and also *Organic Reactions*, 30, Chapter 1, Photocyclization of stilbenes and related molecules, by Mallory and Mallory, pp. 1–456 (1984), John Wiley & Sons, and references cited therein for preparation of azastilebenes. The 3-azaphenanthrene (165) is then oxidized as described above with iodine pentoxide in acetic acid to yield the 5,6-quinone. This is rearranged with sodium hydroxide solution to 2-azafluorenone. Hydrazine in diethyleneglycol yields the desired 2-azafluorene (167), which is alkylated with picolylchloride to produce the target compound, 9,9-bis(4-pyridinylmethyl)-2-azafluorene (168) (Scheme 69).

Following the photocyclization conditions described above, 4-styrylpyridine (169) may be converted to 3-azafluorene (170) and alkylated to yield the target 9,9-bis(4-pyridinylmethyl)-3-azafluorene (171) (Scheme 70).

Scheme 70

(169)
→hv,O2
1.I2O5, HOAc
2.NaOH
3.NH2NH2
→

(170) →NaH,DCH2Het¹ / NaH,DCH2Het²→

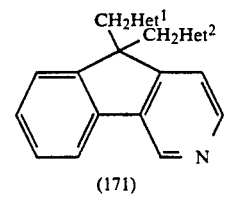

(171)

The nitrogen in the above diazastilbenes and monoazastilbenes may be replaced with other heteroatoms and heterocycles to yield targets as shown in Scheme 71.

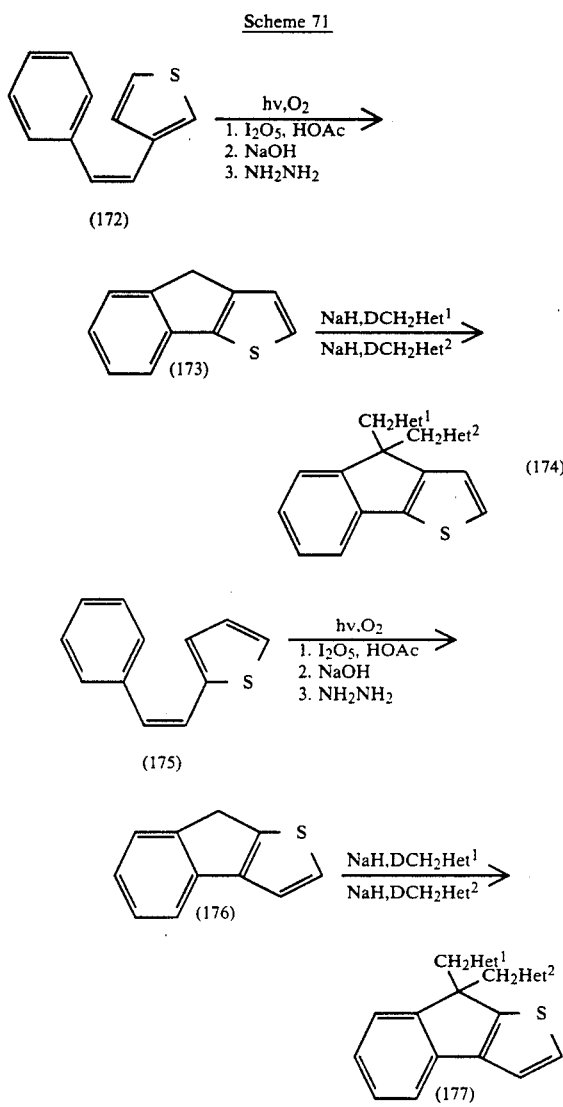

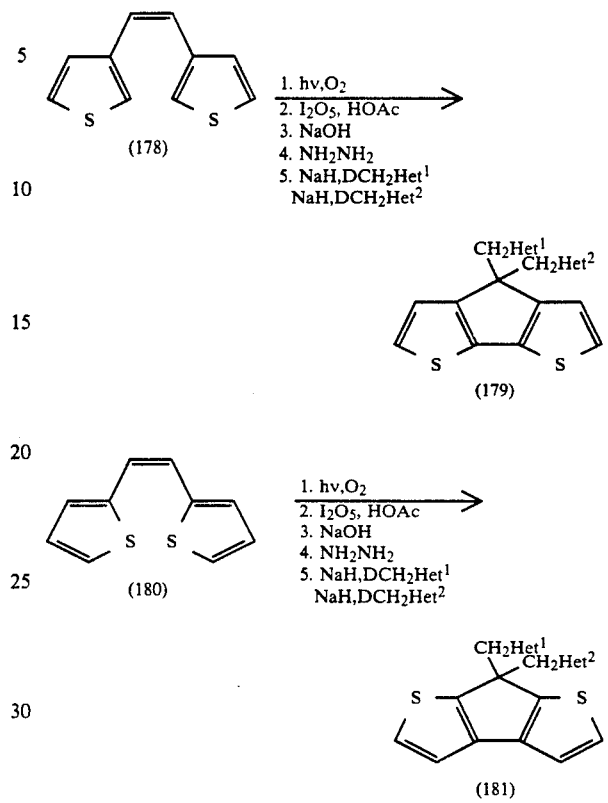

For instance, 3-styrylthiophene (172) yields a photocyclization product (*J. Chem. Soc. C*, 2504 (1970) which may be converted by the methods described above to 4H-indeno[1,2-b]thiophene (173). Likewise, 2-styrylthiophene (175) is converted by photocyclization [*J. Chem. Soc.*, 6221 (1965)] to an intermediate that will yield 8H-indeno[2,1-b]thiophene (176). These may then be alkylated by picolyl chloride to yield 4,4-bis(4-pyridinylmethyl)indeno[1,2,-b]thiophene (174) and 8,8-bis(4-pyridinylmethyl)indeno[2,1-b]thiophene (177). Also, the furan derivatives are available via this route (Z. Naturfursch., Teil B, 24 (1969).

In the same manner, Scheme 72 shows the conversion of 1,2-di(3-thienyl)ethylene (178) to 4,4-bis(4-pyridinylmethyl)cyclopenta[2,1-b:3,4-b']dithiophene (179) and the 2-isomer (180) to 7,7-bis(4-pyridinylmethyl)cyclopenta[1,2-b:4,3-b']dithiophene (181). The corresponding furans produce 4,4-bis(4-pyridinylmethyl)cyclopenta[2,1-b:3,4-b']difuran and 7,7-bis(4-pyridinylmethyl)cyclopenta[1,2-b:4,3-b']-difuran.

The heterocyclic compounds D—$CH_2$—Het used as intermediates in the processes described above are available commercially or by methods described in standard works on heterocyclic chemistry such as Katritzky and Rees, *Comprehensive Heterocyclic Chemistry*, Vols. 2-5, Pergamon Press, N. Y., 1984. In some instances the preparation of the corresponding hydroxy compounds (D=OH) is described in the literature; these can be converted to the corresponding halo compounds (e.g. D=Br) by mild reagents such as triphenylphosphine with carbon tetrabromide. Alternatively, the hydroxy compounds can be converted to the corresponding sulfonate esters (e.g. D=$CH_3SO_2O$) by reaction with the corresponding sulfonylchloride in the presence of a base such as pyridine or triethylamine. In some cases, the methyl substituted heterocycles $CH_3$—Het can be converted directly into the halo compounds (D=Cl or Br) with a halogenating reagent such as N-bromosuccinimide or N-chlorosuccinimide. Specifically, the following heterocyclic compounds were prepared by the methods described in the literature references given: 2-chloromethylpyrazine, Newkome, et. al., *Synthesis*, 676 (1984); 4-bromomethylpyrimidine, Lombardino, et. al., U.S. Pat. No. 4,426,263 and Brown, et. al., *Aust. J. Chem.*, 27, 2251 (1974); 4-chloromethylpyridazine, Heinisch, *Monatsh. Chem.*, 104, 1354 (1973); 1-benzyl-4-hydroxymethylpyrazole, Stein, U.S. Pat. No. 4,151,293.

The compounds useful in the present invention can be used as their free base or their pharmaceutically suitable salts. Salt formation is well known to those skilled in the art.

The invention can be further understood by the following examples in which parts and percentages are by weight unless otherwise indicated; all temperatures are in degrees centigrade.

EXAMPLE 1

3,3-Bis(2-pyridylmethyl)-1-phenylindolin-2-one

To a solution of 0.1 mole of N-phenylindolin-2-one in 200 ml of benzene under $N_2$ was rapidly added 0.1 mole of thallium ethoxide. The solution was heated briefly to boiling. At about 50°, a heavy precipitate started to form. After refluxing for 5 minutes, the mixture was cooled and 200-300 ml of hexane was added to complete precipitation. The solid was filtered off and dried to yield 85% of the thallium salt of N-phenylindolin-2-one as a yellow solid.

0.22 Mole of picolylchloride hydrochloride was carefully converted to the free base by dissolving in 30 ml cold water, cooling to 0°-5° and basifying with ammonium hydroxide. The free base was extracted out ($3 \times 100$ ml benzene), dried with $Na_2SO_4$ and filtered, while maintaining the temperature no higher than 10°.

To this solution was added the thallium salt of the N-phenylindolin-2-one, followed by 200 ml benzene. This mixture was refluxed overnight and after cooling, the precipitated thallium chloride was filtered off. The basic product was extracted out of the filtrate with 0.5N hydrochloric acid and was then reconverted to the base with ammonium hydroxide and extracted into methylene chloride, dried with anhydrous potassium carbonate, filtered and evaporated. The remaining thick dark red oil was dissolved in 50 ml ether and trituration with a glass rod started crystallization, which was complete in a short while. The solid was filtered off, washed with ether and dried to yield 11.2 g of product; m.p. 107°-111°. The product was purified by flash chromatography using 40-60 micron silica gel 60 (E. Merck) on a column 10" long $\times$ 2" in diameter. Elution with 95:5 methylene chloride-methanol (detection with a 256 m m Gow-Mac detector) afforded 8.2 g of pure free base in fractions 5 through 10 (100 ml each), $R_f$ 0.33 (silica gel; 95:5 methylene chloride/methanol); m.p. 129°-130°.

Anal. Calcd. for $C_{26}H_{21}N_3O$: C, 79.77; H, 5.41; N, 10.73. Found C, 80.05; H, 5.65; N, 10.67.

EXAMPLE 2

3,3-Bis(2-pyridylmethyl)-1-phenylindolin-2-one dihydrochloride 8.2 g of 3,3-Bis(2-pyridylmethyl)-1-phenylindolin-2-one was converted to the dihydrochloride salt by dissolving it in 25 ml methylene chloride and adding 25 ml of 25% hydrochloric acid in ethanol. The solution was evaporated and the glassy residue was dissolved in 75 ml boiling acetone. Cooling to room temperature and trituration started crystallization. After sitting at room temperature for 6 hours, the mixture was kept at 0° overnight. The product was then filtered, washed with cold acetone and dried in a vacuum oven for 1 hour at 60° over Granusic to yield 8.55 g; m.p. 250°-251°. The product was recrystallized from isopropanol affording 8.29 g; m.p. 250°-251°.

EXAMPLE 3

3,3-Bis(3-pyridylmethyl)-1-phenylindolin-2-one dihydrochloride

To 0.3 mole of N-phenylindolinone in 300 ml of benzene was added 0.36 mole of sodamide in one batch. The mixture was refluxed for 3 hours (until ammonia evolution ceases), and the reaction was then cooled to room temperature. 0.5 Mole of 3-picolylchloride was carefully prepared from the hydrochloride salt in the same manner previously described for 2-picolylchloride and was then extracted into benzene, dried with sodium sulfate and filtered. This benzene solution of 3-picolylchloride was added dropwise with vigorous mechanical stirring to the N-phenylindolinone anion solution under nitrogen over a period of 30 minutes at 20°. After completion of addition, the reaction was refluxed for an additional 3 hours.

The reaction mixture was cooled to room temperature and a second portion of 0.36 mole of sodamide was added in one batch. As above, the mixture was refluxed until ammonia evolution from the reaction ceased (3 hours).

The reaction mixture was cooled to room temperature and an additional 0.5 mole of 3-picolylchloride base in benzene was added dropwise with vigorous stirring to the indolinone anion solution over a period of 30 minutes at 20°. After completion of addition of the 3-picolylchloride, the reaction mixture was refluxed 3 hours. The reaction mixture was then cooled in an ice bath and 1N HCl was added (300 ml) in conjunction with vigorous mechanical stirring. The HCl phase was separated and the organic phase was extracted twice more with 100 ml of 1N HCl. The combined acid extracts were made basic, extracted with methylene chloride, washed with water, dried with sodium sulfate, filtered and evaporated. The dark oil was triturated with ether to yield a crop of dense crystals, which were filtered, washed with ether until the washings were colorless, to afford 3.1 g of solid; m.p. 136.5°-138°. A portion (2.8 g) was dissolved in 10 ml of 25% hydrochloric acid in ethanol. Scratching started crystallization (dense crystals). After one hour at 0°, the white crystals were filtered off and dried to yield 3.2 g of the title compound; m.p. 156°. The product was dissolved in 115 ml boiling ethanol, to which 10 ml of boiling acetone was carefully added. The solution was allowed to cool undisturbed for 8 hours, then overnight at 0°. The pure white crystals were filtered, washed with cold 1:1 ethanol-acetone and dried under infrared lamps, to afford 2.6 g of pure product; m.p. 156°-156.5°.

EXAMPLE 4

Method A 3,3-Bis(4-pyridylmethyl)-1-phenylindolin-2-one dihydrochloride

N-phenylindolinone (0.05 mole) was dissolved in the minimum amount of dry tetrahydrofuran in a multineck flask under $N_2$. Lithium diisopropylamide (0.05 mole) was weighed out in a dry box into a dropping funnel and then dry tetrahydrofuran was added to the lithium diisopropylamide to dissolve it. The dropping funnel containing the lithium diisopropylamide-tetrahydrofuran solution was sealed and removed from the dry box. The indolinone solution was cooled to $-30°$ and the lithium diisopropylamide solution was added to it dropwise at $-30°$ over a period of 15 minutes. After the addition, the reaction was allowed to warm to room temperature. The reaction mixture was again cooled to $-30°$ and 4-picolylchloride (0.06 mole), which had been converted to the free base as previously described and then dissolved in 25 ml tetrahydrofuran, was added dropwise during 30 minutes at $-30°$.

After completion of addition, the reaction was allowed to warm to room temperature for 30 minutes. It was then cooled to −30° and the second portion of lithium diisopropylamide (0.05 mole) in tetrahydrofuran was added dropwise over a period of 15 minutes at −30°. After completion of addition, the reaction mixture was allowed to warm to room temperature as a second batch of 4-picolylchloride hydrochloride (0.06 mole) was converted to the free base.

The room temperature anion reaction mixture was again cooled to −30° and the second portion of 4-picolylchloride in 25 ml tetrahydrofuran was added dropwise over a period of 30 minutes at −30°. The reaction mixture was brought to room temperature and maintained at room temperature for 1-17 hours depending on convenience. Any remaining anion was destroyed by carefully adding 50 ml saturated ammonium chloride solution. The tetrahydrofuran was then evaporated and the residue was dissolved in methylene chloride and extracted out of the methylene chloride with 3×100 ml portions of 0.5N hydrochloric acid. The combined HCl portions were made basic (pH=12) and product extracted with (3×100 ml) methylene chloride. The methylene chloride was dried with sodium sulfate, filtered and evaporated to yield 20 g of product. Purification by chromatography in 10 g batches (40-63 mm silica gel on a column 8" long×2" diameter; eluting with: EtOAc 69.46%, Hexane 29.75%, and Et₃N 0.79%) gave 19.2 g of the base (93%); m.p. 186.0°-186.5°.

3,3-Bis(4-pyridylmethyl)-1-phenylindolin-2-one (19 g) was converted to the dihydrochloride by treatment with 40 ml 25% hydrochloric acid in ethanol. To the mixture was added 50 ml isopropanol and the solution was heated to boiling. Boiling acetone was added until thick needles just started to form (total volume of solvents: 200-250 ml). The solution was allowed to cool to room temperature, then allowed to stand overnight at 0°. The solid was filtered and washed with cold isopropanol to yield 19.5 g (84%) of the title compound; m.p. 257°-8°. (Note: degree of drying has an effect on m.p. of the dihydrochloride; very slowly increasing the temperature of the melting point apparatus gives a melting point of 275°-276°). A second crop was obtained by evaporating the filtrate, dissolving the residue in isopropanol and adding approximately an equal volume of acetone; the mixture was allowed to sit overnight at room temperature, and then 6 hours at 0° to yield an additional 2.8 g, m.p. 252°-253°. Recrystallization yielded 2.4 g, of the second crop: m.p. 257°-258°. The total dihydrochloride yield was 21.9 g (94%).

EXAMPLE 4

Method B (Preferred)

Part A:
3-(4-Pyridinylmethylidene)-1-phenylindolin-2-one

A solution of oxalyl chloride (175 mL, 254.6 g, 2.01M) was cooled to 5°, and a solution of diphenylamine (320 g, 1.89M) and toluene (580 mL) added over 8 minutes. The mixture was heated to 50°-65° for 74 minutes. The mixture was then heated to 125° to distill toluene and excess oxalyl chloride; total distillate collected was 630 mL. The solution was then refluxed at 125°±2° for 20 hours. The mixture was cooled to 104°, and a solution of 4-picoline (215 mL, 205.7 g, 2.21M) in acetic acid (750 mL) was added over 17 minutes. The mixture was heated to 130° to remove excess toluene via acetic acid/toluene azeotrope. Additional acetic acid (750 mL) was added during the distillation. A total of 875 mL distillate containing 260 mL toluene was collected. The mixture was cooled to 115°, and acetic anhydride (360 mL, 389.5 g, 3.81M) added over 10 minutes while heating to 120°-130°. The mixture stirred at 120°±2° for 1.75 hours, and then cooled to 76°. Water (530 mL) was added over 7 minutes followed by isopropanol (430 mL) while maintaining the temperature between 82° and 63°. The mixture was cooled to ambient temperature overnight, then to 0°-5°. The crude product was collected by filtration, washed with isopropanol (2.16 l) and water 1.64 l). Drying in a vacuum oven at 80°-90° yielded the title compound (422.6 g, 75%) as an orange crystalline solid. m.p.: 160.1°-161.9°.

Part B:
3,3-bis(4-pyridinylmethyl)-1-phenylindolin-2-one

A slurry of 3-(4-pyridinylmethylidene)-1-phenylindolin-2-one (80 g, 0.268M) and methanol (600 mL) was cooled to 6°. Sodium borohydride pellets (0.2 g each, 3.19 g total 0.084M) were added over 20 minutes with gentle cooling. The mixture was stirred for 50 minutes, cooled to 7°, and 10N sodium hydroxide (64 mL, 0.64M) added over 11 minutes. A solution of 4-picolychloride hydrochloride (4.85 g, 0.296M) and water (160 mL) was then added over 28 minutes while maintaining a temperature of 10°-15°. Cooling was then removed, and 10N sodium hydroxide (80 mL, 0.8M) added over 10 minutes. The mixture was stirred for 2 hours and then water (580 mL) added over 45 minutes. The slurry was cooled to 10°-15°, stirred for 10 minutes, and the solids collected by filtration. The solids were then reslurried in water (450 mL), filtered, and washed with water. Drying in a vacuum oven at 85°-95° yielded 89.4 g (85%) crude title compound. Eighty-five grams of this crude product was recrystallized in isopropanol and water to yield 77.3 g of the title compound (90% recovery), m.p. 186°-188°.

EXAMPLE 5

3,3-Bis(4-pyridylmethyl)-1-methylindolin-2-one dihydrochloride

To a solution of 0.05 mole of 1-methylindolin-2-one in 50 ml of tetrahydrofuran cooled to −30° was added 0.1 mole of lithium diisopropylamide in 100 ml of tetrahydrofuran in a dropwise fashion over 30 minutes. The reaction mixture was allowed to warm to room temperature after completion of addition, and was then cooled back down to −30°. Following the careful conditions described previously for the conversion of picolylchloride hydrochloride to picolylchloride base, 0.21 mole of 4-picolylchloride hydrochloride was converted to the anhydrous free base and was then dissolved in tetrahydrofuran (150 ml). This solution was added dropwise during 60 minutes at −30° to the reaction mixture.

After completion of addition, the reaction mixture was allowed to warm to room temperature for one hour, then was cooled and carefully decomposed by the dropwise addition of saturated ammonium chloride.

When the addition was complete, the tetrahydrofuran was evaporated and the residue was partitioned between benzene and 0.5N HCl. This residue was transferred to a separatory funnel and the organic phase was extracted twice more with 0.5N HCl. The combined acid extracts were basified, extracted with benzene, dried with Na₂SO₄, filtered and evaporated. The residue was triturated with ether, filtered and washed with a small amount of ether to yield 2.9 g; m.p.

149.9°–150.9°. This product was converted to the dihydrochloride salt with 25% hydrochloric acid and ethanol and crystallized from ethanol-acetone to yield 1.9 g of the title compound, m.p. 274.5°.

EXAMPLE 6

3,3-Bis(4pyridylmethyl)-1-(3-chlorophenyl)indolin-2-one dihydrochloride

Using the procedure of Example 3, the title compound was prepared from N-(3-chlorophenyl)indolin-2-one in a yield of 24%, m.p. 275°–276°.

EXAMPLES 7 and 8

3,3-Bis(4-pyridylmethyl-1-oxido)-1-phenylindolin-2-one and
3-(4-pyridylmethyl)-3-(4-pyridylmethyloxido)-1-phenylindolin-2-one A solution of 4.14 g (0.024 mole) of 80–85% m-chloroperbenzoic acid in 50 ml methylene chloride was added dropwise with magnetic stirring to 3,3-bis(4-pyridylmethyl)-1-phenylindolin-2-one in 100 ml methylene chloride, and solution was stirred overnight. Checking for peroxide with moist starch iodide paper was negative, so the methylene chloride solution was washed with 3×75 ml 5% sodium bicarbonate, dried with sodium sulfate, filtered and evaporated.

The residue was triturated with 5:1 ether/ethyl acetate to yield 2.14 g of a solid containing the bis-N-oxide, the mono-N-oxide, and a small amount of starting material. The reaction mixture was purified by flash chromatography (silica gel, 40–63 mm, eluting with 90:10 chloroform/methanol) affording 1.18 g, of the major product, $R_f=0.34$; m.p. 265.3°–265.7° (after recrystallization from 10 ml water). The high resolution mass spectrum confirmed the major product as the bis N-oxide; m/e 423.1595 (M+, calcd. for $C_{26}H_{21}N_3O_3$ 423.1582).

A second fraction (200 mg) obtained from the flash chromatography was identified as the mono-N-oxide; 3-(4-pyridylmethyl)-3-(4-pyridylmethyloxido)-1-phenylindolin-2-one, $R_f=0.41$; m.p. 217.7°–218.5°.

Mass spectrum m/e 407.1631 (M+, calcd. for $C_{26}H_{21}N_3O_2$ 407.1634).

The compounds of Examples 1–8, and other compounds which can be prepared by such procedures and procedures described in the synthesis disclosure are illustrated by the structures represented in Table 1. This Table is intended to illustrate the invention, but not to limit its breadth.

TABLE 1
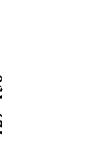
| Ex. No. | X | Y | R | V | W | p | —Het¹ | —Het² | Z | m.p. °C. |
|---|---|---|---|---|---|---|---|---|---|---|
| 1 | H | H |  | H | H | 0 |  |  | O | 129–130 |
| 2 | H | H | 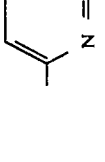 | H | H | 0 | 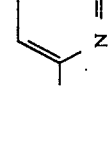 | 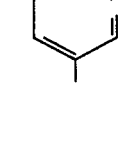 | O | 250–251 (2 HCl) |
| 3 | H | H | 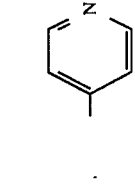 | H | H | 0 |  |  | O | 156–156.5 (2 HCl) 136.5–138 (free base) |
| 4 | H | H |  | H | H | 0 |  | 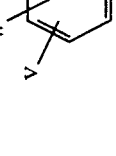 | O | 257–258 (2 HCl) 186–186.5 (free base) |
| 5 | H | H | CH₃ | — | — | 0 | 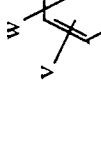 |  | O | 274–275 (2 HCl) 149.5–150.9 (free base) |
| 6 | H | H |  | 3-Cl | H | 0 |  | 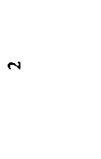 | O | 275–276 (2 HCl) |

TABLE 1-continued
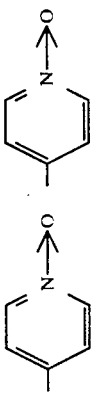
| Ex. No. | X | Y | R | V | W | p | —Het¹ | —Het² | Z | m.p. °C. |
|---|---|---|---|---|---|---|---|---|---|---|
| 7 | H | H | phenyl (V,W) | H | H | 0 | 4-methylpyridine N-oxide | 4-methylpyridine N-oxide | O | 265.3–265.7 |
| 8 | H | H | phenyl (V,W) | H | H | 0 | 4-methylpyridine | 4-methylpyridine N-oxide | O | 217.7–218.5 |
| 9 | H | H | pyridyl | — | — | 1 | 4-methylpyridine | 4-methylpyridine | O | 173–174 (3 HCl) |
| 10 | H | H | phenyl (V,W) | H | H | 0 | 2-methylpyridine N-oxide | 2-methylpyridine N-oxide | O | 196.1–196.7 |
| 11 | H | H | phenyl (V,W) | H | H | 0 | 3-methylpyridine N-oxide | 3-methylpyridine N-oxide | O | 201.7–202.0 |

TABLE 1-continued

| Ex. No. | X | Y | R | V | W | p | —Het¹ | —Het² | Z | m.p. °C. |
|---------|---|---|---|---|---|---|-------|-------|---|----------|
| 12 | H | H | phenyl (W,V substituted) | H | H | 0 | pyridine N-oxide (2-yl) | pyridin-2-yl | O | Amorphous |
| 13 | H | H | phenyl (W,V substituted) | H | H | 0 | pyridine N-oxide (3-yl) | pyridin-3-yl | O | Amorphous |
| 14 | H | H | phenyl (W,V substituted) | H | H | 0 | pyridin-4-yl | pyridin-4-yl | S | — |
| 15 | H | H | phenyl (W,V substituted) | H | H | 0 | 2-chloropyridin-5-yl | 2-chloropyridin-5-yl | O | 230.8–231.4 |
| 16 | H | H | CH₃CH₂CH₂— | — | — | 0 | pyridin-4-yl | pyridin-4-yl | O | 227–228 (2 MCl) |

TABLE 1-continued
| Ex. No. | X | Y | R | V | W | p | —Het¹ | —Het² | Z | m.p. °C. |
|---|---|---|---|---|---|---|---|---|---|---|
| 17 | H | H | 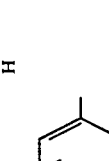 | H | H | 0 |  2-Cl pyridyl | 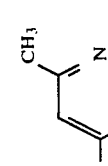 2-Cl pyridyl | O | |
| 18 | H | H | 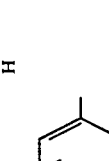 | H | H | 0 |  2-CH₃ pyridyl | 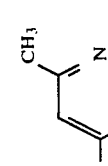 2-CH₃ pyridyl | O | |
| 19 | 6-CH₃ | H | 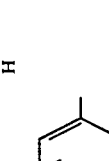 | H | H | 0 |  pyridyl | 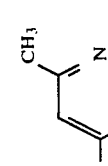 pyridyl | O | 217–219 |
| 20 | 6-OCH₃ | H | 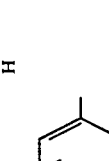 | H | H | 0 |  pyridyl | 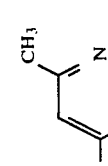 pyridyl | O | |
| 21 | 5-Cl | H | 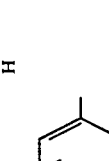 | H | H | 0 |  pyridyl | 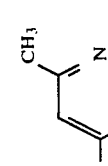 pyridyl | O | |

TABLE 1-continued
| Ex. No. | X | Y | R | V | W | p | —Het¹ | —Het² | Z | m.p. °C. |
|---|---|---|---|---|---|---|---|---|---|---|
| 22 | H | H | S— | — | — | 0 | 4-pyridyl | 4-pyridyl | O | |
| 23 | H | H | phenyl(V,W) | H | H | 1 | 4-pyridyl | 4-pyridyl | O | |
| 24 | H | H | C₂H₅ | — | — | 0 | 4-pyridyl | 4-pyridyl | O | |
| 25 | H | 7-NHC₃H₇ | phenyl(V,W) | H | H | 0 | 4-pyridyl | 4-pyridyl | O | |
| 26 | H | H | phenyl(V,W) | H | H | 0 | 2-pyridyl | 2-pyridyl | S | |
| 27 | H | H | phenyl(V,W) | 4-OCH₃ | 3-OCH₃ | 0 | 2-pyridyl | 2-pyridyl | O | |

TABLE 1-continued structure: phenyl with X, Y substituents; CH(CH₂-Het¹)(CH₂-Het²)-N(R)(CH₂)ₚ with Z

| Ex. No. | X | Y | R | V | W | p | —Het¹ | —Het² | Z | m.p. °C. |
|---|---|---|---|---|---|---|---|---|---|---|
| 28 | 5-OCH₃ | 6-OCH₃ | phenyl(V,W) | H | H | 0 | 2-pyridyl | 2-pyridyl | O | |
| 29 | H | H | phenyl(V,W) | 3-Cl | 4-Cl | 1 | 4-pyridyl | 4-pyridyl | O | |
| 30 | H | H | 3-pyridyl | — | — | 1 | 4-pyridyl | 4-pyridyl | O | |
| 31 | H | H | phenyl(V,W) | 2-NO₂ | H | 0 | 4-pyridyl | 4-pyridyl | O | |
| 32 | H | H | n-C₁₀H₂₁ | — | — | 1 | 4-pyridyl | 4-pyridyl | O | |
| 33 | 5-CH₃ | 4-CH₃ | phenyl(V,W) | H | H | 0 | 4-pyridyl | 4-pyridyl | S | |

TABLE 1-continued
| Ex. No. | X | Y | R | V | W | p | —Het¹ | —Het² | Z | m.p. °C. |
|---|---|---|---|---|---|---|---|---|---|---|
| 34 | 4-NO₂ | H | cyclooctyl | — | — | 1 | 4-pyridyl | 2-pyridyl | O | |
| 35 | 4-N(CH₃)₂ | H | phenyl(V,W) | H | 4-CF₃ | 0 | 4-pyridyl | 3-pyridyl | O | |
| 36 | H | H | phenyl(V,W) | H | 4-CN | 0 | 4-pyridyl | 4-pyridyl | O | |
| 37 | H | H | phenyl(V,W) | H | 4-CF₃ | 1 | 4-pyridyl | 3-pyridyl | O | |
| 38 | H | H | phenyl(V,W) | H | 3-N(C₂H₅)₁ | 0 | 4-pyridyl | 4-pyridyl | O | |

TABLE 1-continued
| Ex. No. | X | Y | R | V | W | p | —Het¹ | —Het² | Z | m.p. °C. |
|---|---|---|---|---|---|---|---|---|---|---|
| 39 | H | H |  | H | H | 0 | 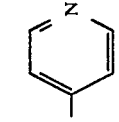 | 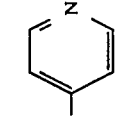 | S | |
| 40 | H | H |  | 3-Cl | 4-Cl | 0 |  | 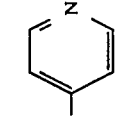 | O | |
| 41 | H | 4-CF₃ | 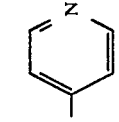 | H | H | 0 |  |  | O | |
| 42 | 5-N(CH₃)(C₂H₅) | H |  | — | — | 1 | 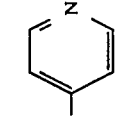 |  | O | |
| 43 | H | H |  | H | H | 0 | 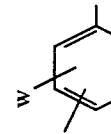 |  | O | 167.5-169 |
| 44 | H | H |  | 3-NO₂ | H | 0 |  |  | S | |

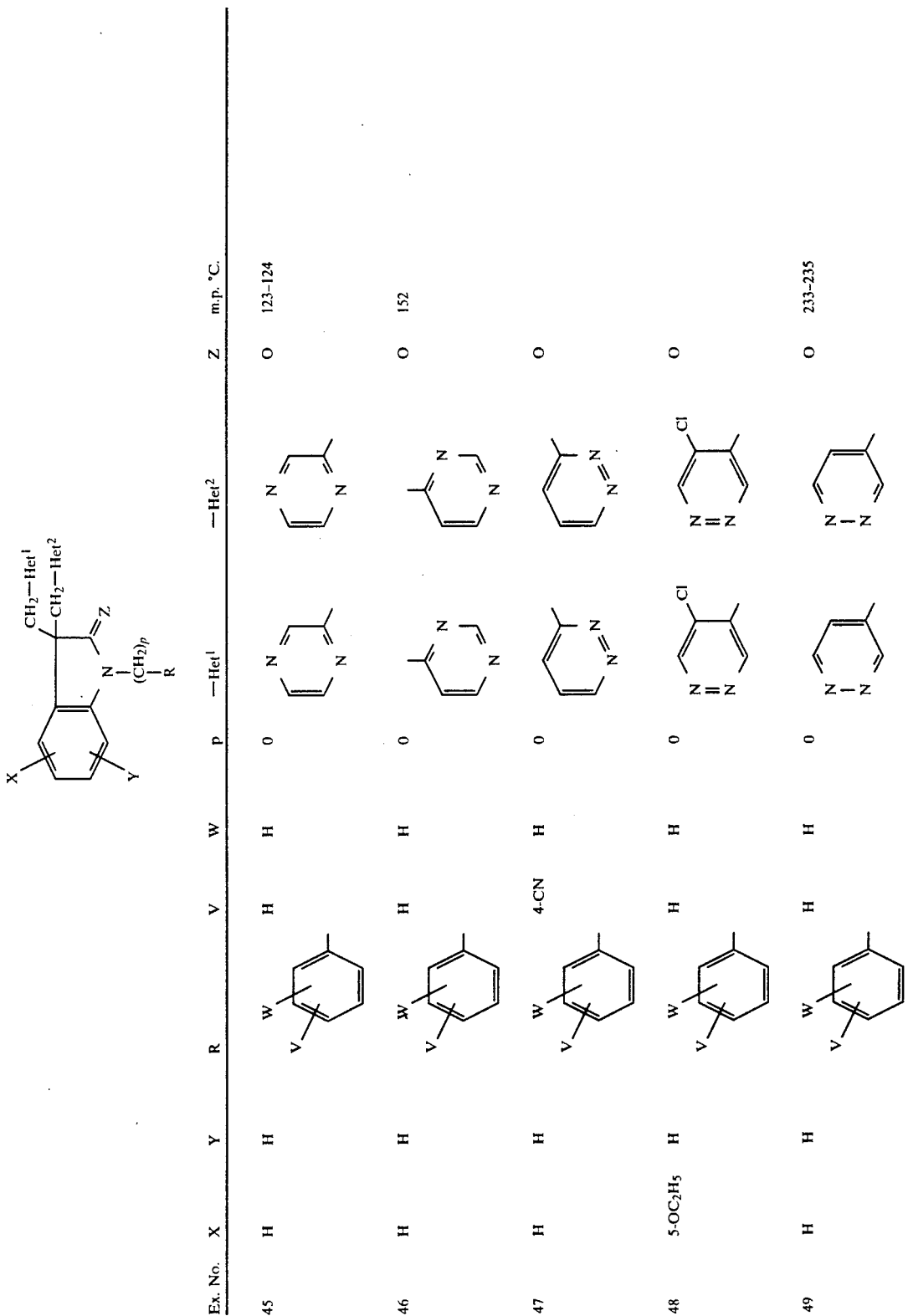

TABLE 1-continued

| Ex. No. | X | Y | R | V | W | p | —Het¹ | —Het² | Z | m.p. °C. |
|---|---|---|---|---|---|---|---|---|---|---|
| 50 | H | H | phenyl(V,W) | H | H | 0 | 4-amino-pyrimidinyl | 4-amino-pyrimidinyl | O | |
| 51 | H | H | phenyl(V,W) | H | H | 0 | 5-methyl-pyrimidinyl | 5-methyl-pyrimidinyl | O | |
| 52 | H | H | phenyl(V,W) | H | H | 0 | 4-chloro-6-methyl-pyridazinyl | 4-chloro-6-methyl-pyridazinyl | O | |
| 53 | H | H | phenyl(V,W) | H | H | 0 | 4-methoxy-6-methyl-pyridazinyl | 4-methoxy-6-methyl-pyridazinyl | O | |
| 54 | H | H | phenyl(V,W) | H | H | 0 | 4-methyl-pyridyl | 4-methyl-pyrimidinyl | O | 131-133 |

TABLE 1-continued
| Ex. No. | X | Y | R | V | W | p | —Het¹ | —Het² | Z | m.p. °C. |
|---|---|---|---|---|---|---|---|---|---|---|
| 55 | H | H |  | H | H | 0 |  |  | O | |
| 56 | H | H |  | H | H | 0 |  |  | O | |
| 57 | H | H |  | H | H | 0 |  |  | O | |
| 58 | H | H |  | H | H | 0 |  |  | O | |
| 59 | H | H |  | H | H | 0 |  |  | O | |
| 60 | H | H |  | — | — | 1 |  | | O | |

EXAMPLE 61

1,1-Bis(4-pyridinylmethyl)-3-phenyl-1H-indene bismethanesulfonate.

To a cooled (−20°) solution of 3-phenyl-1H-indene (5.0 g, 26 mmol) in tetrahydrofuran (THF) (70 ml) was added n-butyllithium (1.1 equivalents, 1.17M, 28.6 mmol, 24.5 ml) dropwise. After stirring for 30 min., a solution of 4-picolyl chloride (1.5 equivalents, 39 mmol, 5.0 g) in THF (70 ml) was added. The solution was warmed to 0°, and maintained at this temperature for 1 h. The mixture was again cooled to −20°, and additional n-butyllithium and 4-picolyl chloride were added as described above. The solution was then warmed to 0° for about 2 h. The reaction mixture was quenched with saturated ammonium chloride solution, and diluted with ether. The organic phase was washed with water, brine, and dried over magnesium sulfate. Removal of solvent by rotary evaporation provided an oil which was purified by column chromatography (silica gel, dichloromethane/methanol, 60:1 to 20:1) to give 1,1-Bis(4-pyridinylmethyl)-3-phenyl-1H-indene as a solid, 5.8 g, 15.5 mmol, 60% yield. NMR (200 MHz, CDCl$_3$) δ 3.18 (dd, 4H); 6.23 (s, 1H); 6.79 (d, 4H, J=6 Hz); 7.12 (m, 4H); 7.29 (m, 4H); 7.51 (d, 1H, J=7 Hz); 8.28 (d, 4H, J=6 Hz). Mass spec. 374.

To a solution of 1,1-bis(4-pyridinylmethyl)-3-phenyl-1H-indene (1.0 g, 2.7 mmol) in dichloromethane was added methanesulfonic acid (5.4 mmol, 0.52 g, 0.35 ml). The solvent was evaporated and the residue was recrystallized from ethyl acetate/ispropanol to give white crystals, 0.8 g, m.p. >250°.

EXAMPLE 62

4-((2,3-Dihydro-3-phenyl-1-(4-pyridinylmethyl)-1H-inden-1-ylmethyl))-pyridine dihydrochloride To a solution of 1,1-bis(4-pyridinylmethyl)-3-phenyl-1H-indene (5.8 g, 15.5 mmol) in 95% ethanol (100 ml), was added 5% palladium on carbon catalyst (1.45 g) and the mixture was shaken under hydrogen (50 psig) at room temperature for 2 h. The catalyst was removed by filtration, and the solvent removed by rotary evaporation. The oil was purified via column chromatography (silica gel, 10% methanol/dichloromethane) to give pure 4-((2,3-dihydro-3-phenyl-1-(4-pyridinylmethyl)-1H-inden-1-ylmethyl))-pyridine. NMR (200 MHz, CDCl$_3$) δ 2.05 (dd, 1H); 2.38 (dd, 1H); 2.93 (dd, 2H); 3.15 (dd, 2H); 3.42 (m, 1H); 6.67 (dd, 4H); 7.00 (d, 2H); 7.10–7.34 (m, 7H); 8.36 (d, 2H, J=5 Hz); 8.42 (d, 2H, J=5 Hz). Mass Calcd. for C$_{27}$H$_{24}$N$_2$: 376.1937. Found: 376.1951.

The oil was dissolved in methanol, and HCl in ether was added to precipitate the salt. Recrystallization from isopropanol/ethyl acetate gave a white solid, 6.2 g, m.p. 210°–225°.

EXAMPLE 63

3,3-Bis(4-pyridinylmethyl)-2,3-dihydro-1-phenyl-1H-indene-1,2-dioldiacetate dihydrochloride To a solution of 1,1-Bis(4-pyridinylmethyl)-3-phenyl-1H-indene (1.0 g, 2.7 mmol) in dry pyridine (10 ml) was added osmium tetroxide (1.0 g, 3.9 mmol, dissolved in ether). The mixture was stirred at room temperature and monitored by TLC. After completion of the reaction, sodium bisulfite (2.0 g), water (20 ml), and pyridine (5 ml) was added. The mixture was stirred for 1 h, and extracted three times with chloroform; isopropanol (4:1). The combined extracts were washed with brine, dried over magnesium sulfate, and evaporated to give 3,3-bis(4-pyridinylmethyl)-2,3-dihydro-1-phenyl-1H-indene-1,2-diol as a yellow solid, 1.15 g.

The crude 3,3-bis(4-pyridinylmethyl)2,3-dihydro-1-phenyl-1H-indene-1,2-diol was redissolved in pyridine (20 ml) and acetic anhydride (4 ml) was added. The mixture was heated to 50° for 2 days. After cooling, the volatile materials were removed by vacuum transfer, and the residue was redissolved in dichloromethane and water. The aqueous layer was made slightly basic with potassium carbonate, and extracted several times with dichloromethane. The combined extracts were dried over sodium sulfate, and the solvent was evaporated to afford an oil. This material was purified via column chromatography (silica gel, 10% methanol/dichloromethane) to give 3,3-bis(4-pyridinylmethyl)2,3-dihydro-1-phenyl-1H-indene-1,2-dioldiacetate as an oil. NMR (200 MHz, CDCl$_3$) δ 2.06 (s, 3H); 2.11 (s, 3H); 3.05–3.49 (2dd, 4H); 5.28 (s, 1H); 6.64 (dd, 1H); 6.89 (m, 6H); 7.26 (m, 5H); 7.60 (dd, 1H); 8.27 (d, 2H, J=6 Hz); 8.51 (d, 2H, J=6 Hz). Mass Calcd. for C$_{31}$H$_{28}$N$_2$O$_4$: 492.2049. Found: 492.2041.

To a solution of 3,3-bis(4-pyridinylmethyl)2,3-dihydro-1-phenyl-1H-indene-1,2-dioldiacetate in dichloromethane was added excess HCl in dichloromethane. The solvent was removed, and the residue was recrytalized from ethanol/ethyl acetate to give a white solid, 0.42 g, m.p. >300°.

EXAMPLE 64

Part A:

α,α-Bis(4-pyridinylmethyl)-2-methoxybenzeneacetonitrile

To a mechanically stirred slurry of (2-methoxyphenyl)acetonitrile (10.0 g, 68 mmol), 4-picolyl chloride hydrochloride (25.0 g, 152 mmol), and 1.2 g benzyltriethylammonium chloride in toluene (200 ml) at room temperature was added 50% NaOH (50 ml) over a period of 15 min. After addition was complete, the reaction mixture was slowly heated to 50° and maintained at that temperature for approx. 3 h. Completion of the reaction was determined by TLC. While still stirring the reaction mixture at 50°, 70 ml of water was added, and stirring was continued for 15 min. The mixture was cooled to room temperature, and the layers were separated. To the toluene layer was added 14.0 g Magneso\ (an intimate mixture of silica gel and magnesium sulfate), and the solution was stirred at 50° for 30 min. The solution was filtered, and the solvent was removed under reduced pressure. The subsequent oil was purified via column chromatography (silica gel, 10% methanol/methylene chloride) to give α,α-Bis(4-pyridinylmethyl)2-methoxybenzeneacetonitrile as a solid, 16.4 g, 73% yield. NMR (200 MHz, CDCl$_3$) δ 3.26 (d, 2H, J=13 Hz); 3.88 (d, 2H, J=13 Hz); 4.07 (s, 3H); 6.70 (m, 6H); 7.00 (m, 6H); 7.30 (m, 1H); 8.38 (m, 4H). Mass Calcd. for C$_{21}$H$_{19}$N$_3$O: 329.1528. Found: 329.1505.

The solid was treated with HCl in methanol, and ether was added to precipitate a white solid. Recrystallization from methanol/acetone produced white needles, m.p. 228°–233° (dec).

Part B:
3,3-Bis(4-pyridinylmethyl)-2(3H)-benzofuranonedihydrochloride

To a solution of α,α-Bis(4-pyridinylmethyl)-2-methoxybenzeneacetonitrile (14.36 g, 43.6 mmol) in ethylene glycol (100 ml), was added KOH (40 ml of a saturated solution) and the mixture was heated at 120°–130° under nitrogen for 20 h. The solution was cooled to room temperature, diluted with 200 ml water, and neutralized with aqueous ammonium chloride to about pH 7. The mixture was extracted with chloroform: isopropanol (4:1) until complete by TLC. The combined extracts were washed with brine, dried over sodium sulfate, and evaporated (rotary evaporator). The solid was dried in a vacuum oven at 50° and 5 torr to give 7.7 g, 22 mmol, 50% yield of α,α-bis(4-pyridinylmethyl)-2-methoxybenzeneacetic acid as a white powder.

To a suspension of α,α-bis(4-pyridinylmethyl)-2-methoxybenzene-acetic acid (7.7 g) in dichloroethane (150 ml) at 0° was added boron tribromide-methyl sulfide complex (1M in dichloromethane, 5 equivalents, 110 mmol, 110 ml). The mixture was warmed to room temperature, then heated at reflux for 20 h. After cooling to room temperature, 6N HCl (100 ml) was added, and the mixture was refluxed for 18 h. The mixture was cooled, diluted with water, and the layers were separated. The organic layer was extracted twice with 1N HCl (50 ml each). The combined aqueous layer was basified to pH 9 with concentrated ammonium hydroxide, and extracted with dichloromethane. The organic solution was dried over magnesium sulfate, filtered, and evaporated to give an oil. Purification by column chromatography (silica gel/3% methanol in dichloromethane) afforded 3,3-bis(pyridinylmethyl)-2(3H)benzofuranone [(4.7 g, 14.9 mmol, 68%) NMR (200 MHz, CDCl$_3$) δ 3.31 (dd, 4H); 6.75 (m, 1H); 6.82 (dd, 4H); 7.14–7.30 (m, 3H); 8.35 (dd, 4H). Mass Calcd. for C$_{20}$H$_{16}$N$_2$O$_2$: 316.1211. Found: 316.1202] and unreacted α,α-bis(4-pyridinylmethyl)-2-methoxybenzene-acetic acid (2.5 g, 7.2 mmol).

This compound was converted into the hydrochloride salt as described above to give a white powder, m.p. 269°–270°. Analysis. Calcd. for C$_{20}$H$_{18}$Cl$_2$N$_2$O$_2$: C, 61.70; H, 4.66; N, 7.19. Found: C, 61.65; H, 4.83; N, 7.06.

EXAMPLE 65

1,1-Bis(4-pyridinylmethyl)-1,3-dihydro-2H-inden-2-one

To stirred mixture of 2-indanone (2.64 g, 0.02 mol), 4-picolyl chloride hydrochloride (7.22 g, 0.044 mol), and benzyltriethylammonium chloride (0.45 g, 0.002 mol) in 100 ml of benzene was added 1N sodium hydroxide (84 ml, 0.084 mol) dropwise over a period of 30 min. The mixture was stirred for an additional 2.5 h. at room temperature, then heated to 60° and maintained at this temperature for 1 h. Thin layer chromatographic analysis indicated that the reaction was complete. The reaction mixture was cooled, the organic layer was separated, and diluted with an additional 80 ml of benzene. The benzene solution was extracted with 100 ml of 1N HCl. The acidic layer was basified with 10% sodium hydroxide, wherein the crude product separated as a gum. The crude material was crystallized from cyclohexane, and further purified by recrystallization from cyclohexane to give 1,1-bis(4-pyridinylmethyl)-1,3-dihydro-2H-indene-2-one as a white solid, 0.300 g, m.p. 95°–96°. NMR (200 MHz, CDCl$_3$) δ 2.66 (s, 2H); 3.07–3.34 (d, 4H); 6.73 (d, 4H); 6.82–7.47 (m, 4H). IR (nujol) 1714 cm$^{-1}$. Analysis. Calcd. for C$_{21}$H$_{18}$N$_2$O: C, 80.23; H, 5.77; N, 8.91. Found: C, 80.47; H, 5.76; N, 8.89.

EXAMPLE 124

1,1-Bis(4-pyridinylmethyl)-2(1H)-naphthalenone

To a stirred mixture of 2-tetralone (4.4 g, 0.03 mol), 4-picolylchloride hydrochloride (10.82 g, 0.066 mol), and benzyltriethylammonium chloride (1.4 g, 0.006 mol) in 80 ml of benzene was added 1N sodium hydroxide (178 ml, 0.178 mol) dropwise during a period of 1 h. at room temperature. Stirring was continued for another hour. Additional benzene (80 ml) was added, the organic layer was separated, and dried over sodium sulfate. The inorganic salts were filtered off, and to the filtrate was added 5 g of Florisil/(a magnesium silicate adsorbent). The mixture was stirred for 30 min., the solids were filtered off, and the benzene was removed by rotary evaporation. The oily residue was dissolved in the minimum amount of ethanolic HCl (5 ml), and a small amount of acetone was added, whereupon the dihydrochloride salt crystallized out of solution. This salt was collected (1.57 g), redissolved in water, and made basic with potassium carbonate. The solids obtained were air dried (900 mg), and recrystallized from cyclohexane to give 1,1-bis(4-pyridinylmethyl)-2(1H)-naphthalenone as a white solid, 460 mg, m.p. 111°–112°. NMR (200 MHz, CDCl$_3$) δ 1.9 (m, 4H); 3.30 (d, 4H); 6.55 (d, 4H); 6.95 (d, 1H); 7.15 (t, 1H); 7.45 (t, 1H); 7.66 (d, 1H); 8.30 (d, 4H). IR (nujol) 1709 cm$^{-1}$. Analysis. Calcd. for C$_{22}$H$_{20}$N$_2$O: C, 80.46; H, 6.14; N, 8.53. Found: C, 80.12; H, 6.25; N, 8.61.

EXAMPLE 125

1,1-Bis(4-pyridinylmethyl)-3,4-dihydro-7-methoxy-2(1H)-naphthalenone

To a suspension of sodium hydride (60% oil dispersion, 1.6 g, 0.04 mol) in 30 ml of dry 1,2-dimethoxyethane was added a solution of 7-methoxy-2-tetralone (3.6 g, 0.02 mol) in 30 ml of dry 1,2-dimethoxyethane dropwise. The reaction mixture turned yellow, and after all the tetralone was added, the mixture was heated gently at reflux for fifteen minutes. A solution of 4-picolyl chloride was prepared by dissolving 4-picolyl chloride hydrochloride (6.56 g, 0.04 mol) in 100 ml of water, basifying the solution with sodium bicarbonate, and extracting the free base into ether (200 ml). After drying over sodium sulfate, the mixture was filtered, and the ether was removed by rotary evaporation. The residue was immediately redissolved in 1,2-dimethoxyethane (30 ml). This solution was added dropwise to the hot reaction mixture, and the mixture was heated at reflux for 6 h. The reaction mixture was cooled, and methanol (10 ml) was added to decompose excess sodium hydride. The solvents were evaporated, and the brown oily residue was dissolved in 200 ml of dichloromethane. The organic phase was washed with water and dried over sodium sulfate. After filtration and rotary evaporation, the crude product was purified by column chromatography (silica gel, 10% methanol in ethyl acetate). The product thus obtained was recrystallized from ethyl acetate to give 1,1-bis(4-pyridinylmethyl)-3,4-dihydro-7-methoxy-2(1H)-naphthaleneone as a white solid, 1.5 g, m.p. 125°–127°. NMR (200 MHz, CDCl$_3$) δ 3.13–3.19 (d, 4H); 3.46–3.52 (d, 4H); 3.92 (s, 3H); 6.66–6.67 (d, 4H); 8.27–8.30 (d, 4H). IR 1707, 1599 cm$^{-1}$. Analysis. Calcd. for $C_{23}H_{22}N_2O_2$: C, 77.06; H, 6.18; N, 7.81. Found: C, 77.21; H, 6.13; N, 7.76.

The compounds of Examples 61–65, 124, 125 and other compounds which can be prepared by the methods described above, are illustrated by the structures represented in Tables II and III. The tables are intended to illustrate the invention, but not to limit its breadth.

In the Tables, D=double bond, S=single bond and Ph=phenyl.

TABLE II

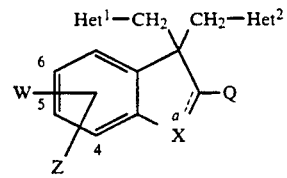

| Ex. | Q | a | X | W | Z | Het$^1$ | Het$^2$ | mp °C. |
|---|---|---|---|---|---|---|---|---|
| 61 | H | D | C—Ph | H | H | 4-pyridyl | 4-pyridyl | >250 CH$_3$SO$_3$H Salt |
| 62 | H$_2$ | S | CHPh | H | H | 4-pyridyl | 4-pyridyl | 210–225 HCl Salt |
| 63 | CH(OAc) | S | C(OAc)Ph | H | H | 4-pyridyl | 4-pyridyl | >300° HCl Salt |
| 64 | =O | S | O | H | H | 4-pyridyl | 4-pyridyl | 269–270 HCl Salt |
| 65 | =O | S | CH$_2$ | H | H | 4-pyridyl | 4-pyridyl | 95–96 |
| 66 | =O | S | CH$_2$ | H | 5-OMe | 4-pyridyl | 4-pyridyl | |
| 67 | =O | S | CH$_2$ | 5-Cl | 4-Cl | 4-pyridyl | 4-pyridyl | |
| 68 | =O | S | CH$_2$ | H | 4-Ph | 4-pyridyl | 4-pyridyl | |
| 69 | =O | S | C(CH$_3$)$_2$ | H | H | 4-pyridyl | 4-pyridyl | |
| 70 | CH$_3$ | D | C—CH$_3$ | H | H | 4-pyridyl | 4-pyridyl | |
| 71 | CH$_3$ | D | C—C$_2$H$_5$ | H | H | 4-pyridyl | 4-pyridyl | |

TABLE II-continued

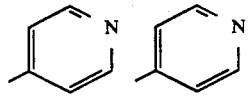

| Ex. | Q | a | X | W | Z | Het¹ | Het² | mp °C. |
|---|---|---|---|---|---|---|---|---|
| 72 | CH₃ | D | C—CH₃ | 5-OMe | 4-OMe | 4-pyridyl | 4-pyridyl | |
| 73 | H | D | C—CH₃ | 7-Ph | H | 4-pyridyl | 4-pyridyl | |
| 74 | H₂ | S | CH(CH₃) | 7-Ph | H | 4-pyridyl | 4-pyridyl | |
| 75 | H | D | C—Ph | 5-Cl | 4-Cl | 4-pyridyl | 4-pyridyl | |
| 76 | H₂ | S | CHPh | 5-Cl | 4-Cl | 4-pyridyl | 4-pyridyl | |
| 77 | H(OAc) | S | C(OAc)Ph | 5-Cl | 4-Cl | 4-pyridyl | 4-pyridyl | |
| 78 | H(OAc) | S | C(OAc)CH₃ | H | H | 4-pyridyl | 4-pyridyl | |
| 79 | H | D | C—Ph | 5-OCH₃ | 4-OCH₃ | 4-pyridyl | 4-pyridyl | |
| 80 | H₂ | S | CHPh | 5-OCH₃ | 4-OCH₃ | 4-pyridyl | 4-pyridyl | |
| 81 | H₂ | S | CHPh | H | 5-OCH₃ | 4-pyridyl | 4-pyridyl | |
| 82 | H(OAc) | S | C(OAc)Ph | 6-OCH₃ | H | 4-pyridyl | 4-pyridyl | |
| 83 | CH₃ | D | C—C₂H₅ | 4-Ph | H | 4-pyridyl | 4-pyridyl | |

TABLE II-continued

| Ex. | Q | a | X | W | Z | Het¹ | Het² | mp °C. |
|-----|---|---|---|---|---|------|------|--------|
| 84 | (H)CH₃ | S | CH—C₂H₅ | 4-Ph | H | 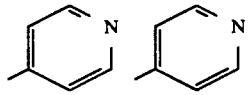 4-pyridyl | 4-pyridyl | |
| 85 | =O | S | O | H | 4-OCH₃ | 4-pyridyl | 4-pyridyl | |
| 86 | =O | S | O | 6-Br | H | 4-pyridyl | 4-pyridyl | |
| 87 | =O | S | O | 6-OCH₃ | H | 4-pyridyl | 4-pyridyl | |
| 88 | =O | S | O | 6-OCH₃ | 5-OCH₃ | 4-pyridyl | 4-pyridyl | |
| 89 | =CH₂ | S | CH₂ | H | H | 4-pyridyl | 4-pyridyl | |
| 90 | =CH₂ | S | CH₂ | H | 5-OCH₃ | 4-pyridyl | 4-pyridyl | |
| 91 | =CHCH₃ | S | CH₂ | 5-Cl | 4-Cl | 4-pyridyl | 4-pyridyl | |
| 92 | =CHPh | S | CH₂ | H | 4-Ph | 4-pyridyl | 4-pyridyl | |
| 93 | =CHPh | S | C(CH₃)₂ | H | H | 4-pyridyl | 4-pyridyl | |
| 94 | H | D | C—Ph | H | H | 4-pyrimidinyl | 4-pyrimidinyl | |

TABLE II-continued

| Ex. | Q | a | X | W | Z | Het¹ | Het² | mp °C. |
|---|---|---|---|---|---|---|---|---|
| 95 | H₂ | S | CHPh | H | H | pyridyl | tetrahydrofuryl (O) | |
| 96 | =O | S | O | 6-Br | H | pyridyl | pyrazolyl (NH-N) | |
| 97 | =O | S | O | H | H | pyridyl | thienyl (S) | |
| 98 | H | D | C(CH₃) | 7-Ph | H | pyridyl | tetrahydrofuryl (O) | |
| 99 | =O | S | CH₂ | H | H | pyridyl | pyrimidinyl | |
| 100 | =O | S | CH₂ | 5-Cl | 4-Cl | pyrimidinyl | pyrimidinyl | |
| 101 | H | D | CPh | H | H | pyridyl | pyrimidinyl | |
| 102 | H(OAc) | S | C(OAc)Ph | H | H | pyridyl | pyrimidinyl | |
| 103 | H₂ | S | CHCH₃ | 5-OCH₃ | 4-OCH₃ | pyridyl | tetrahydrofuryl (O) | |
| 104 | =O | S | CH₂ | H | H | pyridyl | pyrimidinyl | |
| 105 | =O | S | O | 6-OCH₃ | H | pyridyl | tetrahydrofuryl (O) | |

TABLE II-continued

| Ex. | Q | a | X | W | Z | Het¹ | Het² | mp °C. |
|---|---|---|---|---|---|---|---|---|
| 106 | =O | S | CH₂ | H | H | pyrimidine | tetrahydrofuran | |
| 107 | =O | S | O | H | H | pyrimidine | pyrimidine | |
| 108 | =O | S | O | H | H | pyridine | pyrazine | |
| 109 | =O | S | CH₂ | H | H | pyridine | tetrahydrofuran | |
| 110 | H | D | CPh | H | H | pyridine | pyrazine | |
| 111 | H₂ | S | CHPh | H | 4-Ph | pyrimidine | tetrahydrofuran | |
| 112 | =CHPh | S | CH₂ | H | H | pyridine | pyrimidine | |
| 113 | =CHCH₃ | S | CH₂ | 5-OCH₃ | H | pyridine | thiophene | |
| 114 | (H)CH₂Ph | S | CH₂ | 5-OCH₃ | H | pyridine | pyrimidine | |
| 115 | (H)CH₂CH₃ | S | CH₂ | H | H | pyridine | pyrimidine | |
| 116 | CH₃ | D | C(CH₃) | H | 4-Ph | pyrimidine | tetrahydrofuran | |

TABLE II-continued
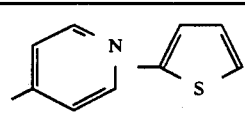
| Ex. | Q | a | X | W | Z | Het¹ | Het² | mp °C. |
|---|---|---|---|---|---|---|---|---|
| 117 | CH₃ | D | C(CH₃) | H | H | 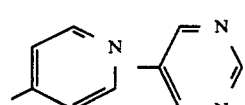 | 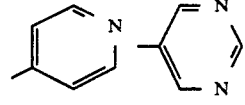 | |
| 118 | H₂ | S | CHCH₃ | H | H | 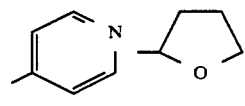 | 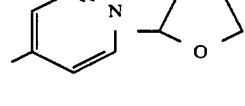 | |
| 119 | H(OAc) | S | C(OAc)Ph | H | H | 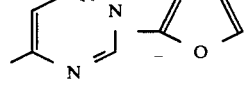 | 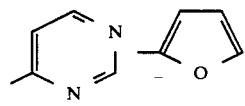 | |
| 120 | H | D | CPh | H | H | 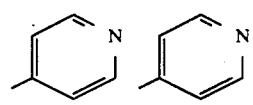 | 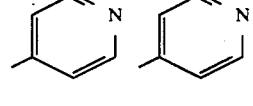 | |
| 121 | (H)OH | S | CH₂ | H | H | 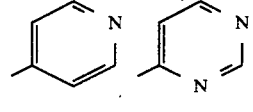 | 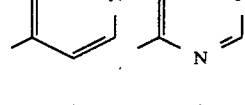 | |
| 122 | (H)(OAc) | S | CH₂ | 5-OCH₃ | H | 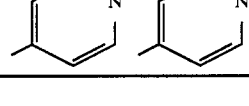 | 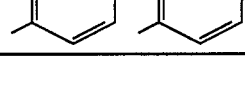 | |
| 123 | =N—OCH₃ | S | CH₂ | H | H |  | 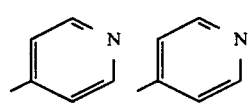 | |
TABLE III
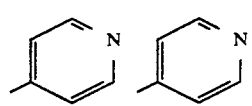
| Ex. | Q | W | Z | Het¹ | Het² | mp °C. |
|---|---|---|---|---|---|---|
| 124 | =O | H | H | 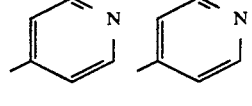 |  | 111–112° |
| 125 | =O | 7-OCH₃ | H | | | 125–127 |

TABLE III-continued
| Ex. | Q | W | Z | Het¹ | Het² | mp °C. |
|---|---|---|---|---|---|---|
| 126 | —OH | H | H | 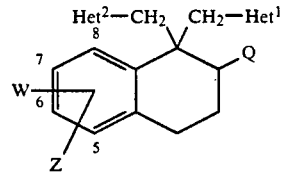 | 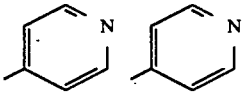 | |
| 127 | —OCOCH₃ | H | H |  | 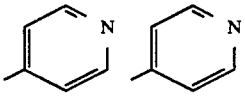 | |
| 128 | =CH₂ | H | H |  | 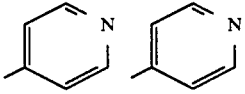 | |
| 129 | =CHPh | H | H |  | 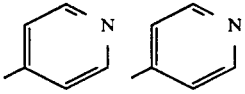 | |
| 130 | —CH₃ | H | H |  | 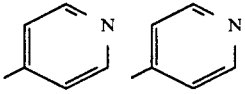 | |
| 131 | =N—OCH₃ | H | H |  | 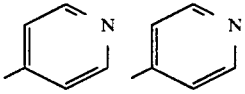 | |
| 132 | =N—OH | 7-OCH₃ | H |  | 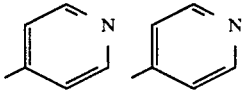 | |
| 133 |  | H | H |  | 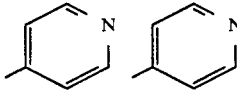 | |
| 134 |  | H | H |  | 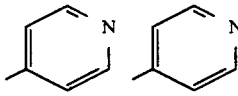 | |
| 135 | H₂ | H | H |  | 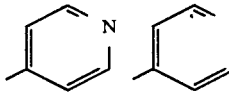 | |
| 136 |  | H | H |  | 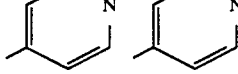 | |
| 137 | (H)F | H | H |  | 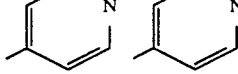 | |

TABLE III-continued

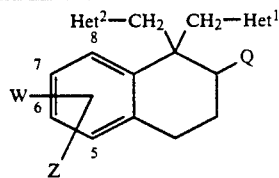

| Ex. | Q | W | Z | Het¹ | Het² | mp °C. |
|---|---|---|---|---|---|---|
| 138 | F₂ | H | H | 4-pyridyl | 4-pyridyl | |
| 139 | =O | 8-CH₃ | 5-CH₃ | 4-pyridyl | 3-pyridyl | |
| 140 | =O | H | 6-OCH₃ | 4-pyridyl | 4-pyridyl | |
| 141 | =O | H | 5-Cl | 4-pyridyl | 4-pyridyl | |
| 142 | =O | H | 5-NH₂ | 4-pyridyl | 4-pyridyl | |
| 143 | =O | 7-OAc | H | 4-pyridyl | 4-pyridyl | |
| 144 | =O | H | 5-NO₂ | 4-pyridyl | 4-pyridyl | |
| 145 | =O | 8-OCH₃ | 7-OCH₃ | 4-pyridyl | 4-pyridyl | |
| 146 | =CH₂ | 7-OCH₃ | H | 4-pyridyl | 4-pyridyl | |
| 147 | =CH₂ | H | 5-NH₂ | 4-pyridyl | 4-pyrimidinyl | |
| 148 | =CH₂ | H | 5-Cl | 4-pyridyl | 2-tetrahydrofuryl | |
| 149 | =O | H | H | 4-pyrimidinyl | 4-pyrimidinyl | |

TABLE III-continued

| Ex. | Q | W | Z | Het[1] | Het[2] | mp °C. |
|---|---|---|---|---|---|---|
| 150 | =O | 7-OCH$_3$ | H | pyridyl | tetrahydrofuryl | |
| 151 | =CH$_2$ | H | 6-OCH$_3$ | pyridyl | pyridazinyl | |
| 152 | =CHPh | H | 5-NO$_2$ | pyrimidinyl | tetrahydrofuryl | |
| 153 | —OCOCH$_3$ | 8-CH$_3$ | H | pyridyl | pyridyl | |
| 154 | =N—OCH$_3$ | H | H | pyrimidinyl | pyrimidinyl | |
| 155 | =CH$_2$ | H | 5-Cl | pyridyl | tetrahydrofuryl | |
| 156 | =CHPh | H | 5-NO$_2$ | pyridyl | thienyl | |
| 157 | (H)CH$_2$Ph | H | H | pyridyl | pyrazolyl | |
| 158 | 1,3-dioxolane | 7-OCH$_3$ | H | pyridyl | pyrimidinyl | |
| 159 | =O | 8-OCH$_3$ | H | pyridyl | pyrimidinyl | |
| 160 | =CH$_2$ | H | 6-OCH$_3$ | pyridyl | pyrimidinyl | |

TABLE III-continued

| Ex. | Q | W | Z | Het[1] | Het[2] | mp °C. |
|---|---|---|---|---|---|---|
| 161 | =O | 8-CH$_3$ | H | 3-thienyl | 3-thienyl | |
| 162 | =CHPh | H | 6-CH$_3$ | 4-pyridyl | 2-tetrahydrofuryl | |
| 163 | —OH | H | H | 4-pyridyl | 2-tetrahydrofuryl | |
| 164 | =N—OCH$_3$ | H | 6-CF$_3$ | 4-pyridyl | 2-tetrahydrofuryl | |
| 165 | =CH$_2$ | H | 5-NO$_2$ | 4-pyridyl | 3-pyrazolyl | |
| 166 | =CHPh | H | H | 4-pyridyl | 3-pyridazinyl | |
| 167 | 1,3-dioxolane | 7-OAc | H | 4-pyridyl | 3-pyridazinyl | |
| 168 | 1,3-dithiane | 7-CH$_3$ | H | 4-pyridyl | 2-tetrahydrofuryl | |
| 169 | —OCOCH$_3$ | H | 5-Cl | 2-(4-methylpyrimidinyl) | imidazolyl | |
| 170 | =CHCH$_3$ | 7-OCH$_3$ | H | 4-pyridyl | 2-(4-methylpyrimidinyl) | |
| 171 | (CH$_3$)(OH) | H | H | 4-pyridyl | 2-tetrahydrofuryl | |

TABLE III-continued

Structure: 1,2,3,4-tetrahydronaphthalene with Het²—CH₂ and CH₂—Het¹ at position 1, Q at position 2, W at position 6, Z at position 5, positions 7 and 8 labeled.

| Ex. | Q | W | Z | Het¹ | Het² | mp °C |
|---|---|---|---|---|---|---|
| 172 | =O | H | H | 4-pyridyl | 3-methylthiophen-2-yl | |
| 173 | =O | 7-OCH₃ | H | 4-pyridyl | pyrimidin-2-yl | |
| 174 | =O | H | H | 4-pyridyl | 3-methylthiophen-2-yl | |
| 175 | =O | H | H | 4-pyridyl | tetrahydrofuran-2-yl | |
| 176 | =CH₂ | H | 6-OEt | 4-pyridyl | pyrazin-2-yl | |
| 177 | =CHCH₃ | H | H | 4-pyridyl | pyridazin-3-yl | |
| 178 | =CHPh | H | 5-NH₂ | pyrimidin-4-yl | thiophen-2-yl | |
| 179 | =O | H | H | pyrimidin-4-yl | pyrimidin-4-yl | |
| 180 | —OH | 8-OMe | 7-OMe | 4-pyridyl | tetrahydrofuran-2-yl | |
| 181 | —OCOCH₃ | H | H | 4-pyridyl | pyrazin-2-yl | |

EXAMPLE 182

2,2Bis(4-pyridinylmethyl)-1(2H)-acenaphthylenone dihydrochloride

To a mechanically stirred slurry of acenaphthylenone (1.682 g, 10 mmol), 4-picolyl chloride hydrochloride (3.3 g, 22 mmol), and 0.2 g benzyltriethylammonium chloride in toluene (50 ml) at room temperature was added 50% NaOH (5 ml) over a period of 15 min. After addition was complete, the reaction mixture was slowly heated to 50° and maintained at that temperature for approx. 3 h. Completion of the reaction was determined by TLC. While still stirring the reaction mixture at 50°, 10 ml of water was added, and stirring was continued for 15 min. The mixture was cooled to room temperature, and the layers were separated. To the toluene layer was added 2.0 g Magnesol\ (an intimate mixture of silica gel and magnesium sulfate), and the solution was stirred at 50° for 30 min. The solution was filtered, and the solvent was removed under reduced pressure. The subsequent oil was purified via column chromatography (silica gel, ethyl acetate) to give a solid, which was recrystallized from ethyl acetate/hexane to give 2.51 g, 71% yield, of 2,2-bis(4-pyridinylmethyl)-1(2H)-acenaphthylenone as white crystals, m.p. 165°.

The solid was treated with HCl in methanol, and ether was added to precipitate a white solid. Recrystallization from methanol/acetone produced white needles, m.p. 255° (dec). NMR (200 MHz, DMSO-$d_6$) δ 3.16 (s, 2H), 3.68 (d, 2H, J=12 Hz), 3.83 (d, 2H, J=12 Hz), 7.47 (d, 4H, J=6 Hz), 7.60-8.15 (m, 6H), 8.53 (d, 4, J=6 Hz). Analysis. Calcd. for $C_{24}H_{20}Cl_2N_2O \cdot \frac{1}{2}H_2O$: C, 66.65; H, 4.90; N, 6.48. Found: C, 66.32; H, 5.26; N, 6.08.

EXAMPLE 183

4-((1,2-Dihydro-2-methylene-1-(4-pyridinylmethyl)-1-acenaphthylen-1-ylmethyl))pyridine dihydrochloride.

To a mechanically stirred slurry of methyltrimethylphosphonium bromide (6.25 g, 17.5 mmol) in THF (150 ml) at 0° was added n-butyllithium (1.6M, 11 ml, 17.5 mmol) dropwise. The solution was warmed to room temperature for 1 hr., then cooled back down to 0°. A solution of the ketone 2,2-bis(4-pyridinylmethyl)-1(2H)-acenaphthylenon (2.25 g, 7 mmol) in THF (50 ml) was added dropwise. After addition was complete, the mixture was warmed to room temperature, and stirred for about 18 hr. Saturated ammonium chloride solution was added, the mixture was diluted with ether, and the layers were separated. The organic layer was washed with water, then saturated sodium chloride solution. After drying over magnesium sulfate, the solution was filtered and concentrated by rotary evaporation to give pyridine a brown oil. This material was purified by column chromatography (silica gel, 10% methanol/ethyl acetate) to give 4-((1,2-dihydro-2-methylene-1-(4-pyridinylmethyl-1-acenaphthylen-1-ylmethyl))pyridine as a white solid, 2.27 g, 6.5 mmol, 93% yield.

The aforementioned solid was treated with HCl in methanol, and ether was added to produced a white solid. Recrystallization from methanol/acetone/ether provided white needles, m.p. >250° (dec). NMR (200 MHz, DMSO-$d_6$) δ 3.81 (q, 4H, J=13 Hz), 5.97 (s, 1H), 6.25 (s, 1H), 7.43 (m, 6H), 7.61 (m, 3H), 7.75 (m, 1H), 8.47 (d, 4H, J=6 Hz).

The compounds of Examples 182 and 183, and other compounds which can be prepared by the methods described above, are illustrated by the structures represented in Table IV. The table is intended to illustrate the invention, but not to limit its breadth.

TABLE IV

| Ex. | Q | W | Z | Het¹ | Het² | mp °C. |
|---|---|---|---|---|---|---|
| 182 | =O | H | H | 4-pyridyl | 4-pyridyl | 255 (dec) HCl Salt |
| 183 | =CH₂ | H | H | 4-pyridyl | 4-pyridyl | 248–264 (dec) HCl Salt |
| 184 | =S | H | H | 4-pyridyl | 4-pyridyl | |
| 185 | —OCOCH₃ | H | H | 4-pyridyl | 4-pyridyl | |
| 186 | =O | H | H | 4-pyridyl | tetrahydrofuranyl | |

TABLE IV-continued
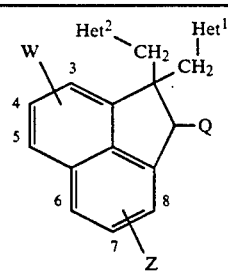
| Ex. | Q | W | Z | Het¹ | Het² | mp °C. |
|---|---|---|---|---|---|---|
| 187 | =CH₂ | H | H | 4-pyridyl | 3-tetrahydrofuryl | |
| 188 | =O | H | H | 4-pyridyl | 4-pyrimidinyl | |
| 189 | =CH₂ | H | H | 4-pyrimidinyl | 4-pyrimidinyl | |
| 190 | =S | H | H | 4-pyridyl | 3-(1H-pyrazolyl) | |
| 191 | =O | H | H | 4-pyrimidinyl | 4-pyrimidinyl | |
| 192 | =O | H | H | 4-pyridyl | 3-(1H-pyrazolyl) | |
| 193 | =O | H | H | 4-pyridyl | 3-thienyl | |
| 194 | =O | H | H | 4-pyridyl | 3-tetrahydrofuryl | |
| 195 | =O | H | H | 4-pyridyl | 2-tetrahydrofuryl | |
| 196 | =O | H | H | 4-pyridyl | 5-pyrimidinyl | |
| 197 | =O | H | H | 4-pyridyl | 2-pyrimidinyl | |

TABLE IV-continued

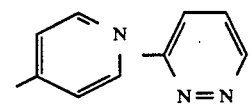

| Ex. | Q | W | Z | Het¹ | Het² | mp °C. |
|---|---|---|---|---|---|---|
| 198 | =O | H | H | 4-pyridyl | pyridazin-3-yl | |
| 199 | =O | H | H | 4-pyridyl | thien-3-yl | |
| 200 | =O | H | H | 4-pyridyl | tetrahydrofuran-2-yl | |
| 201 | =O | H | H | 4-pyridyl | pyrazin-2-yl | |
| 202 | =O | H | H | pyrimidin-4-yl | tetrahydrofuran-3-yl | |
| 203 | =CH₂ | H | H | 4-pyridyl | pyrimidin-4-yl | |
| 204 | =CH₂ | H | H | 4-pyridyl | pyrazol-3-yl | |
| 205 | =CH₂ | H | H | 4-pyridyl | tetrahydrofuran-3-yl | |
| 206 | =CH₂ | H | H | 4-pyridyl | pyrimidin-5-yl | |
| 207 | =CH₂ | H | H | 4-pyridyl | tetrahydrofuran-2-yl | |
| 208 | =S | H | H | 4-pyridyl | tetrahydrofuran-3-yl | |

TABLE IV-continued

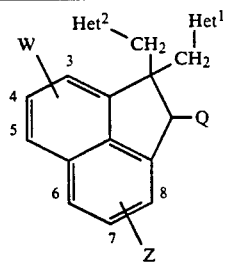

| Ex. | Q | W | Z | Het¹ | Het² | mp °C. |
|---|---|---|---|---|---|---|
| 209 | =S | H | H | 4-pyrimidinyl | 4-pyrimidinyl | |
| 210 | =S | H | H | 4-pyridyl | 2-pyrimidinyl | |
| 211 | =S | H | H | 4-pyridyl | 5-pyrimidinyl | |
| 212 | =S | H | H | 4-pyrimidinyl | 2-pyrimidinyl | |
| 213 | =CHPh | 5-Br | H | 4-pyridyl | 4-pyridyl | |
| 214 | =CHCH₃ | 5-Br | H | 4-pyridyl | 3-tetrahydrofuryl | |
| 215 | —OH | H | H | 4-pyridyl | 3-pyridyl | |
| 216 | =S | H | 6-NO₂ | 4-pyridyl | 4-pyrimidinyl | |
| 217 | =CH₂ | 5-NO₂ | H | 4-pyridyl | 2-tetrahydrofuryl | |
| 218 | =CHPh | H | 8-CH₃ | 4-pyridyl | 3-pyridyl | |
| 219 | =O | H | 8-CH₃ | 4-pyridyl | 2-(1H-imidazolyl) | |

TABLE IV-continued

[Structure: acenaphthylene-based core with substituents W at position 3-5 region, numbered positions 3,4,5,6,7,8; Q substituent; and two CH$_2$-Het groups (Het$^1$ and Het$^2$) at the top]

| Ex. | Q | W | Z | Het$^1$ | Het$^2$ | mp °C. |
|---|---|---|---|---|---|---|
| 220 | =CH$_2$ | H | 8-CH$_3$ | 3-pyridyl | 3-pyridyl | |
| 221 | =O | 5-NH$_2$ | H | 4-pyridyl | 4-pyridyl | |
| 222 | =CH$_2$ | 5-NH$_2$ | H | 4-pyridyl | 3-thienyl | |
| 223 | =S | 5-NH$_2$ | H | 4-pyridyl | 3-tetrahydrofuryl | |
| 224 | =N—OCH$_3$ | H | 6-NH$_2$ | 4-pyridyl | 3-pyridazinyl | |
| 225 | —CH$_3$ | H | 6-NH$_2$ | 4-pyridyl | 4-pyrimidinyl | |
| 226 | —OCOCH$_3$ | H | 6-NH$_2$ | 4-pyridyl | 4-pyridyl | |
| 227 | —OCOCH$_3$ | H | 6-NO$_2$ | 4-pyridyl | 2-tetrahydrofuryl | |
| 228 | —OCOCH$_3$ | H | 6-NO$_2$ | 4-pyrimidinyl | 4-pyrimidinyl | |
| 229 | =CH$_2$ | 5-Cl | 6-Cl | 4-pyridyl | 4-pyridyl | |
| 230 | =O | 5-Cl | 6-Cl | 4-pyridyl | 4-pyrimidinyl | |

TABLE IV-continued

| Ex. | Q | W | Z | Het¹ | Het² | mp °C. |
|---|---|---|---|---|---|---|
| 231 | =CHPh | 5-Cl | 6-Cl | pyridine | tetrahydrofuran | |
| 232 | =S | 5-Cl | 6-Cl | pyridine | pyrimidine | |
| 233 | —OCOCH₃ | 5-Cl | 6-Cl | pyrimidine | thiophene | |
| 234 | =O | 5-CN | H | pyridine | pyrimidine | |
| 235 | =CH₂ | 5-OH | H | pyridine | tetrahydrofuran | |
| 236 | =S | 5-OCH₃ | H | pyridine | pyridazine | |
| 237 | =CHPh | H | 6-COCH₃ | pyridine | pyridine | |
| 238 | =O | H | 6-COCH₃ | pyridine | pyrimidine | |
| 239 | —OCOCH₃ | 3-CH₃ | 8-CH₃ | pyridine | tetrahydrofuran | |

EXAMPLE 240

4,4-Bis(4-pyridinylmethyl)-3,4-dihydro-6,7-dimethoxy-1-phenyl-isoquinoline

To a suspension of amide N-((2-3,4-dimethoxyphenyl)-3-(4-pyridinyl)-2-(4-pyridinylmethyl)propyl))-benzamide (2.306 g, 4.93 mmol) in acetonitrile (20 ml), was added phosphorus oxychloride (6 ml) and the mixture was heated to reflux for 6 hrs. After cooling to room temperature, the solvents removed by vacuum transfer. The residue was dissolved in water, basified with sodium hydroxide, and extracted with dichloromethane. After drying over magnesium sulfate, the solvent was removed by rotary evaporation to give a yellow oil. Purification by column chromatography (silica gel, 10% methanol/dichloromethane) gave a solid, which was recrystallized from ether/ethyl acetate to give white crystals of the title compound, 1.898 g, 4.22 mmol, 86% yield, m.p. 168.5°–169°. NMR (200 MHz, CDCl$_3$) δ 2.96 (d, 2H, J=13 Hz); 3.10 (d, 2H, J=13 Hz); 3.74 (s, 5H); 3.84 (s, 3H); 6.72 (s, 1H); 6.81 (s, 1H); 6.95 (d, 4H, J=5 Hz); 7.43 (s, 5H); 8.44 (d, 4H, J=5). IR (KBr) 2930, 1599, 1559, 1515, 1283 cm$^{-1}$. Mass spec. 449. Analysis. Calcd. for C$_{29}$H$_{27}$N$_3$O$_2$: C, 77.48; H, 6.05; N, 9.35. Found: C, 77.29; H, 6.36; N, 9.06.

EXAMPLE 288

4,4-Bis(4-pyridinylmethyl)-2-phenyl-1,3(2H, 4H)-isoquinolinedione

The procedure used was essentially the same as described by Chan and Huang, *Synthesis*, 452 (1982). To a solution of 2-phenyl-1,3(2H, 4H)-isoquinolinedione [Ueda, et. al, *J. Polym. Sci., Polym. Chem. Ed.* 17, 2459 (1979)], (2.14 g, 9.02 mmol) and picolyl chloride (30.5 mmol, freshly prepared from 5.0 g of the hydrochloride) in chloroform (50 ml) was added benzyltriethylammonium chloride (6.17 g, 27 mmol) and potassium carbonate (3.75 g, 27 mmol). The mixture was heated at 50° for 2 hr., then held at room temperature overnight. Water (15 ml) was added, and the mixture was extracted several times with chloroform. After drying over magnesium sulfate, the solvent was removed by rotary evaporation to give a green-black oil. The crude product was purified via column chromatography (silica gel, 5% methanol/dichloromethane) and recrystallized from hexane/dichloromethane to give 4,4-bis(4-pyridinylmethyl)-2-phenyl-1,3(2H, 4H)-isoquinolinedione as a pale yellow solid, 3.034 g, 7.2 mmol, 80% yield. Further recrystallization from ethyl acetate/hexane provided off-white crystals of the title compound, m.p. >270°. NMR (200 MHz, CDCl$_3$) δ 3.45 (d, 2H, J=13 Hz); 3.81 (d, 2H, J=13 Hz); 6.56 (m, 2H); 6.68 (d, 4H, J=6 Hz); 7.41 (m, 3H); 7.53 (m, 1H); 7.91 (d, 2H, J=4 Hz); 8.02 (d, 2H, J=8 Hz); 8.35 (d, 4H, J=6 Hz). IR (KBr) 1716, 1674, 1600, 1375 cm$^{-1}$. Mass spec. 419. Analysis. Calcd. for C$_{27}$H$_{21}$N$_3$O$_2$: C, 77.31; H, 5.05; N, 10.02. Found: C, 77.12; H, 5.27; N, 9.93.

The compounds of Examples 240 and 288, and other compounds which can be prepared by the methods described above, are illustrated by the structures represented in Tables V and VI. The tables are intended to illustrate the invention, but not to limit its breadth.

TABLE V

| Ex. | Q | X | V | W | Z | Het$^1$ | Het$^2$ | mp °C. |
|---|---|---|---|---|---|---|---|---|
| 240 | H$_2$ | N | C—Ph | 6-OCH$_3$ | 7-OCH$_3$ | 4-pyridyl | 4-pyridyl | 169 |
| 241 | H$_2$ | N | C(CH$_3$) | 6-OCH$_3$ | | 4-pyridyl | 4-pyridyl | |
| 241 | H$_2$ | N | CH | H | 7-OCH$_3$ | 4-pyridyl | 4-pyridyl | |
| 243 | H$_2$ | N | OC$_2$H$_5$ | 5-OCH$_3$ | H | 4-pyridyl | 4-pyridyl | |
| 244 | H$_2$ | N | CPh | H | H | 4-pyridyl | 4-pyridyl | |
| 245 | H$_2$ | N | OCH$_3$ | 7-OCH$_3$ | 6-Br | 4-pyridyl | 4-pyridyl | |
| 246 | H$_2$ | N | CPh | 5-CF$_3$ | H | 4-pyridyl | 4-pyridyl | |

TABLE V-continued

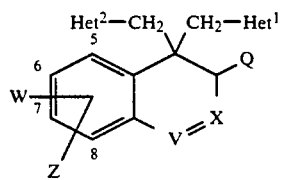

| Ex. | Q | X | V | W | Z | Het¹ | Het² | mp °C. |
|---|---|---|---|---|---|---|---|---|
| 247 | $H_2$ | N | C(CH₃) | H | 7-CH₃ | pyridyl | pyridyl | |
| 248 | $H_2$ | N | C(m-OCH₃Ph) | H | 7-NO₂ | pyridyl | pyridazinyl | |
| 249 | $H_2$ | N | C—Ph | 6-OCH₃ | 7-OCH₃ | pyrimidinyl | pyrimidinyl | |
| 250 | $H_2$ | N | OCH₃ | 6-OCH₃ | H | pyridyl | tetrahydrofuranyl | |
| 251 | $H_2$ | N | C(p-OCH₃Ph) | H | 7-OCH₃ | pyridyl | pyrazinyl | |
| 252 | $H_2$ | N | CH | H | 6-Cl | pyridyl | tetrahydrofuranyl | |
| 253 | $H_2$ | N | CPh | 5-OCH₃ | 8-OCH₃ | pyridyl | pyrazolyl | |
| 254 | $H_2$ | N | C(CH₃) | 6-OCH₃ | 7-OCH₃ | pyridyl | thienyl | |
| 255 | $H_2$ | N | CPh | H | 7-Br | pyridyl | pyridyl | |
| 256 | $H_2$ | N | CPh | H | 7-CN | pyridyl | pyrimidinyl | |
| 257 | $H_2$ | N | C(m-ClPh) | H | 7-OCH₃ | pyridyl | pyridazinyl | |

TABLE V-continued

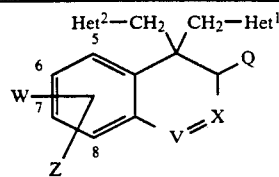

| Ex. | Q | X | V | W | Z | Het¹ | Het² | mp °C. |
|---|---|---|---|---|---|---|---|---|
| 258 | H₂ | N | C(CH₃) | 5-CF₃ | H | 4-pyridyl | pyridazinyl | |
| 259 | H₂ | N | CPh | 5-CH₃ | 7-CH₃ | 4-pyridyl | tetrahydrofuryl | |
| 260 | H₂ | N | OC₂H₅ | 5-OCH₃ | H | 4-pyridyl | tetrahydrofuryl | |
| 261 | H₂ | N | CPh | H | 7-Ph | 4-pyridyl | pyrimidinyl | |
| 262 | H₂ | N | CPh | 6-OCH₃ | 7-OCH₃ | 4-pyridyl | pyrimidinyl | |
| 263 | H₂ | N | CH | 6-OCH₃ | H | 4-pyridyl | 1H-pyrazolyl | |
| 264 | =O | CH | CH | H | H | 4-pyridyl | 4-pyridyl | |
| 265 | =O | CH | CH | H | 7-Br | 4-pyridyl | 4-pyridyl | |
| 266 | =O | CH | CH | H | 7-OCH₃ | 4-pyridyl | 4-pyridyl | |
| 267 | =O | CH | CH | H | 7-OH | 4-pyridyl | 4-pyridyl | |
| 268 | =O | CH | CH | H | 8-NH₂ | 4-pyridyl | 4-pyridyl | |
| 269 | =O | CH | CH | 5-NH₂ | H | 4-pyridyl | 4-pyridyl | |

TABLE V-continued

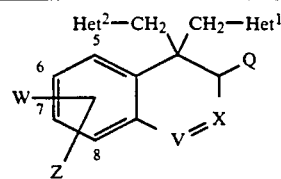

| Ex. | Q | X | V | W | Z | Het¹ | Het² | mp °C. |
|---|---|---|---|---|---|---|---|---|
| 270 | =CH$_2$ | CH | CH | H | H | pyrimidinyl | pyrimidinyl | |
| 271 | =CH$_2$ | CH | CH | H | 7-OCH$_3$ | pyrimidinyl | tetrahydrofuranyl | |
| 272 | —OH | CH | CH | 5-NH$_2$ | H | pyridyl | tetrahydrofuranyl | |
| 273 | —OH | CH | CH | H | 7-Br | pyridyl | pyrimidinyl | |
| 274 | =S | CH | CH | H | H | pyrimidinyl | pyrimidinyl | |
| 275 | =S | CH | CH | H | 7-OH | pyridyl | pyrazolyl (NH) | |
| 276 | —OCOCH$_3$ | CH | CH | H | H | pyridyl | pyrimidinyl | |
| 277 | —OCOPh | CH | CH | H | 7-OCH$_3$ | pyridyl | pyridyl | |
| 278 | =O | CH | CH | H | H | pyridyl | pyridyl | |
| 279 | =O | CH | CH | H | 7-Br | pyridyl | pyridyl | |
| 280 | —OH | CH | CH | H | 7-OCH$_3$ | pyridyl | thienyl | |

TABLE V-continued

| Ex. | Q | X | V | W | Z | Het¹ | Het² | mp °C. |
|---|---|---|---|---|---|---|---|---|
| 281 | —OH | CH | CH | H | H | 4-pyridyl | tetrahydrofuran-2-yl (O) | |
| 282 | —OCOCH₃ | CH | CH | 5-NH₂ | H | 4-pyridyl | thien-2-yl | |
| 283 | =CHPh | CH | CH | H | H | 4-pyridyl | pyrimidin-2-yl | |
| 284 | (Ph)(OH) | CH | CH | H | 8-NH₂ | pyrimidin-2-yl | pyrimidin-2-yl | |
| 285 | —OCOPh | CH | CH | H | H | 4-pyridyl | tetrahydrofuran-3-yl | |
| 286 | =S | CH | CH | H | 7-Br | 4-pyridyl | pyridazin-3-yl | |
| 287 | =S | CH | CH | H | 7-OH | 4-pyridyl | pyrimidin-5-yl | |

TABLE VI

| Ex. | Q | X | V | W | Z | Het¹ | Het² | mp °C. |
|---|---|---|---|---|---|---|---|---|
| 288 | =O | N—Ph | C=O | H | H | 4-pyridyl | 4-pyridyl | >270 |
| 289 | H₂ | NCOCH₃ | C—Ph | 6-OCH₃ | 7-OCH₃ | 4-pyridyl | 4-pyridyl | 278–280 (dec) |

TABLE VI-continued

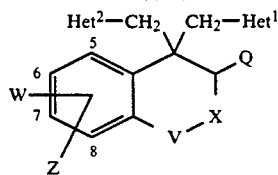

| Ex. | Q | X | V | W | Z | Het¹ | Het² | mp °C. |
|---|---|---|---|---|---|---|---|---|
| 290 | =O | O | C=O | H | H | 4-pyridyl | 4-pyridyl | |
| 291 | =O | O | C=O | 6-OAc | H | 4-pyridyl | 4-pyridyl | |
| 292 | =O | O | C=O | H | 8-OH | 4-pyridyl | 4-pyridyl | |
| 293 | =O | O | C=O | 5-OCH₃ | 6-OCH₃ | 4-pyridyl | 4-pyridyl | |
| 294 | =O | O | CH₂ | H | 7-CH₃ | 4-pyridyl | 4-pyridyl | |
| 295 | =O | O | CH₂ | 7-OCH₃ | 8-OCH₃ | 4-pyridyl | 4-pyridyl | |
| 296 | =O | NCH₃ | C=O | H | H | 4-pyridyl | 4-pyridyl | |
| 297 | =O | NCH₃ | CH₂ | H | H | 4-pyridyl | 4-pyridyl | |
| 298 | H₂ | NCOPh | CH₂ | 6-OCH₃ | 7-OCH₃ | 4-pyridyl | 4-pyridyl | |
| 299 | H₂ | NCOCH₃ | CHCH₃ | 6-OCH₃ | H | 4-pyridyl | 4-pyridyl | |
| 300 | H₂ | NCOCH₃ | CH₂ | H | H | 4-pyridyl | 4-pyridyl | |
| 301 | =O | O | CH₂ | 5-OCH₃ | H | 4-pyridyl | 4-pyrimidinyl | |

TABLE VI-continued

| Ex. | Q | X | V | W | Z | Het¹ | Het² | mp °C. |
|---|---|---|---|---|---|---|---|---|
| 302 | =O | O | C=O | 5-OCH$_3$ | 8-OCH$_3$ | pyrimidinyl | pyrimidinyl | |
| 303 | =O | NPh | C=O | 5-CH$_3$ | H | pyridyl | tetrahydrofuranyl | |
| 304 | =O | NCH$_3$ | C=O | H | 7-F | pyridyl | thienyl | |
| 305 | H$_2$ | NCOPh | CHPh | H | 7-OCH$_3$ | pyridyl | pyridyl | |
| 306 | H$_2$ | NH | C=O | H | 7-NO$_2$ | pyrimidinyl | pyrimidinyl | |
| 307 | H$_2$ | NPh | C=O | 6-CH$_3$ | 7-CH$_3$ | pyridyl | tetrahydrofuranyl | |
| 308 | =O | NPh | C=O | H | 7-CF$_3$ | pyridyl | pyrazolyl | |
| 309 | =O | O | C=O | H | 8-NH$_2$ | pyridyl | tetrahydrofuranyl | |
| 310 | =O | O | C=O | 5-F | 8-F | pyridyl | tetrahydrofuranyl | |
| 311 | =O | O | CH$_2$ | H | 7-OCH$_3$ | pyridyl | pyridyl | |
| 312 | =O | O | CH$_2$ | 6-CH$_3$ | 8-CH$_3$ | pyridyl | pyrazinyl | |

TABLE VI-continued

Structure: Het²—CH₂ and CH₂—Het¹ on central carbon attached to benzene ring (positions 5,6,7,8 with W at 6, Z at 8), with Q substituent, V—X ring closure.

| Ex. | Q | X | V | W | Z | Het¹ | Het² | mp °C. |
|---|---|---|---|---|---|---|---|---|
| 313 | =O | NPh | CH₂ | H | 7-NO₂ | 4-pyridyl | pyridazinyl (N=N) | |
| 314 | H₂ | NH | C=O | H | 7-Br | 4-pyridyl | pyrimidinyl | |
| 315 | H₂ | NCOCH₃ | CH₂ | H | 7-OCH₃ | 4-pyridyl | pyrazinyl | |
| 316 | H₂ | NCOPh | CHPh | 5-OCH₃ | 8-OCH₃ | 4-pyridyl | pyridazinyl (N=N) | |
| 317 | =O | NPh | C=O | H | 8-OEt | 2-pyridyl | 2-pyridyl | |
| 318 | H₂ | NCOCH₃ | CHCH₃ | H | 7-OCH₃ | | | |
| 319 | H₂ | NCOPh | CHPh | 6-OCH₃ | H | | | |
| 320 | =O | O | C=O | H | H | | | |
| 321 | =O | O | CH₂ | H | H | | | |
| 322 | H₂ | NCOCH₃ | CHPh | H | 7-Ph | | | |
| 323 | H₂ | NCOPh | CHPh | 5-CH₃ | 8-CH₃ | | | |

EXAMPLE 324

3,3-Bis(4-pyridinylmethyl)-naphtho[1,8-b,c]pyran-2-one

To a solution of naphtho[1,8-b,c]pyran-2(3H)-one [prepared according to O'Brien and Smith, *J. Chem. Soc.*, 2907-17 (1963)], (1.842 g, 10 mmol) and picolyl chloride (30.5 mmol, freshly prepared by basifying 5.0 g of the hydrochloride) in chloroform (50 ml) was added benzyltriethylammonium chloride (6.83 g, 30 mmol) and potassium carbonate (4.15 g, 30 mmol). The mixture was heated at 50° for 5 hr., then cooled to room temperature. Water (15 ml) was added, and the mixture was extracted several times with chloroform. After drying over magnesium sulfate, the solvent was removed by rotary evaporation to give a green-black oil. The crude product was purified via column chromatography (silica gel, 5% methanol/ethyl acetate) and recrystallized from hexane/dichloromethane to give a pale yellow solid, 1.459 g, 3.98 mmol, 40% yield. Further recrystallization from ethyl acetate/hexane provided off-white crystals of the title compound, m.p. 166°-7°. NMR (200 MHz, CDCl₃) δ 3.40 (d, 2H, J=13 Hz); 3.84 (d, 2H, J=13 Hz); 6.70 (d, 4H, J=6 Hz); 6.73 (m, 1H); 7.23 (m, 1H); 7.47 (d, 1H, J=8 Hz); 7.65 (d, 2H, J=5 Hz); 7.77 (dd, 1H, J=5,8 Hz); 8.18 (d, 4H, J=6 Hz). IR (KBr) 3033, 1746, 1636, 1601 cm⁻¹. Mass spec. 366. Analysis. Calcd. for $C_{24}H_{18}N_2O_2$: C, 78.67; H, 4.95; N, 7.65. Found: C, 78.46; H, 5.08; N, 7.64.

The compound of Example 324, and the other compounds which may be prepared by the methods described above, are illustrated in Table VII. The table is intended to illustrate, but not to limit its breadth.

TABLE VII
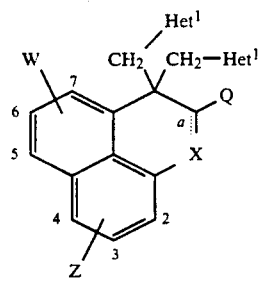
| Ex. | Q | a | X | W | Z | Het¹ | Het² | mp °C. |
|---|---|---|---|---|---|---|---|---|
| 324 | =O | S | O | H | H | 4-pyridyl | 4-pyridyl | 166–167 |
| 325 | =O | S | NH | H | H | 4-pyridyl | 4-pyridyl | |
| 326 | =O | S | NPh | H | H | 4-pyridyl | 4-pyridyl | |
| 327 | =O | S | CH₂ | H | H | 4-pyridyl | 4-pyridyl | |
| 328 | Ph | D | CH | H | H | 4-pyridyl | 4-pyridyl | |
| 329 | (H)Ph | S | CH₂ | H | H | 4-pyridyl | 4-pyridyl | |
| 330 | (H)—OH | S | CH₂ | H | H | 4-pyridyl | 4-pyridyl | |
| 331 | (H)OCOCH₃ | S | CH₂ | H | H | 4-pyridyl | 4-pyridyl | |
| 332 | =N—OCH₃ | S | CH₂ | H | H | 4-pyridyl | 4-pyridyl | |
| 333 | =N—OH | S | CH₂ | H | H | 4-pyridyl | 4-pyridyl | |
| 334 | =S | S | CH₂ | H | H | 4-pyridyl | 4-pyridyl | |

TABLE VII-continued

| Ex. | Q | a | X | W | Z | Het¹ | Het² | mp °C. |
|---|---|---|---|---|---|---|---|---|
| 335 | =S | S | O | H | H | 4-pyridyl | 4-pyridyl | |
| 336 | | S | CH₂ | H | H | 4-pyridyl | 4-pyridyl | |
| 337 | | S | CH₂ | H | H | 4-pyridyl | 4-pyridyl | |
| 338 | | S | CH₂ | H | H | 4-pyridyl | 4-pyridyl | |
| 339 | | S | CH₂ | H | H | 4-pyridyl | 4-pyridyl | |
| 340 | H₂ | S | CH₂ | H | H | 4-pyridyl | 4-pyridyl | |
| 341 | (H)CHF | S | CH₂ | H | H | 4-pyridyl | 4-pyridyl | |
| 342 | F₂ | S | CH₂ | H | H | 4-pyridyl | 4-pyridyl | |
| 343 | =CH₂ | S | CH₂ | H | H | 4-pyridyl | 4-pyridyl | |
| 344 | =CHCH₃ | S | CH₂ | H | H | 4-pyridyl | 4-pyridyl | |
| 345 | =CHPh | S | CH₂ | H | H | 4-pyridyl | 4-pyridyl | |

TABLE VII-continued
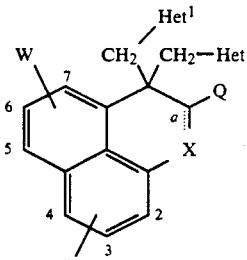
| Ex. | Q | a | X | W | Z | Het[1] | Het[2] | mp °C. |
|-----|---|---|---|---|---|--------|--------|--------|
| 346 | (H)C(H)—Ph(OH) | S | CH$_2$ | H | H | 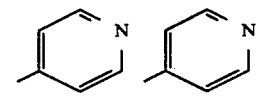 | 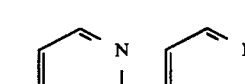 | |
| 347 | —OCH$_3$ | D | CH | H | H | 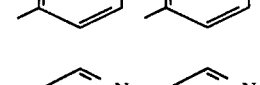 | 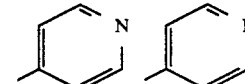 | |
| 348 | —OC$_2$H$_5$ | D | CH | H | H | 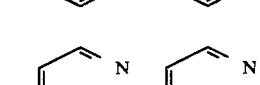 | 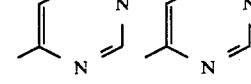 | |
| 349 | =O | S | O | H | H | 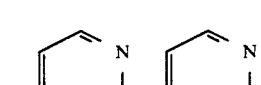 | 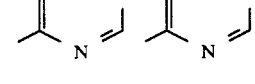 | |
| 350 | =O | S | NPh | H | H | 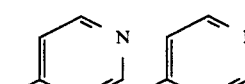 | 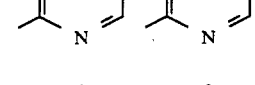 | |
| 351 | =O | S | CH$_2$ | H | H | 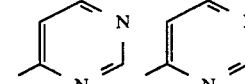 |  | |
| 352 | (H)—OH | S | CH$_2$ | H | H | 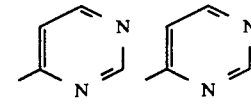 | 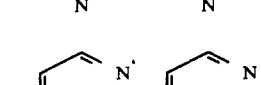 | |
| 353 | =CH$_2$ | S | CH$_2$ | H | H | 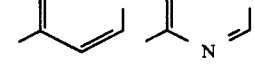 | 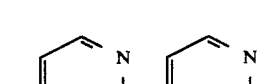 | |
| 354 | =O | S | O | 6-OH | H | 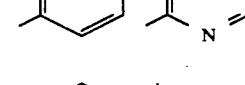 |  | |
| 355 | =O | S | O | 5-OAc | 4-OAc | 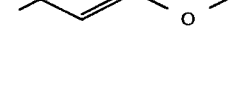 |  | |
| 356 | =O | S | CH$_2$ | H | H |  | | |

TABLE VII-continued

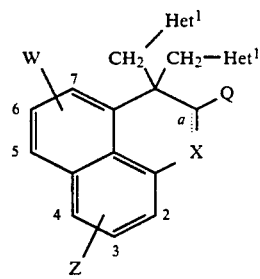

| Ex. | Q | a | X | W | Z | Het¹ | Het² | mp °C. |
|---|---|---|---|---|---|---|---|---|
| 357 | =O | S | CH₂ | H | H | 4-pyridyl | 1H-pyrazol-3-yl | |
| 358 | =O | S | NPh | 5-Br | H | 4-pyridyl | pyridazin-3-yl | |
| 359 | =O | S | O | H | 2-CH₃ | 4-pyridyl | pyrimidin-2-yl | |
| 360 | =O | S | O | 7-NO₂ | H | 4-pyridyl | tetrahydrofuran-3-yl | |
| 361 | =O | S | NH | 5-OH | H | pyrimidin-4-yl | tetrahydrofuran-3-yl | |
| 362 | =O | S | NPh | 5-Cl | 4-Cl | 4-pyridyl | thien-3-yl | |
| 363 | =O | S | NCH₃ | 7-CH₃ | 2-CH₃ | 4-pyridyl | tetrahydrofuran-2-yl | |
| 364 | =O | S | NPh | H | H | 2-pyridyl | 4-pyridyl | |
| 365 | =O | S | O | 5-Cl | 4-Cl | 4-pyridyl | pyridazin-4-yl | |
| 366 | =O | S | NH | 7-CH₃ | H | 2-pyridyl | 2-pyridyl | |

TABLE VII-continued

| Ex. | Q | a | X | W | Z | Het¹ | Het² | mp °C. |
|---|---|---|---|---|---|---|---|---|
| 367 | =O | S | O | 5-NH₂ | H | 4-pyrimidinyl | 4-pyrimidinyl | |
| 368 | =CH₂ | S | CH₂ | H | H | 4-pyridyl | 3-tetrahydrofuranyl | |
| 369 | =CHPh | S | CH₂ | H | H | 4-pyridyl | 3-thienyl | |
| 370 | =CHCH₃ | S | CH₂ | H | H | 4-pyridyl | 2-pyrimidinyl | |
| 371 | —OCH₃ | D | CH | H | H | 4-pyridyl | 2-tetrahydrofuranyl | |
| 372 | =N—OCH₃ | S | CH₂ | H | H | 4-pyridyl | 3-pyridazinyl | |
| 373 | H₂ | S | CH₂ | H | H | 4-pyrimidinyl | 2-tetrahydrofuranyl | |
| 374 | H | D | CH | H | H | 4-pyridyl | 5-pyrimidinyl | |
| 375 | (H)OH | S | CH₂ | H | H | 4-pyridyl | 2-pyrimidinyl | |
| 376 | (H)OAc | S | CH₂ | H | H | 4-pyridyl | 3-pyridazinyl | |

TABLE VII-continued

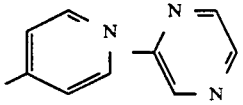

| Ex. | Q | a | X | W | Z | Het¹ | Het² | mp °C. |
|---|---|---|---|---|---|---|---|---|
| 377 | =S | S | CH₂ | H | H | 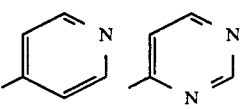 | 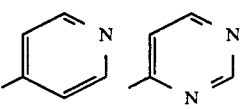 | |
| 378 | =S | S | NPh | 5-NO₂ | H |  | 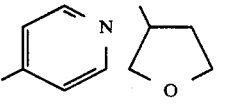 | |
| 379 | =N—OH | S | CH₂ | H | H |  | 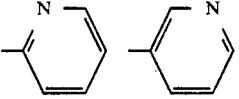 | |
| 380 | | S | CH₂ | H | H |  | 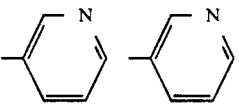 | |
| 381 | | S | CH₂ | 5-Br | H |  | 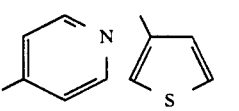 | |
| 382 | | S | CH₂ | 5-Cl | 4-Cl |  | 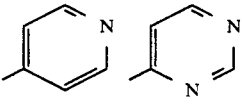 | |
| 383 | F₂ | S | CH₂ | 5-OAc | 4-OAc |  | 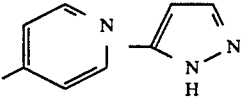 | |
| 384 | Ph | D | CH | H | H |  | 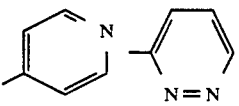 | |
| 385 | (H)Ph | S | CH₂ | H | H |  | | |

EXAMPLE 386

11,11-Bis(4-pyridinylmethyl)-5H-dibenzo[a,d]cyclohepten-10(11H)-one, dihydrochloride To a suspension of sodium hydride (60% oil dispersion, 1.6 g, 0.04 mol) in 30 ml of dry 1,2-dimethoxyethane was added a solution of 5,11-dihydro-10H-dibenzo[a,d]cyclohepten-10-one [Leonard, et. al., J. Am. Chem. Soc. 77, 5078 (1955)], (4.16 g, 0.02 mol) in 30 ml of dry 1,2-dimethoxyethane dropwise. After all the ketone was added, the mixture was gently heated at reflux for 1 hr. A solution of 4-picolyl chloride was prepared by dissolving 4-picolyl chloride hydrochloride (6.56 g, 0.04 mol) in 100 ml of water, basifying the solution with sodium bicarbonate, and extracting the free base into ether (200 ml). After drying over sodium sulfate, the mixture was filtered, and the ether was removed by rotary evaporation. The residue was immediately redissolved in 1,2-dimethoxyethane (30 ml). This solution was added dropwise to the hot reaction mixture, and the mixture was heated at reflux for 6 h. The reaction mixture was cooled, and methanol (10 ml) was added to decompose excess sodium hydride. The solvents were evaporated, and the residue was dissolved in 200 ml of dichloromethane. The organic phase was washed with water and dried over sodium sulfate. After filtration and rotary evaporation, the crude product was purified by column chromatography (silica gel, 10% methanol/dichloromethane). The product thus obtained was a thick oil. NMR (200 MHz, CDCl$_3$) δ 3.43–3.49 (d, 1H); 3.76–3.82 (d, 1H); 4.16–4.49 (d, 1H); 4.86–4.93 (m, 2H); 7.02–7.88 (m, 8H); 8.52 (d, 2H); 8.55 (d, 2H). IR (neat) 1675, 1598 cm$^{-1}$.

The oil was dissolved in ether and treated with ethereal hydrogen chloride to give the title dihydrochloride salt as an amorphous, hydroscopic solid, m.p. >300°.

The compound of Example 386, and other compounds which can be prepared by the methods described above, are illustrated in Table VIII. The table is intended to illustrate the invention, but not to limit its breadth.

TABLE VIII

| Ex. | Q  | A        | W      | Z      | Het$^1$   | Het$^2$   | mp °C. |
|-----|----|----------|--------|--------|-----------|-----------|--------|
| 386 | =O | CH$_2$CH$_2$ | H      | H      | 4-pyridyl | 4-pyridyl | >300   |
| 387 | =O | CH$_2$   | H      | H      | 4-pyridyl | 4-pyridyl | >300   |
| 388 | =O | CH$_2$   | 8-Cl   | H      | 4-pyridyl | 4-pyridyl |        |
| 389 | =O | CHCH$_3$ | H      | H      | 4-pyridyl | 4-pyridyl |        |
| 390 | =O | O        | 8-OCH$_3$ | H   | 4-pyridyl | 4-pyridyl |        |
| 391 | =O | NC$_2$H$_5$ | H   | H      | 4-pyridyl | 4-pyridyl |        |
| 392 | =O | S        | H      | 3-Cl   | 4-pyridyl | 4-pyridyl |        |
| 393 | =O | O        | 9-F    | 3-Cl   | 4-pyridyl | 4-pyridyl |        |
| 394 | =O | S        | H      | 1-OCH$_3$ | 4-pyridyl | 4-pyridyl |        |

TABLE VIII-continued
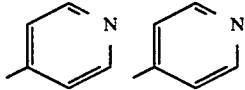
| Ex. | Q | A | W | Z | Het¹ | Het² | mp °C. |
|---|---|---|---|---|---|---|---|
| 395 | =O | NCH₂Ph | H | H | 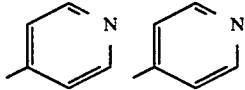 | 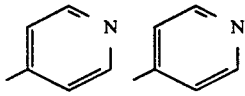 | |
| 396 | =CH₂ | O | H | H | 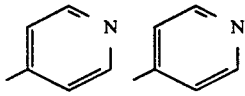 | 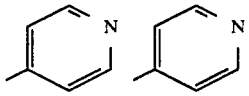 | |
| 397 | =CH₂ | S | H | H | 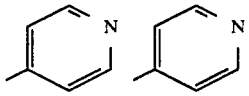 | 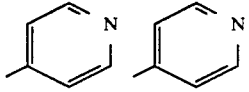 | |
| 398 | =CH₂ | NC₂H₅ | H | H | 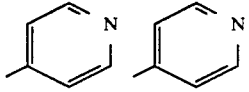 | 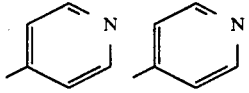 | |
| 399 | =CHPh | CH₂ | 8-Cl | H | 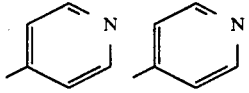 | 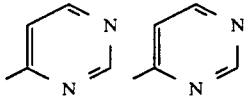 | |
| 400 | =O | S | H | 2-CH₃ | 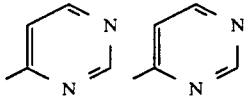 | 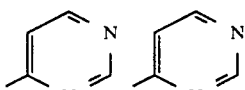 | |
| 401 | —OH | S | H | 1-CH₃ | 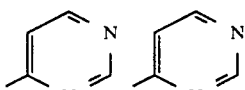 | 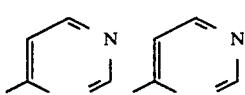 | |
| 402 | =CH₂ | S | 8-I | 3-iPr | 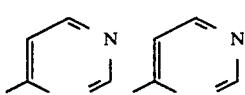 |  | |
| 403 | =O | O | H | 2-F |  | 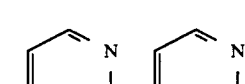 | |
| 404 | =O | NH | 9-Cl | 2-Cl | 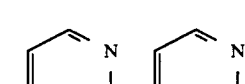 | 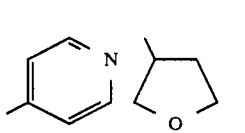 | |
| 405 | =CHPh | S | H | 2-OCH₃ | 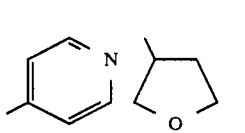 | | |

TABLE VIII-continued

| Ex. | Q | A | W | Z | Het¹ | Het² | mp °C. |
|---|---|---|---|---|---|---|---|
| 406 | —OCOCH₃ | NCH₃ | H | H | 4-pyridyl | 3-tetrahydrofuranyl | |
| 407 | =O | O | 8-NO₂ | 1-OCH₃ | 4-pyridyl | 3-tetrahydrofuranyl | |
| 408 | =O | CH₂ | H | 2,3-di-OCH₃ | 4-pyridyl | 3-tetrahydrofuranyl | |
| 409 | =CH₂ | CH₂ | H | H | 4-pyridyl | 4-pyrimidinyl | |
| 410 | =CHPh | O | H | 2-F | 4-pyrimidinyl | 3-tetrahydrofuranyl | |
| 411 | —CH₂Ph | NCH₂Ph | H | H | 4-pyridyl | 3-pyrazolyl | |
| 412 | —OH | N-iPr | H | H | 4-pyridyl | 4-pyrimidinyl | |
| 413 | —OCOCH₃ | S | 8-Ac | H | 3-pyridyl | 3-pyridyl | |
| 414 | =O | S | H | 3-CH₂CO₂Et | 4-pyridyl | 4-pyrimidinyl | |
| 415 | =O | O | H | 3-Br | 4-pyridyl | 3-pyridazinyl | |
| 416 | O | O | H | 3-NO₂ | 4-pyridyl | 5-pyrimidinyl | |

TABLE VIII-continued

| Ex. | Q | A | W | Z | Het¹ | Het² | mp °C. |
|---|---|---|---|---|---|---|---|
| 417 | =CHPh | O | H | 3-NH$_2$ | 4-pyridyl | tetrahydrofuran-2-yl | |
| 418 | —OCOCH$_3$ | S | H | 2-I | 4-pyridyl | thien-3-yl | |
| 419 | =O | NCH$_3$ | H | H | 4-pyridyl | tetrahydrofuran-2-yl | |
| 420 | =CH$_2$ | O | H | 3-C$_2$H$_5$ | 4-pyrimidinyl | tetrahydrofuran-2-yl | |
| 421 | (Ph)(OH) | CH$_2$ | H | 2,3-di-OAc | 3-thienyl | 4-pyrimidinyl | |
| 422 | =O | S | H | —OCH$_3$ | 4-pyridyl | 1H-pyrazol-3-yl | |
| 423 | =CHPh | S | 8-Ac | H | 4-pyridyl | 2-pyrimidinyl | |
| 424 | =O | O | 9-F | 3-Cl | 4-pyridyl | pyridazin-3-yl | |
| 425 | —OCOCH$_3$ | O | 8-NO$_2$ | 1-OCH$_3$ | 2-pyridyl | 2-pyridyl | |
| 426 | =CH$_2$ | CH$_2$CH$_2$ | H | H | 4-pyridyl | 4-pyridyl | |
| 427 | —OCOCH$_3$ | CH$_2$CH$_2$ | H | H | 4-pyridyl | tetrahydrofuran-3-yl | |

TABLE VIII-continued

| Ex. | Q | A | W | Z | Het¹ | Het² | mp °C. |
|---|---|---|---|---|---|---|---|
| 428 | =CH₂ | —(CH₂)₃— | H | H | 4-pyridyl | 4-pyrimidinyl | |
| 429 | =CHPh | CH₂ | 8-Cl | H | 4-pyridyl | 3-pyridazinyl | |
| 430 | =O | —(CH₂)₃— | H | H | 4-pyridyl | 2-pyrimidinyl | |
| 431 | —OH | —(CH₂)₃— | H | H | 4-pyridyl | 3-(1H-pyrazolyl) | |
| 432 | =O | S | H | 1-C₂H₅ | 4-pyridyl | 3-pyridazinyl | |
| 433 | =CHPh | S | H | 3-I | 4-pyridyl | 3-thienyl | |
| 434 | =CHCH₃ | O | H | 3-NO₂ | 4-pyridyl | 2-tetrahydrofuryl | |
| 435 | =CH₂ | CH₂ | 8-Cl | H | 4-pyridyl | 5-pyrimidinyl | |
| 436 | =O | (CH₂)₀ | H | H | 4-pyridyl | 4-pyridyl | |
| 437 | =O | (CH₂)₀ | H | H | 4-pyrimidinyl | 4-pyrimidinyl | |
| 438 | =CH₂ | (CH₂)₀ | H | H | 4-pyridyl | 3-tetrahydrofuryl | |

TABLE VIII-continued

[Structure diagram: Het¹—CH₂ and Het²—CH₂ both attached to a carbon bearing Q, connected to a tricyclic aromatic system with bridging group A, positions labeled 1-8, with W at position 6/7 and Z at position 2/3]

| Ex. | Q | A | W | Z | Het¹ | Het² | mp °C. |
|-----|-----|-------|---|---|------|------|--------|
| 439 | =CH₂ | (CH₂)₀ | H | H | pyridinyl (N) | thienyl (S) | |

EXAMPLE 440

9,9-Bis(4-pyridinylmethyl)anthrone

A quantity of 35.2 ml (0.44 mole) of 12.5N sodium hydroxide was added dropwise with vigorous stirring during one hour to a mixture of 19.4 g (0.1 mole) of anthrone, 4.5 g (0.02 mole) of benzyltriethyl ammonium chloride, 33.5 g (0.2 mole) of 4-picolylchloride hydrochloride and 200 ml of toluene. During the addition, the temperature rose to 50°. After completion of addition, the mixture was vigorously stirred at 60° for six hours. Then 200 ml of water was added in one portion, the layers were separated and product crystallized out of the toluene layer as it cooled to room temperature. After cooling in an ice bath, the solid was filtered, washed with water, taken through an acid-base wash, and decolorized with 35 g of Magnesol ® to yield 28 g of product, melting at 205°-206°. This was recrystallized from toluene (1.0 g/22.0 ml toluene) to yield 21 g of title product melting at 207°-208°.

EXAMPLE 441

9,9-Bis(4-pyridinylmethyl)anthrone dihydrochloride

A quantity of 3 ml of 25% hydrochloric acid in ethanol was added to a solution of 2.0 g of 9,9-bis(4-pyridinylmethyl)anthrone in 10 ml of ethanol plus 5 ml of isopropanol. The solution was heated briefly to boiling and allowed to cool, during which time the product crystallized out as colorless crystals. After cooling at 0° for one hour, the crystals were filtered off, washed with a small amount of isopropanol, and recrystallized from ethanol isopropanol to yield 2.0 g of the title product, m.p. 275°-277°.

EXAMPLE 442

9,9-Bis(4-pyridinylmethyl)xanthane

An amount of 5.1 g (0.028 mole) of xanthene was dissolved in 50 ml of dry tetrahydrofuran and cooled to −30°. 3.11 g (0.029 mole) of lithium diisopropylamide was weighed into a dropping funnel and dissolved in 30 ml of tetrahydrofuran. This solution was added dropwise during 30 minutes to the xanthane solution at −30°. After completion of addition, the reaction was warmed to room temperature and kept there for 15 minutes. It was recooled to −30° and 5.05 g (0.03 mole) of 4-picolylchloride in 15 ml of tetrahydrofuran was added dropwise during 30 minutes at −30°. After completion of addition, the reaction mixture was warmed to room temperature and kept there for 30 minutes. Again the reaction was cooled to −30° and a further batch of 3.11 g (0.029 mole) of lithium diisopropylamide in 30 ml of tetrahydrofuran was added dropwise during 30 minutes at −30°. After completion of addition, it was warmed to room temperature and kept there for 15 minutes. After cooling again to −30°, a further quantity of 4-picolylchloride (0.03 mole) in 15 ml of tetrahydrofuran was added dropwise during 30 minutes at −30°. After completion of addition, the reaction mixture was warmed to room temperature and kept there until thin layer chromatography showed completion of reaction, about ten hours. Excess anion was carefully destroyed by the addition of 50 ml of saturated ammonium chloride solution and the tetrahydrofuran was evaporated in vacuo. The residue was taken up in methylene chloride and product was extracted with 3×100 ml of 0.5N hydrochloric acid. The combined hydrochloric acid portions were made basic with 50% sodium hydroxide to ph 12 and the product was extracted with methylene chloride. The methylene chloride extracts were combined, washed with water, dried (MgSO₄), filtered and evaporated. The crude product was triturated with ether to produce 2.0 g of product. This material was chromatographed on silica with hexane/ethylacetate (70:30). Fractions containing product were combined and evaporated to yield 1.7 g of disubstituted product. This was recrystallized from chlorobutane to yield 1.1 g, m.p. 212°-213°, of titled dialkylated xanthane.

EXAMPLE 443

9,9-Bis(4-pyridinylmethyl)fluorine

A quantity of 3.0 g (18.0 mole) of fluorene was dissolved in 20 ml of tetrahydrofuran (THF) and cooled to −20° under nitrogen. n-Butyllithium (11.5 ml, 1.57M) was added dropwise during 15 minutes. After stirring for 30 minutes, this was cannulated into a solution of 18.0 mmole of 4-picolylchloride in 20 ml of THF at −78°. After allowing the reaction to warm to room temperature, thin layer chromatography (TLC) (ether-hexane 1:1) showed disappearance of fluorene. The reaction was cooled again to −20° and a second batch of 11.5 ml of n-butyllithium (1.57M) was added dropwise during 15 minutes. After stirring for 30 minutes, this reaction mixture was cannulated into a solution of 18.0 mmole of 4-picolylchloride in 20 ml of THF at −78°. The resulting mixture was allowed to warm to room temperature and stirred at ambient temperature overnight (17 hours). The reaction was quenched with saturated ammonium chloride and extracted with ether. The crude combined extracts were chromatographed with methylene chloride/methanol (30:1) to (25:1) yielding 2.9 g of pure title dialkylated fluorene. HRMS: 348.1615 (M+), 256.1131 (M-C$_6$H$_6$N).

EXAMPLE 444

2-Nitro-9,9-Bis(4-pyridinylmethyl)fluorene

A quantity of 0.5 g (2.37 mmole) of 2-nitrofluorene, 0.86 g (5.2 mmole) of 4-picolylchloride hydrochloride, 60 mg of cetyl tri-n-butyl phosphonium bromide and 10 ml of toluene were combined and heated to 50°. With vigorous stirring 5.0 ml of 50% sodium hydroxide was added dropwise at 50° during 30 minutes. Heating was continued for one hour. A quantity of 10 ml of water was added, the reaction cooled to room temperature and partitioned with methylene chloride. The combined organic layer was extracted with 3×25 ml of 0.5N HCl and the combined aqueous extracts basified with sodium hydroxide. The precipitated product was chromatographed (silica, methylene chloride/methanol 100:1) to yield 0.6 g of the title product, m.p. 260°–264°. HRMS-measured, 393.1465; calculated, 393.1477; assigned, C$_{25}$H$_{19}$N$_3$O$_2$(M+).

The dialkylated fluorene was converted to its dihydrochloride salt by dissolving 0.5 g of the base in ethanol and adding 2 ml of 25% hydrochloric acid in ethanol. Addition of ether produced product, which was recrystallized from methanol/ethyl acetate to yield 0.4 g, m.p., >300°.

EXAMPLE 445

9,9-Bis(4-pyridinylmethyl)thioxanthene

Part A: 9-(4-pyridinylmethyl)thioxanthene

A quantity of 4.96 g (0.025 mole) of thioxanthane was dissolved in 25 ml of tetrahydrofuran (THF) and cooled to −20°. With stirring, 18 ml of a 1.4M solution of potassium hexamethyldisilazide was added dropwise during 30 minutes. After completion of addition, the reaction mixture was warmed to room temperature and it was kept there for 15 minutes. It was then cooled to −20° and a solution of 4-picolylchloride (28.0 mmoles) base in 20 ml of THF was added dropwise during 30 minutes at −20°. After addition, the reaction mixture was warmed to room temperature and kept there for one hour. The reaction was quenched with 50 ml saturated ammonium chloride and evaporated. The residue was extracted with methylene chloride, put through an acid-base sequential wash with 0.5N hydrochloric acid and 50% sodium hydroxide. The organic layer was dried (MgSO$_4$) and evaporated to yield 5.1 g of the titled monoalkylated product.

Part B: 9,9-Bis(4-pyridinylmethyl)thioxanthene

A quantity of 0.38 g (8.0 mmole) of 50% sodium hydride oil dispersion was added slowly during 15 minutes to 20 ml of dimethyl sulfoxide at room temperature. After completion of addition, the reaction mixture was heated at 45° for 30 minutes. It was cooled to 15° and a solution of 2.3 g (8.0 mmole) of 9-(4-pyridinylmethyl)-thioxanthene in 10 ml of dimethylsulfoxide was added dropwise during 15 minutes at room temperature. After completion of addition, the reaction mixture was stirred 30 minutes at room temperature. Then a solution of 4-picolylchloride (8.75 mmole) in 5 ml of dimethylsulfoxide was added dropwise during 30 minutes at ambient temperature. The reaction was then heated at 40° for 30 minutes. The reaction was quenched by addition of water (50 ml). Trituration of the precipitated oil yielded a crystalline solid, which was filtered off, washed with water and dried. The tan solid was dissolved in benzene and decolorized by stirring with 1 g of Magnesol® for 30 minutes. Filtration and evaporation yielded a colorless product (2.0 g) which was recrystallized from ethylacetate, m.p., 201.4°–203.4°.

EXAMPLE 446

9,9-Bis(4-pyridinylmethyl)-1-methylfluorene dihydrochloride

The title compound was prepared following the procedure of Example 5 from 0.5 g (2.77 mmole) of 1-methylfluorene, 1.0 g of picolylchloride hydrochloride, 4 ml sodium hydroxide (50% solution), 68 mg of cetyl-tri-n-butyl phosphonium bromide, and 4 ml toluene by reaction at 50° for 1 hr. The product was chromatographed (silica, CH$_2$/Cl$_2$CH$_3$OH, 100:1), m.p. (dihydrochloride) >300°, NMR (200 MHz, CDCL$_3$) δ: 2.82(s,3H), 3.60(dd,4H), 6.39(m,4H), 7.0–7.5(m,7H-arom.), 8.0(m,4H). HRMS calculated for C$_{26}$H$_{22}$N$_2$: 362.1783 Found: 362.1779

EXAMPLE 447

9,9-Bis(4-pyridinylmethyl)-2-bromofluorene dihydrochloride

The title compound was prepared following the procedure of Example 5 from 1.0 g (4.08 mmole) of 2-bromofluorene, 1.5 g of 4-picolylchloride hydrochloride, 100 mg of cetyl tri-n-butyl phosphonium bromide, 20 ml of 50% sodium hydroxide solution, and 20 ml toluene by reaction at 50° for 1 hr. The product was chromatographed (silica, CH$_2$Cl$_2$/CH$_3$OH, 100:1), m.p. (dihydrochloride) >300° NMR (200 MHz,CDCL$_3$) δ: 3.39(dd,4H), 6.48(d,4H), 7.10–7.67 (m,7H-arom.), 8.12(d,J=5.7 Hz,4H). HRMS calculated for C$_{25}$H$_{19}$BrN$_2$: 426.0758 Found: 426.0758

EXAMPLE 448

9,9-Bis(4-pyridinylmethyl)-2-aminofluorene 1.68 g (4.27 mmole) of 9,9-bis(4-pyridinylmethyl)-2-nitrofluorene was suspended in 5 ml of ethanol/water (1:1) and 1.43 g of powdered iron was added. The mixture was heated to boiling and 0.3 ml conc. hydrochloric acid was added dropwise. After completion of addition, the mixture was refluxed 2 hrs. The cooled mixture was basified with KOH, iron hydroxide filtered off and the filtrate evaporated. The residue was dissolved in ether-CH$_2$Cl$_2$ (3:1), washed with water, saturated sodium chloride, dried (MgSO$_4$) and evaporated to yield 1.28 g of the title product. NMR (CDCl$_3$, 200 MHz) δ: 3.33(s,4H), 6.53(dd,4H), 6.60(d,J=2.0 Hz,1H), 6.79(d,J=2.0 Hz,1H), 7.18(d,4H), 7.37(dd,1H), 8.11(dd,4H), m.p. (trihydrochloride) >300°. HRMS calculated for C$_{25}$H$_{21}$N$_3$: 363.1735 Found: 363.1728.

EXAMPLE 449

9,9-Bis(4-pyridinylmethyl)-2-acetamido-fluorene dihydrochloride 0.38 g of 9,9-bis(4-pyridinylmethyl)-2-aminofluorene was added to 4 ml acetic anhydride and heated at 70° overnight. The reaction was quenched into a pH 7 buffer and extracted with ethyl acetate. Following an acid-base wash, the product was chromatographed (silica, CH₂Cl₂/MeOH, 10:1) to yield 0.3 g after conversion to the dihydrochloride, m.p., >300°.

EXAMPLE 450

9,9-Bis(4-pyridinylmethyl)-2-acetylfluorene dihydrochloride

The title compound was prepared following the procedure of Example 1 from 5.0 g (24 mmole) of 2-acetylfluorene, 10 g of 4-picolylchloride hydrochloride, 120 ml benzene, 200 mg of benzyltriethylammonium chloride, and 20 ml of 50% sodium hydroxide by reaction solution at 20° for 17 hrs. The title compound was obtained after an acid-base wash and crystallization from benzene-hexane (Magnesol®), m.p., >300°. NMR (CDCl₃, 200 MHz) δ: 2.68(S,3H), 3.46(S,4H), 6.44(d,J=5.9 Hz,4H), 7.29–7.87(m,6H), 8.05(d,J=5.9 Hz,4H), 8.22(d,1H). HRMS calculated for C₂₇H₂₂N₂O: 390.1732 Found: 390.1720.

EXAMPLE 451

9,9-Bis(4-pyridinylmethyl)-2-fluorofluorene dihydrochloride

The title compound was prepared following the method of Example 1 from 4.0 g (21.74 mmole) of 2-fluorofluorene, 8.92 g of 4-picolylchloride hydrochloride, 120 ml of toluene, 200 mg of benzyltriethylammonium chloride, and 20 ml of 50% sodium hydroxide by reaction at 22° for 17 hrs. The product was chromatographed (silica, CH₂Cl₂/MeOH, 10:1) to yield 2.9 g which was recrystallized (ethanol-acetone) and converted to the dihydrochloride, m.p. >300°.

EXAMPLE 452

9,9-Bis(4-pyridinylmethyl)-2-difluoromethyl fluorene

The title compound was prepared following the method of Example 1 from 0.6 g (2.78 mmole) of 2-difluoromethylfluorene, 1.14 g of 4-picolylchloride hydrochloride, 32 mg benzyltriethylammonium chloride, 4 ml of 50% sodium hydroxide solution, and 25 ml of toluene by reaction at 50° for 6 hrs. The product was chromatographed (silica, CH₂Cl₂/MeOH, 10:1) to yield 0.5 g, m.p. >300°; NMR (CDCl₃,200 MHz) δ: 3.43(S,4H), 6.45(d,J=5.7 Hz,4H), 6.74(t,J=56.6 Hz,1H), 7.26–7.70(m.arom.), 8.1(d,J=5.7 Hz,4H). HRMS calculated for C₂₆H₂₀N₂F₂: 398.1595 Found: 398.1583.

EXAMPLE 453

9,9-Bis(4-pyridinylmethyl)-2-(1-hydroxyethyl)fluorene

To 300 mg of 9,9-bis(4-pyridinylmethyl)-2-acetylfluorene was dissolved in 5 ml of ethanol cooled to 0° was added 100 mg of sodium borohydride. The reaction mixture was warmed to room temperature overnight, quenched with water and methanol and the solvents evaporated. The residue was partitioned between ethyl acetate and 1N NaOH, washed with water, brine, dried (MgSO₄) and evaporated. Recrystallization from ethanol yielded product. NMR (CDCl₃, 200 MHz) δ: 1.50(d,J=6.5 Hz, 3H), 3.39(s,4H), 4.92(q,J=6.4 Hz, 1H), 6.43(2d,4H), 7.08–7.58(m, arom.), 7.87(d,2H), 7.97(d,2H).

EXAMPLE 454

9,9-Bis(4-pyridinylmethyl)-2-methylfluorene

The title compound was prepared following the procedure of Example 5 from 0.95 g of 2-methylfluorene, 2.17 g of 4-picolychloride hydrochloride, 50 mg of cetyl(Bu)₃PBr, 30 ml toluene, and 5 ml 50% NaOH by reaction at 50° for 6 hrs. The material was chromatographed to yield 0.2 g product. NMR (CDCl₃,200 MHz) δ: 2.47(s,3H), 3.37(s,4H), 6.49(d,J=5.3 Hz,4H), 7.03–7.45(arom.H), 8.09(d,4H). HRMS calculated for C₂₆H₂₂N₂: 362.1783 Found: 362.1778

EXAMPLE 455

9,9-Bis(4-pyridinylmethyl)-2-ethylfluorene

The title compound was prepared following the procedure described in Example 5 from 2.39 g (12.32 mmole) of 2-ethylfluoroene, 4.0 g of 4-picolylchloride .HCl, 110 mg of cetyl Bu₃PBr, 20 ml of 50% NaOH, and 30 ml of toluene by reaction at 50° for 6 hrs. The product was chromatographed (silica, CH₂Cl₂/MeOH, 95:5) to yield 2.0 g of product. NMR (CDCl₃, 200 MHz) δ: 1.30(t,J=7.8 Hz, 3H), 2.74(q,J=7.6 Hz,2H), 3.37(s,4H), 6.49(d,J=5.9 Hz,4H), 7.04–7.48(m,arom.7H), 8.09(d,J=5.4 Hz,4H). HRMS calculated for C₂₇H₂₄N₂: 376.1940 Found: 376.1927

EXAMPLE 456

9,9-Bis(4-pyridinylmethyl)-2-methoxyfluorene dihydrochloride

The title compound was prepared following the procedure of Example 5 from 1.8 g (9.2 mmole) of 2-methoxyfluorene, 3.0 g of 4-picolylchloride.HCl, 20 ml of 50% NaOH, 100 mg of cetyl Bu₃PBr, and 30 ml of toluene by reaction at 50° for 6 hrs. The material was chramato-graphed to yield 1.6 g of product. δ: 3.37(s,4H), 3.89(s,3H), 6.52(broad,4H), 6.80(m,1H), 7.01(d,J=2.1 Hz,1H), 7.26(m,5H), 7.45(d,J=7.5 Hz,1H), 8.11(broad,4H).

EXAMPLE 457

9,9-Bis(3-pyridinylmethyl)fluorene

The title compound was prepared following the procedure described in Example 5 from 10.0 mmole of fluorene, 22.0 mmole of 3-picolylchloride hydrochloride, 2.0 mmole of cetyl tri-n-butyl phosphonium bromide, 20 ml of 50% sodium hydroxide and 40 ml of toluene by reaction at 50° for 6 hrs. The material was chromatographed (silica, CH₂Cl₂/MeOH,95:5) to yield 2.6 g (70%), m.p. 137°–138°. δ: 3.41(s,4H), 6.71–6.97(m,4H), 7.17–7.35(tt,6H), 7.50–7.54(d,J=6.9 Hz, 2H), 7.91(s,2H), 8.12–8.15(d,J=5.4 Hz,2H). HRMS calculated for C₂₅H₂₀N₂: 348.1632 Found: 348.1626

EXAMPLE 458

9,9-Bis(4-pyridinylmethyl)-1,4-dimethylanthrone

The title compound was prepared following the procedure of Example 5 from 9.34 g (42 mmole) of 1,4-dimethylanthrone, 15.1 g (92 mmole) of 4-picolylchloride .HCl, 14 ml of 50% sodium hydroxide, 1.91 g of cetyl tri-n-butyl phosphonium bromide and 40 ml of toluene by reaction at 60° for 6 hrs. to form 2.9 g of monoalkylated anthrone. The monoalkylated product was reacted with dimsyl sodium (prepared from 10 mmole of sodium hydride, 0.48 g, in 20 ml DMSO), and 1.27 g (10 mmole) of 4-picolylchloride base at 40° for 2 hrs. The reaction was quenched with water and chromatographed (silica, CH₂Cl₂/MeOH,10:1) to yield 2.0 g of the title bisalkylated product, m.p. 211°–213°.

EXAMPLE 459

9,9-Bis(4-pyridinylmethyl)-4,5-dichloroanthrone

The title compound was prepared following the procedure of Example 1 from 26.3 g (0.1 mole) of 1,8-dichloroanthrone and 4,5-dichloroanthrone, 32.8 g (0.2 mole) of 4-picolylchloride.HCl, 2.28 g (0.01 mole) of benzyltriethylammonium chloride, 32 ml of 50% sodium hydroxide and 75 ml toluene by reaction at 50° for 6 hrs. The product was chromatographed (silica, $CH_2Cl_2$/MeOH 100:1) to yield 15.7 g, m.p. 170°–172°. NMR ($CDCl_3$,200 MHz) δ: 3.53(s,4H), 6.43(d,4H J=6.1 Hz), 7.33–7.51(m,arom. 6H), 8.3(d,J=6.2 Hz,4H) HRMS calculated for $C_{26}H_{18}N_2OCl_2$: 444.0796 Found: 444.0799. Also isolated from above was 9-(4-pyridinylmethyl)-1,8-dichloroanthrone.

EXAMPLE 460

9,9-Bis(4-pyridinylmethyl)-1,8-dichloroanthrone

The title compound was prepared following the procedure of Example 1 from 9-(4-pyridinylmethyl)-1,8-dichloroanthrone (3.54 g,10 mmole), 1.64 g (10 mmole) of 4-picolylchloride .HCl, 0.23 g of benzyltriethylammonium chloride, 1.6 ml of 50% sodium hydroxide and 30 ml toluene by reaction at 60° for 6 hrs. The product was chromatographed (silica, EtOAc/Hexane, 30:70) to yield 0.5 g of product. δ: 4.66(s,4H), 6.33(d,J=6.1 Hz, 4H), 7.45(t,J=6.6 Hz,2H-arom), 7.79(d,J=7.1 Hz,2H-arom), 8.01(d,J=6.3 Hz,4H), 8.13(d,J=7.1 Hz2H). HRMS calculated for $C_{26}H_{18}N_2OCl_2$: 444.0796 Found: 444.0806.

EXAMPLE 461

9,9-Bis(3-pyridinylmethyl)anthrone

The title compound was prepared following the procedure of Example 1 from 20.0 mmole of anthrone, 44.0 mmole of 3-picolylchloride hydrochloride, 2.0 mmole of benzyl triethylammonium chloride, 40 ml of 50% sodium hydroxide, and 50 ml toluene at 60° for 2 hrs. The product was chromatographed (silica, EtOAc/Hexane, 70:30) to yield 1.43 g of product. NMR ($CDCl_3$,200 MHz) δ: 3.77(s,4H), 6.49(d,J=6.9 Hz,2H-arcm), 6.66(dd,J=7.91,J=4.8 Hz,2H-arom), 7.48(t,J=7.4 Hz,2H-arom),7.56(m,1H), 7.79(t,J=7.3 Hz,2H), 8.03(d,J=7.0 Hz,2H), 8.16(mJ=1.8 Hz,4H). HRMS calculated for $C_{26}H_{20}N_2O$: 376.1584 Found: 376.1573

EXAMPLE 462

9,9-Bis(4-pyridinylmethyl)anthrol

To 5 g of 9,9-Bis(4-pyridinylmethyl)anthrone dissolved in 150 ml ethanol was added 2.5 g (0.066 mmole) of sodium borohydride. Addition was portionwise over 1 hr. at ambient temperature. After completion of addition, the solution was refluxed 12 hrs., then stirred overnight (14 hrs.). The reaction was quenched with water, evaporated and partitioned between methylene chloride and water. The organic layer was washed with water, dried ($MgSO_4$) and evaporated to obtain 4.9 g of title product which was recrystallized from 1-propanol to yield 3.12 g, m.p. 196°–197°.

EXAMPLE 463

9,9-Bis(4-pyridinylmethyl)anthrone oxime

To 2.5 ml ethanol was added 500 mg (1.33 mmole) 9,9-bis(4-pyridinylmethyl)anthrone. To the resulting mixture was added 316 mg (5.3 mmole) of hydroxylamine hydrochloride, followed by 2.5 ml pyridine. The resulting solution was refluxed for 24 hrs. Solvents were evaporated, and the residue was triturated with 10 ml water. The solid obtained was recrystallized from ethanol to yield 300 mg of product, m.p. 226°–227°.

EXAMPLE 464

9,9-Bis(4-pyridinylmethyl)cyclopentadienylphenanthrene

The title compound was prepared following the procedure of Example 1 from 5.0 g (0.0263 m) of cyclopentadienylphenanthrene, 9.51 g (58 mmole) 4-picolylchloride .HCl, 11.1 ml 50% sodium hydroxide, 1.2 g benzyltriethylammonium chloride, and 100 ml toluene by reaction at 50° for 6 hrs. The material was chromatographed (silica, EtOAc/MeOH,95:5) to yield 1.9 g of product, m.p. 201°–202°.

EXAMPLE 532

5,5-Bis(4-pyridinylmethyl)-5H-cyclopenta[2,1-b:3,4-b']dipyridine

The title compound was prepared following the procedure of Example 1 from 0.43 g (2.56 mmole) of 4,5-diazafluorene, 0.84 g of 4-picolylchloride hydrochloride, 29.0 mg of benzyltriethylammonium chloride, 3 ml of 50% sodium hydroxide, and 30 ml toluene by reaction at 50° for 6 hrs. The crude product was chromatographed (Ethylacetate/Methanol, 99:1) and recrystallized from isopropyl alcohol. NMR ($CDCl_3$,200 MHz) δ: 3.42(s,4H), 6.52(d,J=5.7 Hz,4H), 7.33(dd,2H), 7.85(d,2H), 8.16(d,J=5.6 Hz,4H), 8.61(d,2H).

EXAMPLE 560

9,9-Bis(4-pyridinylmethyl)cyclopenta-[1,2-b:4,3-b']dipyridine

Part A: Preparation of 5-methoxy-4,7-phenanthroline

Equipment: 5-liter, multi-neck, round bottom flask fitted with a mechanical stirrer, condenser, thermometer and nitrogen inlet. Provisions should be made so that the flask can be lowered easily into an ice bath at the proper time and then replaced with a heating mantle. To the flask was added 875 ml of water, followed by a solution of 322 g of meta-nitrobenzene sulfonic acid in 828 g of sulfuric acid, keeping the temperature below 40°. Then 161 g (0.68 mole) of 2-methoxy-1,4-phenylenediamine sulfate hydrate was added in one batch with stirring. With strong cooling, 430 g of sulfuric acid was very carefully added with vigorous stirring at a temperature below 50°. Finally, 575 g (6.25 mole) of glycerin was added rapidly through a dropping funnel. The mixture was gently refluxed for 6 hours (boiling point 133°), then cooled to room temperature and poured into 6000 ml of ice and 1000 ml water. The solution was basified to pH 10 with 50% sodium hydroxide, adding more ice if necessary to keep the temperature below 20°. The pH 10 mixture was extracted with chloroform, dried with sodium sulfate and evaporated, yielding 128 g of a black thick oil which soon solidifed. This 5-methoxy-4,7-phenanthroline was taken directly to the next step.

Part B: Hydrolysis of 5-methoxy-4,7-phenanthroline to 4,7-phenanthrolin-5,6-quinone To a 3-liter, multi-neck, round bottom flask was added 641 ml of concentrated sulfuric acid. Next, 385 ml of fuming nitric acid (d=1.5 g/ml) was added, keeping the internal temperature below 40°. Heating 128 g (0.61 mole) of 5-methoxy-4,7-phenanthroline with a heat gun to liquify it makes it possible to add it to the acid mixture through a dropping funnel during about one hour. A flameless heat gun was used to keep the contents of the dropping funnel liquid. After completion of addition, the solution was refluxed 13 hours (bp about 90°). The original black solution gradually changed to a yellow-orange color after 13 hours. The solution was next cooled to room temperature and poured into 5 liters of ice. It was neutralized to pH 4-5 with 50% sodium hydroxide solution, adding additional ice to keep the temperature below 10°. The precipitated 4,7-phenanthrolin-5,6-quinone was filtered off, washed with water and dried in a vacuum oven under nitrogen at 100°. Yield 72.9 g.

Part C: Preparation of 1,8-diazafluoren-9-one

To a solution of 200 ml of 10% sodium hydroxide was added 10 g (47 mmole) of 4,7-phenanthrolin-5,6-quinone. This was heated in a water bath at 70°-80° with magnetic stirring for 2 hours. Then the reaction was cooled in an ice bath and acidified with concentrated hydrochloric acid to pH 4-5, keeping the mixture below 20°. The precipitate of side product, 5,6-dihydroxy-4,7-phenanthroline was filtered off and the filtrate was extracted with 5×50 ml of chloroform. After drying with sodium sulfate, the solvent was evaporated, yielding 2.6 g of 1,8-diazafluoren-9-one, m.p. 233°-234.5°.

Part D: Preparation of 1,8-diazafluorene

Procedure followed in Example 608, Part C:

A quantity of 3.62 g (20 mmoles) of 1,8-diazafluoren-9-one and 3.2 g (0.1 mole) of hydrazine was heated in 30 ml of diethyleneglycol at 100° for 1 hour, then heated rapidly to 200° and kept there for one hour (or until TLC showed the complete disappearance of starting material). Yield 2.6 g.

Part E: Preparation of 9,9-Bis(4-pyridinylmethyl)cyclopenta-[1,2-b:4,3-b']dipyridine The alkylation procedure described in Example 608, Part D, was followed.

1.50 g (8.93 mmole) of 1,8-diazafluorene was alkylated in the presence of 1.07 g (22.3 mmole) of 50% sodium hydride by 3.54 g (21.6 mmole) of 4-picolylchloride in 20 ml of benzene and 10 ml of tetrahydrofuran at 55° until TLC showed the reaction was complete (ethyl acetate methanol—90:10)—product Rf 0.1, starting diazafluorene Rf 0.22.

The reaction was decomposed as usual with saturated ammonium chloride. The crude product was flash chromatographed with ethyl acetate, then recrystallized from acetone. Allowed to crystallize overnight, the pure white crystals were filtered off, washed with a small quantity of cold acetone, and dried to yield 940 mg, m.p. 244°-7°. Rf 0.1.

| HRMS: | Calculated Mass; | Measured Mass |
|---|---|---|
| | 350.1531 | 350.1534 |

Difference 0.0003; for $C_{23}H_{18}N_4$.

NMR(200 MHz) δ:3.796(s,4H,(-$CH_2$-pyridyl); 6.391-6.421 (dd,4H,β-pyridyls); 7.140-7.203(m,2H,3-H and 6-H of 1,8-diazafluorene—e.g., meta to the nitrogens); 7.477-7.523(dd,2H,4-H and 5-H of diazafluorene); 8.006-8.014 (d,4H,α-pyridyls); 8.676-8.709(dd,2H,2-H and 7-H of diazafluorene).

EXAMPLE 608

9,9-Bis(4-pyridinylmethyl)indeno-[2,1-b]pyridine

Part A

A quantity of 47.5 g (0.265 mole) of commercial 4-azaphenanthrene was dissolved in 750 ml glacial acetic acid. With vigorous stirring, 110 g (0.33 mole) of iodine pentoxide was added. The mixture was heated to gentle reflux and kept there for 6 hours.

At the end of this time, the reaction mixture was cooled to room temperature and excess iodine pentoxide was filtered off. The solution was rotary evaporated and the residue was taken up in benzene. This solution was washed with sodium thiosulfate to remove excess iodine. It was then dried with sodium sulfate, filtered and evaporated to yield 20 g of 4-phenanthren-5,6-dione. Recrystallization from ethanol gave 13.0 g of pure dione, m.p. 262°.

Part B: Conversion of 4-azaphenanthren-5,6-dione to 1-azafluoren-9-one.

A solution of 4-azaphenanthren-5,6-dione, 10.76 g (51 mmole) was added to 200 ml of 10% sodium hydroxide in an erlenmeyer flask. This was placed in a bath and heated to 70°-80° for 2 hours. When TLC showed the reaction was finished, it was cooled to room temperature and extracted with chloroform. This was dried with sodium sulfate and evaporated to yield a tan product. Flash chromatography with ethyl acetate yielded 4.79 g, m.p. 129°-130°, of pure 1-azafluoren-9-one.

Part C: Reduction of 1-azafluoren-9-one to 1-azafluorene 4.6 g (25.4 mmole) of 1-azafluoren-9-one was added to a solution of 9 ml (0.28 mole) of hydrazine and 50 ml of diethyleneglycol. Heating was started and the temperature was kept at 100° for 15 minutes, then raised to 195° and kept there for 1 hr. TLC showed the reaction was complete. The reaction solution was cooled to below 100° and poured into 300 ml of ice water. The aqueous phase was saturated with salt and extracted with 8×100 ml ether. The ether was dried with sodium sulfate and evaporated to yield 3.73 g of crude product. This was dissolved in hexane and treated with Magnesol, filtered and evaporated and finally recrystallized from hexane to yield 2.83 g of pure 1-azafluorene.

Part D: Preparation of 9,9-Bis-(4-pyridinylmethyl)indeno[2,1-b]pyridine 2.0 g (42 mmole) of 50% sodium hydride was suspended in a 250 ml, 4-neck, round-bottom flask fitted with nitrogen inlet, condenser, thermometer, addition funnel, magnetic stirrer, and 25 ml of sodium dried tetrahydrofuran (THF) containing 2.5 g (15 mmol) of 1-azafluorene. The mixture was allowed to stir at room temperature for one hour. 6.6 g (40 mmole) of 4-picolylchloride hydrochloride was dissolved in the minimum amount of water and cooled to 0°-5°. Being very careful to keep the temperature below 5°, it was basified with ammonium hydroxide, quickly extracted with benzene, dried with potassium carbonate and filtered. The benzene solution of 4-picolyl chloride was added to the reaction mixture during 15 min. After completion of addition, the mixture was heated to 60° until TLC showed completion of reaction (ETOAc-CH₃OH; 90:10) Rf 0.13. Rf 0.13. The reaction mixture was cooled and decomposed with saturated ammonium chloride solution. The layers were separated and the organic phase extracted with benzene. This was dried with potassium carbonate and evaporated to yield 6.0 g crude product. Flash chromatography (ethyl acetate) yielded 4.0 g of product which was recrystallized from butyl chloride to yield 2.49 g, m.p. 204.7°–206.0°. HRMS calculated mass 349.1528, difference 0.0004, $C_{24}H_{19}N_3$. NMR (200 MHz,CDCl₃) δ 3.394–3.718[dd,4H,(-CH₂-pyridyl]; 6.437(d,4H,β-pyridyls); 7.107–7.635 (m,6H,aromatic); 8.027–8.057(d,4-H,α-pyridyls); 8.589–8.621(dd,1H,α-CHN-azafluorene).

EXAMPLE 611

5,5-Bis(4-pyridinylmethyl)indeno-[1,2-b] pyridine

Part A: Preparation of 1-azaphenanthren-5,6-dione

Following the procedure described in Example 608, Part A, 37.5 g (0.153 mole) of commercial 1-azaphenanthrene, 55 g (0.165 mole) of iodine pentoxide in 600 ml glacial acetic acid were refluxed 2 hours. Identical workup yielded 8.4 g, m.p. 215°–16°.

Part B: Conversion of 1-azaphenanthren-5,6-dione to 4-azafluoren-9-one

Following the procedure described in Example 608, Part B, 8.2 g (0.04 mole) of 1-azaphenanthren-5,6-dione and 165 ml of 10% sodium hydroxide were heated in a bath at 80°–90° for 3 hours. Identical workup yielded 3.88 g, m.p. 140°–2° of pure 4-azafluoren-9-one.

Part C: Reduction of 4-azafluoren-9-one to 4-azafluorene

Following the procedure described in Example 608, Part C, 3.45 g (19 mmole), of 4-azafluoren-9-one, 6.8 g (0.213 mole) of hydrazine in 50 ml of diethyleneglycol were combined and heated to 205° over a 30 -minute period. TLC showed no remaining starting material. Identical workup yielded 2.33 g of pure 4-azafluorene, Rf-0.46 (hexane ethylacetatetriethylamine, 29.75:69.46:0.79).

Part D: Preparation of 5,5-Bis(4-pyridinylmethyl)-indeno-[1,2-b]pyridine

Following the procedure described in Example 608, Part D, alkylation of 2.1 g (12.6 mole) of 4-azafluorene, in the presence of 1.51 g (31.45 mmole) of 50% sodium hydride with 5.0 g (30.4 mmole) of 4-picolyl-chloride yielded 2.8 g. Flash chromatography with ethyl acetate yielded 2.0 g of material containing a small amount of color. Recrystallization from butyl chloride yielded 1.5 g of pure compound, m.p. 163°–4°.

HRMS 349.1579 (calculated for $C_{24}H_{19}N_3$)
HRMS 349.1570 (observed)

NMR(200 MHz, CDCl₃) δ 3.407(s,4H-CH₂-pyridyl); 6.498–6.529(dd,4H,β-pyridyls); 7.149–7.770(m,6-H,aromatic); 8.137–8.167(d,4H,β-pyridyls); 8.437–8.469(dd,1H,α-CHN-azafluorene).

EXAMPLE 624

9,9-Bis(4-pyridinylmethyl)cyclopenta-[1,2-b:3,4-b']dipyridine

Part A: Preparation of 1,5-diazafluoren-9-one 11.8 g (0.178 mole) of potassium hydroxide was dissolved in 2000 ml of water in a 5-liter multineck round bottom flask. To this solution, 18.0 g (0.1 mole) of commercial 1,7-diazaphenanthroline was added. The mixture was heated to boiling, at which time the 1,7-diazaphenanthroline dissolved. To the boiling solution, a solution of 50.6 g (0.32 mole) of potassium permanganate in 800 ml of water was added dropwise with vigorous mechanical stirring at such a rate that the drops of permanganate were rapidly reduced. For this compound, the addition took one hour. The reaction mixture was refluxed 30 minutes longer, then the hot mixture was filtered. The filtrate was cooled to room temperature and extracted with chloroform. It was dried with sodium sulfate and the chloroform rotary evaporated. The crude product was recrystallized from water, then dried in a vacuum dessicator over potassium hydroxide. The yield of pure 1,5-diazafluoren-9-one was 3.3 g, m.p. 158°–9°. The above reaction was repeated and a further 3.3 g of material was obtained, which was combined with the first lot.

Part B: Reduction of 1,5-diazafluoren-9-one to 1,5-diazafluorene

Following the procedure described in Example 608, Part C, 6.0 g (33 mmole) of 1,5-diazafluoren-9-one and 11.8 g (0.37 mole) of hydrazine were combined with 100 ml of diethyleneglycol and heated rapidly to 200°. The reaction was kept at this temperature for 30 minutes, then for 3 hours at 180°. Following the described workup, the crude yield was 4.69 g, m.p. 85°. Recrystallization from cyclohexane yields 4.0 g, m.p. 99°–100° of pure 1,5-diazafluorene.

Part 3: Preparation of 9,9-Bis(4-pyridinylmethyl)cyclopenta[1,2-b:3,4-b']dipyridine Following the alkylation procedure described in Example 608, Part D, 2.0 g (12 mmole) of 1,5-diazafluorene, 4.68 g (29 mmole) of 4-picolylchloride, 1.44 g (30 mmole) of 50% sodium hydride were heated at 55° in 10 ml tetrahydrofuran and 25 ml benzene until TLC (ethyl acetate-methanol-90:10) showed appearance of product (Rf 0.065) and disappearance of starting diazafluorene (Rf 0.28). Crude product triturated with ether to yield 2.90 g, m.p. 133°–137°. This was flash chromatographed with ethyl acetate and recrystallized from benzene using charcoal to decolorize. Yield 2.4 g, m.p. 139.8°–140.9°. Rf 0.16 (ethyl acetate-methanol 90:10). NMR (200 MHz,CDCl₃) δ 3.397–3.718(dd,4H,(—CH₂—pyridyl); 6.450–6.475(d,4H,β-pyridyls); 7.240–7.324(m,2H,the 3- and 7- H's of the 1,5-diazafluorene, each meta to one of the nitrogens); 7.802–7.808(d,1H,8-H of diazafluorene); 7.879–7.885(d,1H,4-H of diazafluorene); 8.097–8.122 (d,4H,α-pyridyls); 8.451–8.476(d,1H,2-H of diazafluorene); 8.741–8.763(d,1H,6-H of diazafluorene).

| HRMS: | Calculated Mass: | Measured Mass |
|---|---|---|
| | 350.1531 | 350.1529 |

Difference=0.0003 for $C_{23}H_{18}N_4$.

The compounds of Examples 440–464, 532, 560, 608, 611, 624 and other compounds which can be prepared by the methods described above, are illustrated in Table IX. The compounds of Examples 440–531 in Table IX have J, K, L and M as CH except where an $R_1$, $R_2$ or $R_5$ substituent group was shown, in which case the substituent group replaces the H at that position.

TABLE IX

| Ex. | R₁ | R₂ | R₅ | B | D | A | Het¹ | Het² | mp °C. (salt mp) |
|---|---|---|---|---|---|---|---|---|---|
| 440 | H | H | H | H | H | $-\overset{O}{\underset{\|}{C}}-$ | 4-pyridyl | 4-pyridyl | 207–208 |
| 441 | H | H | H | H | H | $-\overset{O}{\underset{\|}{C}}-$ | 4-pyridyl | 4-pyridyl | (275–277) |
| 442 | H | H | H | H | H | —O— | 4-pyridyl | 4-pyridyl | 212–213 |
| 443 | H | H | H | H | H | bond | 4-pyridyl | 4-pyridyl | (>300)[a] |
| 444 | 2-NO₂ | H | H | H | H | bond | 4-pyridyl | 4-pyridyl | 260–264[b] (>300) |
| 445 | H | H | H | H | H | —S— | 4-pyridyl | 4-pyridyl | 201.4–203.4 |
| 446 | 1-CH₃ | H | H | H | H | bond | 4-pyridyl | 4-pyridyl | (>300)[c,d] |
| 447 | 2-Br | H | H | H | H | bond | 4-pyridyl | 4-pyridyl | (>300)[e,f] |
| 448 | 2-NH₂ | H | H | H | H | bond | 4-pyridyl | 4-pyridyl | (>300)[g] |
| 449 | 2-NHCCH₃ (O=) | H | H | H | H | bond | 4-pyridyl | 4-pyridyl | (>300)[h] |
| 450 | 2-CCH₃ (O=) | H | H | H | H | bond | 4-pyridyl | 4-pyridyl | (>300)[i,j] |

TABLE IX-continued
| | $R_1$ | $R_2$ | 3 | 4 | 5 | A | $Het^1$ | $Het^2$ | |
|---|---|---|---|---|---|---|---|---|---|
| 451 | 2-F | H | H | H | H | bond | 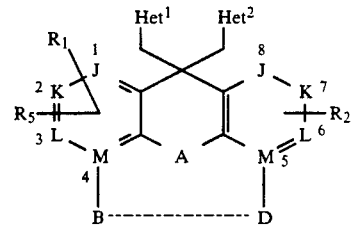 | 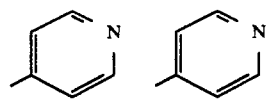 | (>300)[k,l] |
| 452 | 2-CHF$_2$ | H | H | H | H | bond | 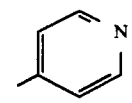 | 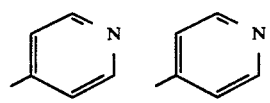 | (>300)[m,n] |
| 453 | 2-CH(OH)CH$_3$ | H | H | H | H | bond | 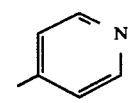 | 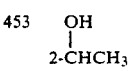 | [o,p] |
| 454 | 2-CH$_3$ | H | H | H | H | bond | 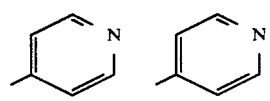 | 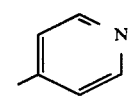 | [q,r] |
| 455 | 2-Et | H | H | H | H | bond | 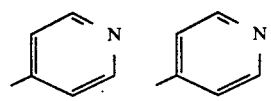 | 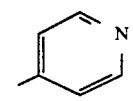 | [s,t] |
| 456 | 2-OCH$_3$ | H | H | H | H | bond | 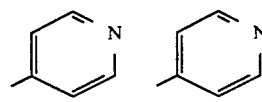 | 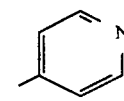 | [u] |
| 457 | H | H | H | H | H | bond | 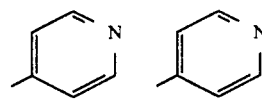 | 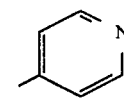 | 137–138[v,w] |
| 458 | 1-CH$_3$ | H | 4-CH$_3$ | H | H | −C(O)− | 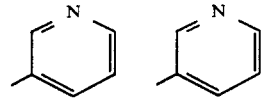 | 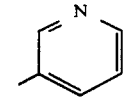 | 211–213[x] |
| 459 | 4-Cl | 5-Cl | H | H | H | −C(O)− |  | 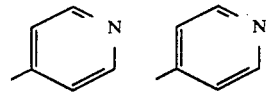 | 170–172[y,z] |
| 460 | 1-Cl | 8-Cl | H | H | H | −C(O)− | 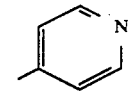 |  | [aa,bb] |
| 461 | H | H | H | H | H | −C(O)− | 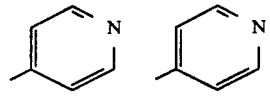 | 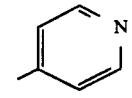 | [cc,dd] |
| 462 | H | H | H | H | H | 2-CH(OH)CH$_3$ |  | 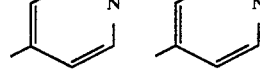 | 196–197[ee] |

TABLE IX-continued

| # | R₁ | R₅ | R₂ | | | A | Het¹ | Het² | mp |
|---|---|---|---|---|---|---|---|---|---|
| 463 | H | H | H | H | H | -C(=NOH)- | 4-pyridyl | 4-pyridyl | 226-227 ff |
| 464 | H | H | H | | | -C(CH₃)=CH- (bond) | 4-pyridyl | 4-pyridyl | 201-202 gg |
| 465 | H | H | H | H | H | -C(=O)- | 4-pyrimidinyl | 4-pyrimidinyl | |
| 466 | H | H | H | H | H | -C(=O)- | 4-pyridyl | 3-tetrahydrofuryl | |
| 467 | H | H | H | H | H | -C(=O)- | 4-pyridyl | 3-tetrahydrofuryl | |
| 468 | H | H | H | H | H | -C(=O)- | 4-pyridyl | 3-pyridyl | |
| 469 | H | H | H | H | H | -C(=O)- | 4-pyridyl | 3-(1H-pyrazolyl) | |
| 470 | H | H | H | H | H | -C(=O)- | 4-pyridyl | 2-pyrazinyl | |
| 471 | 1-CH₃ | H | H | H | H | -C(=O)- | 4-pyridyl | 4-pyridyl | |
| 472 | H | 2-Cl | H | H | H | -C(=O)- | 4-pyridyl | 4-pyridyl | |
| 473 | 2-CH₃ | 7-CH₃ | H | H | H | -C(=O)- | 4-pyridyl | 4-pyridyl | |

TABLE IX-continued
| | | | | | | | Het¹ | Het² |
|---|---|---|---|---|---|---|---|---|
| 474 | 3-Et | 6-Et | H | H | H | −C(=O)− | 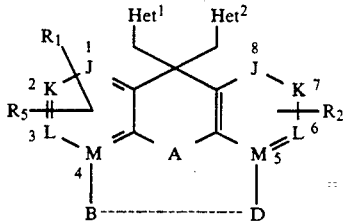 |  |
| 475 | 4-OCH₃ | 5-OCH₃ | H | H | H | −C(=O)− | 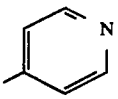 | 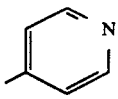 |
| 476 | 4-CF₃ | H | H | H | H | −C(=O)− |  | 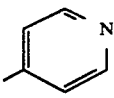 |
| 477 | 2-CN | H | H | H | H | −CH(OAc)− | 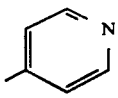 |  |
| 478 | H | 4-NO₂ | H | H | H | −CH(OAc)− | 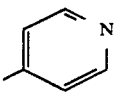 | 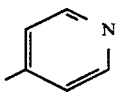 |
| 479 | 2-NH₂ | H | H | H | H | −CH(OAc)− |  | 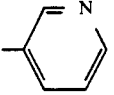 |
| 480 | 1-C(=O)CH₃ | H | H | H | H | −CH(OAc)− | 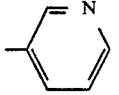 |  |
| 481 | 3-NHC(=O)CH₃ | H | H | H | H | −CH(OAc)− | 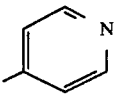 | 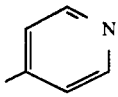 |
| 482 | H | H | H | H | H | −CH(OAc)− |  | 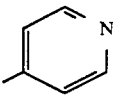 |
| 483 | H | H | H | H | H | −CH(OAc)− | 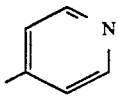 |  |
| 484 | 1-CH₃ | H | H | H | H | −CH(OAc)− |  | 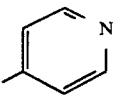 |
| 485 | 2-Cl | H | H | H | H | −CH(OAc)− | 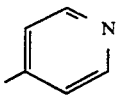 |  |

TABLE IX-continued

| | R | | R1 | | | Het1/Het2 |
|---|---|---|---|---|---|---|
| 486 | 2-CH$_3$ | 7-CH$_3$ | H | H | H | OAc / —CH— | 4-pyridyl / 4-pyridyl |
| 487 | 3-NMe$_2$ | H | H | H | H | OAc / —CH— | 4-pyridyl / 3-tetrahydrofuryl |
| 488 | 4-N(CH$_3$)COCH$_3$ | H | H | H | H | OAc / —CH— | 4-pyridyl / 4-pyridyl |
| 489 | 4-Br | 5-Br | H | H | H | OAc / —CH— | 4-pyridyl / 4-pyrimidinyl |
| 490 | 4-OCH$_3$ | H | H | H | H | OAc / —CH— | 4-pyridyl / 4-pyridyl |
| 491 | 1-CF$_3$ | H | H | H | H | OAc / —CH— | 4-pyridyl / 4-pyridyl |
| 492 | 1-CH$_3$ | H | H | H | H | OAc / —CH— | 4-pyridyl / 4-pyridyl |
| 493 | 2-Pr | H | H | H | H | OAc / —CH— | 4-pyridyl / 4-pyridyl |
| 494 | 3-NHCOCH$_3$ | H | H | H | H | —O— | 4-pyridyl / 4-pyridyl |
| 495 | 1-COCH$_3$ | H | H | H | H | —O— | 4-pyridyl / 3-tetrahydrofuryl |
| 496 | 2-CH$_3$ | H | H | H | H | —O— | 4-pyridyl / pyridazinyl |

TABLE IX-continued

| # | R₁ | R₅ | R | R | A | Het¹ | Het² |
|---|---|---|---|---|---|---|---|
| 497 | 3-Br | 7-Br | H | H · H | —O— | 4-pyridyl | 4-pyridyl |
| 498 | 4-OCH₃ | H | H | H H | —S(=O)— | 4-pyridyl | 4-pyridyl |
| 499 | 2-CN | H | H | H H | —S(=O)— | 4-pyridyl | 4-pyridyl |
| 500 | 2-NO₂ | H | H | H H | —S(=O)— | 4-pyridyl | 4-pyridyl |
| 501 | 3-C(=O)CH₃ | H | H | H H | —S(=O)— | 4-pyridyl | 4-pyridyl |
| 502 | 1-CF₃ | H | H | H H | —S(=O)— | 4-pyridyl | 3-tetrahydrofuranyl |
| 503 | 3-Pr | 6-Pr | H | H H | —S(=O)— | 4-pyridyl | 4-pyridyl |
| 504 | 2-N(Et)C(=O)CH₃ | H | H | H H | —S(=O)— | 4-pyridyl | 4-pyridyl |
| 505 | 3-CH₃ | H | H | H H | —CH₂— | 4-pyridyl | 4-pyridyl |
| 506 | 2-Cl | H | H | H H | —CH₂— | 4-pyridyl | 4-pyridyl |
| 507 | 2-CH₃ | 7-CH₃ | H | H H | —CH₂— | 4-pyridyl | 4-pyridyl |
| 508 | 3-Br | 6-Br | H | H H | —CH₂— | 4-pyridyl | 4-pyridyl |

TABLE IX-continued

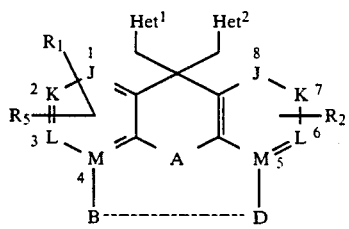

| | | | | | | Het¹ | Het² |
|---|---|---|---|---|---|---|---|
| 509 | 4-OCH₃ | H | H | H | H | —CH₂— | 4-pyridyl | 4-pyridyl |
| 510 | 2-CF₃ | H | H | H | H | —CH₂— | 4-pyridyl | 4-pyridyl |
| 511 | 3-NHC(O)CH₃ | H | H | H | H | —CH₂— | 4-pyridyl | 4-pyridyl |
| 512 | 4-C(O)CH₃ | H | H | H | H | —CH₂— | 4-pyridyl | 4-pyridyl |
| 513 | 2-CN | H | H | H | H | —SO₂— | 4-pyridyl | 4-pyridyl |
| 514 | 1-CH₃ | 8-CH₃ | H | H | | —SO₂— | 4-pyridyl | 4-pyridyl |
| 515 | 2-NHC(O)CH₃ | H | H | H | H | —SO₂— | 4-pyridyl | 4-pyridyl |
| 516 | 4-C(O)CH₃ | H | H | H | H | —SO₂— | 4-pyridyl | 4-pyridyl |
| 517 | 3-Br | H | H | H | H | —SO₂— | 4-pyridyl | 4-pyridyl |
| 518 | 4-Pr | H | H | H | H | —SO₂— | 4-pyridyl | 4-pyridyl |
| 519 | 3-CF₂CF₃ | H | H | H | H | 1,3-dioxolane | 4-pyridyl | 4-pyridyl |

5,300,642

TABLE IX-continued

| # | R | R5 | | | | A group | Het1 | Het2 |
|---|---|---|---|---|---|---|---|---|
| 520 | 2-NH$_2$ | H | H | H | H | 1,3-dioxolane | 4-pyridyl | 4-pyridyl |
| 521 | 1-NO$_2$ | H | H | H | H | 1,3-dioxolane | 4-pyridyl | 4-pyridyl |
| 522 | 4-CN | H | H | H | H | 1,3-dithiolane | 4-pyridyl | 4-pyridyl |
| 523 | 2-CH$_3$ | 7-CH$_3$ | H | H | H | 1,3-dithiolane | 4-pyridyl | 4-pyridyl |
| 524 | 3-NHC(O)CH$_3$ | H | H | H | H | —C(=NOH)— | 4-pyridyl | 4-pyridyl |
| 525 | 2-CH$_3$ | H | H | H | H | —C(=NOH)— | 4-pyridyl | 4-pyridyl |
| 526 | 3-NMe$_2$ | H | H | H | H | —C(=NOH)— | 4-pyridyl | 4-pyridyl |
| 527 | 4-propyl | H | H | H | H | —C(=NOH)— | 4-pyridyl | 4-pyridyl |
| 528 | 2-C(O)CH$_3$ | H | H | H | H | —C(=NOH)— | 4-pyridyl | 4-pyridyl |
| 529 | 3-NO$_2$ | 6-NO$_2$ | H | H | H | —C(=NOH)— | 4-pyridyl | 4-pyridyl |
| 530 | 2-Et | H | H | CH=CH | bond | | 4-pyridyl | 4-pyridyl |
| 531 | 3-NHC(O)CH$_3$ | H | H | H | bond | | 4-pyridyl | 4-pyridyl |

TABLE IX-continued

| Ex. | R₁ | R₂ | R₅ | J K L M | B | D | A | Het¹ | Het² | mp °C. |
|---|---|---|---|---|---|---|---|---|---|---|
| 532 | H | H | H | C C C N | — | — | bond | 4-pyridyl | 4-pyridyl | hh |
| 533 | H | H | H | C C C C | —CH₂—CH₂— | | bond | 3-pyridyl | 3-pyridyl | |
| 534 | H | H | H | C C C C | H | H | —C(=S)— | 4-pyridyl | 4-pyridyl | |
| 535 | H | H | H | C C C C | H | H | —S— | 4-pyridyl | 4-pyridyl | |
| 536 | 2-CH₃ | H | H | C C C C | H | H | —CH(OH)— | 4-pyridyl | 4-pyridyl | |
| 537 | H | H | H | C C C C | H | H | —CH(OH)— | 4-pyridyl | 4-pyridyl | |
| 538 | 2-NHCOCH₃ | H | H | C C C C | H | H | —C(=S)— | 4-pyridyl | 4-pyridyl | |
| 539 | 3-CH₃ | H | H | C C C C | H | H | —C(=S)— | 4-pyridyl | 4-pyridyl | |
| 540 | H | H | H | C C C C | H | H | —CH(OCH₃)— | 4-pyridyl | 4-pyridyl | |
| 541 | H | H | H | C C C C | H | H | —N(COCH₃)— | 4-pyridyl | 4-pyridyl | |
| 542 | H | H | H | C C C C | H | H | —CH(OCH₃)— | 2-pyrimidinyl | 2-pyrimidinyl | |

TABLE IX-continued
| | | | | | | | | | | | |
|---|---|---|---|---|---|---|---|---|---|---|---|
| 543 | H | H | H | C C | C | C | H | H | −N−CH | 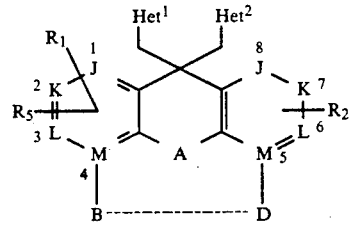 | |
| 544 | H | H | H | C C | C | C | H | H | S‖C | 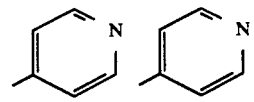 | |
| 545 | H | H | H | C C | C | C | H | H | −S− | 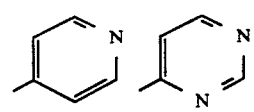 | |
| 546 | 2-NO₂ | H | H | C C | C | C | H | H | −S− | 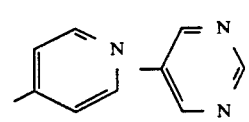 | |
| 547 | 2-CCH₃ (O) | H | H | C C | C | C | H | H | −S− | 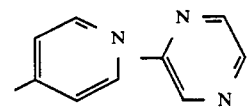 | |
| 548 | 1-CH₃ | H | 4-CH₃ | C C | C | C | H | H | −S− |  | |
| 549 | 4-Br | H | H | C C | C | C | H | H | OH −CH− | 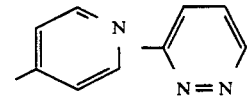 | |
| 550 | 4-Br | 5-Br | H | C C | C | C | H | H | OH −CH− | 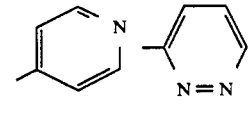 | |
| 551 | 2-Cl | H | H | C C | C | C | H | H | OH −CH− | 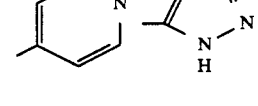 | |
| 552 | H | H | H | C C | C | C | H | H | OH −CH− | 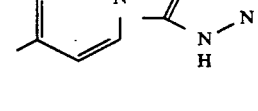 | |
| 553 | H | H | H | C C | C | C | H | H | OH −CH− | 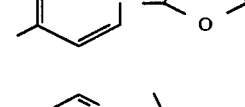 | |

TABLE IX-continued

| | | R₁ | | | | | | | | | Het¹ Het² | | | |
|---|---|---|---|---|---|---|---|---|---|---|---|---|---|---|

| # | R₁ | | | J K L M | | | | R₅ | R₂ | A | Het¹ | Het² | |
|---|---|---|---|---|---|---|---|---|---|---|---|---|---|
| 554 | 2-CF₃ | H | H | C C | C | C | H | H | −CH−OH | | | | |
| 555 | 2-CN | H | H | C C | C | C | H | H | −CH−OH | | | | |
| 556 | 3-NMe₂ | H | H | C C | C | C | H | H | −CH−OH | | | | |
| 557 | H | H | H | C C | C | C | H | H | bond | | | | |
| 558 | 2-CH₃ | H | H | C C | C | C | H | H | bond | | | | |
| 559 | 1-CH₂CH₃ | H | H | C C | C | C | H | H | bond | | | | |
| 560 | H | H | H | C C | C | C | H | H | bond | | | 244-7 | |
| 561 | H | H | H | C C | C | C | H | H | bond | | | | |
| 562 | H | H | H | C C | C | C | H | H | bond | | | | |
| 563 | 2-CCH₃ (O) | H | H | C C | C | N | H | H | bond | | | | |
| 564 | 1-CH₃ | H | H | C C | N | C | H | H | bond | | | | |
| 565 | 4-NHCOCH₃ | H | H | C N | C | C | H | H | bond | | | | |

TABLE IX-continued

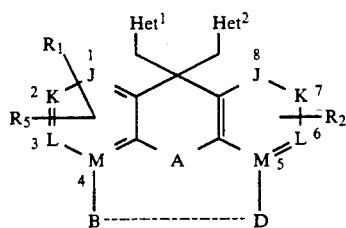

| # | R1 | | | J K L M | | | | R5 | A | Het1 | Het2 |
|---|---|---|---|---|---|---|---|---|---|---|---|
| 566 | 2-NHCOCH₃ | H | H | N C C C | H | H | | | bond | (2-pyridyl) | (3-pyridyl) |
| 567 | 2-CH₃ | H | H | C C C C | H | H | | | O-CH₂-O (1,3-dioxolane) | (4-pyridyl) | (4-pyridyl) |
| 568 | 2-Et | H | H | C C C C | H | H | | | O-CH₂-O (1,3-dioxolane) | (4-pyridyl) | (4-pyridyl) |
| 569 | 2-NCCH₃ (O), CH₃ | H | H | C C C C | H | H | | | S-CH₂-S (1,3-dithiane) | (4-pyridyl) | (4-pyridyl) |
| 570 | 3-OCH₃ | 6-OCH₃ | H | C C C C | H | H | | | S-CH₂-S (1,3-dithiane) | (4-pyridyl) | (4-pyridyl) |
| 571 | H | H | H | C C C C | H | H | | | —CH=CH— | (4-pyridyl) | (4-pyridyl) |
| 572 | 1-CH₃ | H | H | C C C C | H | H | | | —CH=CH— | (4-pyrimidinyl) | (4-pyrimidinyl) |
| 573 | 2-Et | H | H | C C C C | H | H | | | —CH=CH— | (4-pyridyl) | (4-pyrimidinyl) |
| 574 | 2-CH(O) | H | H | C C C C | H | H | | | —CH=CH— | (4-pyridyl) | (3-tetrahydrofuryl) |
| 575 | 3-CH(O) | H | H | C C C C | H | H | | | —(CH₂)₂— | (4-pyridyl) | (4-pyridyl) |
| 576 | 4-NMe₂ | H | H | C C C C | H | H | | | —(CH₂)₂— | (4-pyrimidinyl) | (4-pyrimidinyl) |

TABLE IX-continued

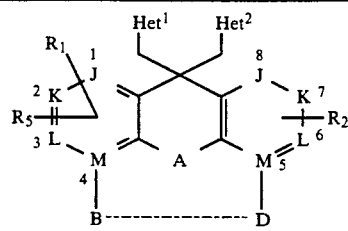

| # | R1 | | | J K L M | | | | R5 | R2 | B---D | Het1 | Het2 |
|---|---|---|---|---|---|---|---|---|---|---|---|---|
| 577 | H | H | H | C C | C | C | H | H | —(CH$_2$)$_2$— | | pyridyl | pyrimidinyl |
| 578 | H | H | H | C C | C | C | H | H | —(CH$_2$)$_2$— | | pyridyl | 3-methyltetrahydrofuranyl |
| 579 | H | H | H | C C | C | C | H | H | —CH(OH)— | | pyridyl | pyridyl |
| 580 | H | H | H | C C | C | C | H | H | —CH(OCOCH$_2$CH$_3$)— | | pyridyl | pyridyl |
| 581 | H | H | H | C C | C | C | H | H | —N(CHO)— | | pyridyl | pyridyl |
| 582 | H | H | H | C C | C | C | H | H | —N(COCH$_2$CH$_3$)— | | pyridyl | pyridyl |
| 583 | H | H | H | C C | C | C | H | H | —CH(OCH$_2$CH$_3$)— | | pyridyl | pyridyl |
| 584 | H | H | H | C C | C | C | H | H | —CH(OCH$_2$CH$_2$CH$_3$)— | | pyridyl | pyridyl |
| 585 | 2-CH$_3$ | H | 3-CH$_3$ | C C | C | C | H | H | —N(H)— | | pyridyl | pyridyl |
| 586 | 2-CH$_3$ | 6-CH$_3$ | 3-CH$_3$ | C C | C | C | H | ·H | —N(CH$_3$)— | | pyridyl | pyridyl |
| 587 | 2-OCH$_3$ | 7-OCH$_3$ | H | C C | C | C | H | H | —N(CH$_2$CH$_3$)— | | pyridyl | pyridyl |
| 588 | 2-OCH$_3$ | H | 3-OCH$_3$ | C C | C | C | H | H | —N(CH$_2$CH$_2$CH$_3$)— | | pyridyl | pyridyl |

TABLE IX-continued

| | | | | | | | | | | Het¹ | Het² |
|---|---|---|---|---|---|---|---|---|---|---|---|
| 589 | 3-Et | 6-Et | H | C | C | C | C | H | H | CHO<br>—N— | 4-pyridyl | 4-pyridyl |
| 590 | 3-Br | 6-Br | H | C | C | C | C | H | H | (CO)CH₃<br>—N— | 4-pyridyl | 4-pyridyl |
| 591 | 3-OEt | 6-OEt | H | C | C | C | C | H | H | (CO)CH₂CH₃<br>—N— | 4-pyridyl | 4-pyridyl |
| 592 | H | H | H | C | C | C | C | H | H | —(CH₂)₃— | 2-pyrimidinyl | 4-pyrimidinyl |
| 593 | H | H | H | C | C | C | C | H | H | —(CH₂)₃— | 4-pyrimidinyl | 5-pyrimidinyl |
| 594 | H | H | H | C | C | C | C | H | H | —(CH₂)₃— | 5-pyrimidinyl | 4-pyridyl |
| 595 | H | H | H | C | C | C | C | H | H | —(CH₂)₃— | 2-pyrimidinyl | 3-pyridyl |
| 596 | H | H | H | C | C | C | C | H | H | —(CH₂)₃— | 4-pyrimidinyl | 2-pyridyl |
| 597 | H | H | H | C | C | C | C | H | H | —(CH₂)₃— | 5-pyrimidinyl | 3-tetrahydrofuryl |
| 598 | H | H | H | C | C | C | C | H | H | —(CH₂)₃— | 2-pyrimidinyl | 2-tetrahydrofuryl |
| 599 | 2-OH | H | H | C | C | C | C | H | H | bond | 4-pyridyl | 4-pyridyl |

TABLE IX-continued

Structure with substituents R₁, R₂, R₅, J₁, K₂, L₃, M₄, J₈, K₇, L₆, M₅, B, D, A, Het¹, Het²

| Ex. | R₁ | R₂ | R₅ | J₁ | K₂ | L₃ | M₄ | J₈ | K₇ | L₆ | M₅ | B | D | A | Het¹ | Het² |
|-----|----|----|----|----|----|----|----|----|----|----|----|----|---|---|------|------|
| 600 | 2-OC(=O)CH₃ | H | H | C | C | C | C | H | | | | H | | bond | 4-pyridyl | 4-pyridyl |
| 601 | 3-OC(=O)CH₂CH₃ | H | H | C | C | C | C | H | | | | H | | bond | 4-pyridyl | 4-pyridyl |
| 602 | 4-OCH₂CH₂CH₃ | H | H | C | C | C | C | H | | | | H | | bond | 4-pyridyl | 4-pyridyl |
| 603 | 2-CH₂CF₃ | H | H | C | C | C | C | H | | | | H | | bond | 4-pyridyl | 4-pyridyl |
| 604 | 3-CF₂CF₃ | H | H | C | C | C | C | H | | | | H | | bond | 4-pyridyl | 4-pyridyl |
| 605 | 4-CF₂CF₂CF₃ | H | H | C | C | C | C | H | | | | H | | bond | 4-pyridyl | 4-pyridyl |
| 606 | 1-CF₃ | 8-CF₃ | H | C | C | C | C | H | | | | H | | bond | 4-pyridyl | 4-pyridyl |
| 607 | 2-CH₃ | 7-CH₃ | H | C | C | C | C | | | | | CH=CH | | bond | 4-pyridyl | 3-pyridyl |

| Ex. | R₁ | R₂ | R₅ | J₁ | K₂ | L₃ | M₄ | J₈ | K₇ | L₆ | M₅ | B | D | A | Het¹ | Het² | mp °C. |
|-----|----|----|----|----|----|----|----|----|----|----|----|---|---|---|------|------|--------|
| 608 | H | H | H | N | C | C | C | C | C | C | C | H | H | bond | 4-pyridyl | 4-pyridyl | 204.7–206 |
| 609 | H | H | H | C | N | C | C | C | C | C | C | H | H | bond | 4-pyridyl | 3-pyridyl | |
| 610 | H | H | H | C | C | N | C | C | C | C | C | H | H | bond | 4-pyridyl | 4-pyridyl | |

TABLE IX-continued

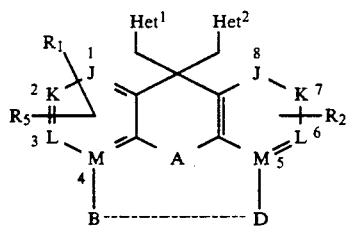

| | R₁ | | J¹ | K² | L³ | M⁴ | A | M⁵ | L⁶ | K⁷ | J⁸ | R₂ | R₅ | B---D | Het¹ | Het² | |
|---|---|---|---|---|---|---|---|---|---|---|---|---|---|---|---|---|---|
| 611 | H | H | H | C | C | C | N | C | C | C | C | — | H | bond | pyridyl | pyridyl | 163-164 |
| 612 | 2-CH₃ | H | H | C | C | C | C | N | C | C | C | H | H | bond | pyridyl | pyridyl | |
| 613 | 4-NH₂ | H | H | C | C | C | C | C | N | C | C | H | H | bond | pyridyl | pyridyl | |
| 614 | 2-NH₂ | H | H | C | C | C | C | C | C | N | C | H | H | bond | pyridyl | pyrazinyl | |
| 615 | 4-CH₃ | H | H | C | C | C | C | C | C | C | N | — | H | bond | pyridyl | pyridazinyl | |
| 616 | H | 2,3-benzo | N | C | C | C | C | C | C | C | C | H | H | bond | pyridyl | pyridazinyl | |
| 617 | H | 3,4-benzo | C | N | C | C | C | C | C | C | C | H | H | bond | pyridyl | pyrazolyl | |
| 618 | H | 2,3-benzo | C | C | C | C | C | C | N | C | C | H | H | bond | pyridyl | pyrazolyl | |
| 619 | H | 3,4-benzo | N | C | C | C | C | C | C | C | N | — | H | bond | pyridyl | thienyl | |
| 620 | H | 2,3-benzo | C | C | C | C | C | C | C | C | C | H | H | bond | pyridyl | pyridyl | |
| 621 | H | 3,4-benzo | C | C | C | C | C | C | C | C | C | H | H | bond | pyridyl | pyridyl | |

TABLE IX-continued

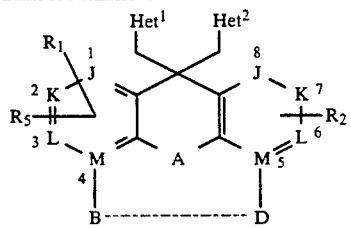

| # | R1 | R5 | | J | K | L | M | A | M | L | K | J | | R2 | B-D | Het1 | Het2 | mp |
|---|----|----|-|---|---|---|---|---|---|---|---|---|-|----|-----|------|------|-----|
| 622 | H | H | H | N | C | C | C | C | N | C | C | H | H | | bond | 4-pyridyl | 4-pyridyl | |
| 623 | H | H | H | N | C | C | C | C | N | C | C | H | H | | bond | 4-pyridyl | 4-pyridyl | |
| 624 | H | H | H | N | C | C | C | C | C | N | C | H | — | | bond | 4-pyridyl | 4-pyridyl | 139.8–140.9 |
| 625 | H | H | H | C | C | N | C | N | C | C | C | H | H | | bond | 4-pyridyl | 4-pyridyl | |
| 626 | H | H | H | C | C | N | C | C | N | C | C | H | H | | bond | 4-pyridyl | 4-pyridyl | |
| 627 | H | H | H | C | C | N | C | C | C | C | N | H | — | | bond | 4-pyridyl | 4-pyridyl | |
| 628 | H | H | H | C | N | C | C | N | C | C | C | H | H | | bond | 4-pyridyl | 4-pyridyl | |
| 629 | H | H | H | C | N | C | C | C | C | N | C | H | H | | bond | 4-pyridyl | 4-pyridyl | |
| 630 | H | H | H | C | N | C | C | C | C | C | N | H | — | | bond | 4-pyridyl | 4-pyridyl | |
| 631 | H | H | H | C | C | C | N | N | C | C | C | — | H | | bond | 4-pyridyl | 4-pyridyl | |
| 632 | H | H | H | C | C | C | N | C | N | C | C | — | H | | bond | 4-pyridyl | 4-pyridyl | |
| 633 | H | H | H | C | C | C | N | C | C | N | C | — | H | | bond | 4-pyridyl | 4-pyridyl | |

TABLE IX-continued

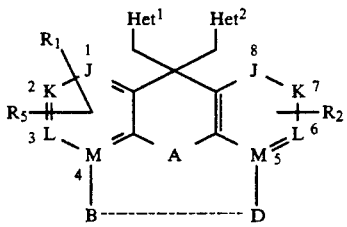

FOOTNOTES TO TABLE IX
aHRMS, M+ = 348.1615
bHRMS, M+ = 393.1465
cHRMS, M+ = 362.1779
dNMR(200 MHz, CDCl$_3$)2.82(s, 3H), 3.60(dd, 4H), 6.39(m, 4H), 7.0-7.5(m, 4H), 7.0-7.5(m, 7H-arom), 8.0(m, 4H)
eHRMS, M+ = 426.0758
fNMR(200 MHz, CDCl$_3$)3.39(dd, 4H( ), 6.48(d, 4H), 7.10-7.67(m, 7H-arom), 8.12(d, J=5.7Hz, 4H)
gHRMS, M+ = 363.1728
hNMR(CDCl$_3$)2.19(s, 3H), 3.40(s, 4H), 6.50(d, J=5.7Hz, 4H), 6.92(m, 1H), 7.14-7.33(m, 4H), 7.52(d, 1H), 8.04(d, J=5.8Hz, 4H), 8.25(s, 1H), 8.5(s, 1H, exchangeable with D$_2$O).
iHRMS, M+ = 390.1720
jNMR 2.68(s, 3H), 3.46(s, 4H), 6.44(d, J=5.9Hz, 4H), 7.29-7.87(m, 6H), 8.05(d, J=5.9Hz, 4H), 8.22(d, 1H)
kHRMS, M+ = 366.1566
lNMR 3.38(dd, 4H), 6.49(d, J = 6.0Hz, 4H), 6.9(m, 1H), 7.14-7.36(m, arom), 7.5(d, 1H), 8.1(d, J=6.0Hz, 4H)
mHRMS, M+ = 398.1583
nNMR 3.43(s, 4H), 6.45(d, J=5.7Hz, 4H), 6.74(t, J=5.6Hz, 1H), 7.26-7.70(m, arom), d, J=5.7Hz, 4H)
oHRMS, M+
pNMR 1.50(d, J=6.5Hz, 3H), 3.39(s, 4H), 4.92(q, J=6.4Hz, 1H), 6.43(dd, 4H), 7.08-7.58(n-arom), 7.87(d, 2H), 7.97(d, 2H)
qHRMS, M+ = 362.1779
rNMR 2.47(s, 3H), 3.37(s, 4H), 6.49(d, J=5.3Hz, 4H), 7.03-7.45(m, arom), 8.09(d, 4H)
sHRMS, M+ = 376.1927
tNMR 1.30(t, J=7.8Hz, 3H), 2.74(q, J=7.6Hz, 2H), 3.37(s, 4H), 6.49(d, J=5.9Hz, 4H), 7.04-7.48(m, 7H-arom), 8.09(d, J=5.4Hz, 4H)
uNMR 3.37(s, 4H), 3.89(s, 3H), 6.52(broad, 4H) 6.80(m, 1H), 7.01(m, 1H), 7.01(d, J=2.1Hz, 1H), 7.26(m, 5H), 7.45(d, J=7.5Hz, 1H), 8.11(broad, 4H)
vHRMS, M+ = 348.1626
wNMR 3.41(s, 4H), 6.71-6.97(m, 4H), 7.17-7.35(tt, 6H), 7.50-7.54(d, J=6.9Hz, 2H), 7.91(s, 2H), 8.12-8.15(d, J=5.4Hz, 2H)
x
yHRMS, M+ = 440.0799
zNMR 3.53(s, 4H), 6.43(d, J=6.1Hz, 4H), 7.33-7.51(m, 6-arom), 8.3(d, J= 6.2Hz, 4H)
aaHRMS, M+ was 440.0806
bbNMR 4.66(s, 4H), 6.33(d, J=6.1Hz, 4H), 7.45(t, J=6.6Hz, 2H-arom), 779(d, J=7.1Hz, 2H-arom), 8.01(d, J=6.3, 4H), 8.13(d, J=7.1Hz, 2H)
ccHRMS, M+ 376.1573
ddNMR 3.77(s, 4H), 6.49(d, J=6.9Hz, 2H-arom), 6.66(dd, J=7.91, J=4.8, 2H-arom), 7.48(t, J=7.4Hz, 2H-arom), 7.56(m, 1H), 7.79(t, J=7.3Hz, 2H), 8.03(d, J=7.0Hz, 2H), 8.16(m, J=1.8Hz, 4H)
eeHRMS, M+ 378.1691
ffHRMS, M+ 391.1634
ggHRMS, M+ 377.1060
hhHRMS, M+ 350.0971

Biochemical Test Procedure

The effect of compounds on the release of acetylcholine (ACh) from rat cerebral cortex slices was tested essentially using a slice superfusion procedure described by Mulder et al, Brain Res., 70, 372, (1974), as modified according to Nickolson et al, Naunyn Schmied. Arch. Pharmacol., 319, 48 (1982).

Male Wistar rats (Charles River) weighting 175-200 grams were used. They were housed for at least seven days before the experiment in the animal facility under a 12-12 hour light/dark cycle (light on 6.00 h, light off 18.00 h). They had ad lib access to standard rat chow (Purina) and deionized water.

Rats were decapitated and brains were disserted immediately. Slices (0.3 mm thick) from the parietal cortex were prepared manually using a recessed Lucite® guide and subsequently cut into 0.25×0.25 mm squares.

Slices (approximately 100 mg wet weight) were incubated in 10 ml Krebs-Ringer (KR) medium containing (mM): NaCl (116), KCl (3), CaCl$_2$ (1.3), MgCl$_2$ (1.2), KH$_2$PO$_4$ (1.2), Na$_2$SO$_4$ (1.2), NaHCO$_3$ (25), glucose (11), to which 10 μCi $^3$H-Choline (spec. act. approx. 35 Ci/mmol; NEN) and 10 mmoles unlabelled choline had been added to give a final concentration of $10^{-6}$M. Incubation was carried out for 30 minutes at 37° C. under a steady flow of 95% O$_2$/5% CO$_2$. Under these conditions, part of the radioactive choline taken up was converted into radioactive ACh by cholinergic nerve endings, stored in synaptic vesicles and released upon depolarization by high-K+-containing media.

After labelling of the ACh stores, the slices were washed 3 times with non-radioactive KR-medium and transferred to a superfusion apparatus to measure the drug effects on ACh release. The superfusion apparatus consisted of 10 thermostated glass columns of 5 mm diameter which were provided with GF/F glass fiber filters to support the slices (approximately 10 mg tissue/column). Superfusion was carried out with KR-medium (0.3 ml/min) containing $10^{-5}$M hemicholinium-3 (HC-3). HC-3 prevents the uptake of choline, formed during the superfusion from phospholipids and released ACh, which would be converted into unlabelled ACh, and released in preference to the preformed, labelled ACh. The medium was delivered by a 25-channel peristaltic pump(Ismatec; Brinkman) and was warmed to 37° C. in a thermostated stainless steel coil before entering the superfusion column. Each column was provided with a 4-way slider valve (Beckman Instruments) which allowed rapid change of low-to high-K+-KR-medium and with two 10-channel, 3-way valves which were used to change from drug-free to drug-containing low-and high-K+-KR-medium.

After 15 minutes washout of non-specifically bound radioactivity, the collection of 4 minute fractions was started. After 3 four-min. collections, the KR medium was changed for KR medium of which the KCl concentration had been increased to 25 mM (high-K+-KR-medium) (S1). Depolarization-induced stimulation of release by high-K+-KR-medium lasted for 4 minutes. Drug free low-and high-K+-KR-medium were then substituted by drug- or vehicle-containing low- and high-K+-KR-medium and superfusion was continued for 3 four-min. collections with low-K+-KR-medium, 1 four-min. collection with high-K+-KR-medium (S2) and 2 four-min. collections with low-K+-KR-medium.

Drug was added to the media by 100-fold dilution of appropriate concentrations of the drug (in 0.9% NaCl/H$_2$O) with either low- or high-K+-KR-medium.

All superfusion fractions were collected in liquid scintillation counting vials. After superfusion the slices were removed from the superfusion columns and extracted in 1.0 ml of 0.1N HCl. To superfusion fractions and extracts 12 ml Liquiscint counting fluid (NEN) was then added and samples were counted in a Packard Tricarb Liquid Scintillation Counter. No corrections were made for quenching.

The ratio of S2/S1 (as compared to controls where no drug was present during S2) was a measure of the ability of the drug to enhance or depress stimulus-induced acetylcholine release. The invitro ACh release data was summarized in Table X.

TABLE X

| % INCREASE OF STIMILIS-INDUCED ACh RELEASE IN RAT CEREBRAL CORTEX IN VITRO | | | |
|---|---|---|---|
| Example | $10^{-6}$ | $10^{-5}$ | $10^{-4}$ (M) |
| 1 | — | — | +349* |
| 2 | +11 | +61* | +265* |
| 3 | +06 | +88* | +238* |
| 4 | +94* | +457* | +433* |
| 5 | +14 | +78* | +355* |
| 6 | +195* | +313* | — |
| 7 | — | 0 | +30* |
| 8 | — | +37* | +429* |
| 9 | 0 | +54* | +275* |
| 12 | — | +11 | +48* |
| 13 | 0 | +13 | +100* |
| 16 | +01 | +47* | — |
| 19 | +34* | +323* | — |
| 43 | +34* | +210* | — |
| 45 | — | +12 | +97* |
| 46 | +20 | +218* | — |
| 49 | +16* | +49* | — |
| 61 | +13 | +87 | — |
| 62 | +3 | +111 | — |
| 63 | +105 | +338 | — |
| 64 | +4 | +55 | — |
| 65 | +3 | +94 | — |
| 124 | +0 | +148 | — |
| 125 | +17 | +50 | — |
| 182 | +19 | +302 | — |
| 183 | — | +471 | +607 |
| 240 | +0 | +0 | — |
| 288 | +37 | +215 | — |
| 324 | +35 | +217 | — |
| 387 | — | +14 | — |
| 440 | +695 | +501 | — |
| 441 | +695 | +501 | — |
| 442 | +222 | +340 | — |
| 443 | +345 | +221 | — |
| 444 | +228 | +467 | — |
| 445 | +71 | +233 | — |
| 446 | +470 | +465 | — |
| 447 | +288 | +259 | — |
| 448 | +513 | +429 | — |
| 449 | +387 | — | — |
| 450 | +359 | +308 | — |
| 451 | +351 | — | — |
| 452 | +439 | — | — |
| 453 | +45 | +261 | — |
| 454 | +264 | +375 | — |
| 455 | +167 | +460 | — |
| 456 | +125 | +429 | — |
| 457 | +0 | +69 | — |
| 458 | +410 | — | — |
| 459 | +207 | +335 | — |
| 460 | +35 | +138 | — |
| 461 | +145 | +303 | — |
| 462 | +310 | — | — |
| 463 | +254 | +299 | — |
| 464 | +76 | +238 | — |
| 532 | +57 | +359 | — |
| 611 | +222 | +227 | — |
| 608 | +22 | +185 | — |
| 624 | +0 | +90 | — |

*Significantly different from control P < 0.05, student's t-test.

Using similar test procedures, the compounds of Examples 2 and 4 were also found to enhance the release of acetylcholine from hippocampal slices and that of acetylcholine and dopamine from caudate nucleus slices in vitro. The compound of Example 4, in addition, was found to also enhance the release of serotonin from cortical slices.

Behavioral Test Procedure

The effect of compounds on rat active avoidance (pole-climb) performance was studied as follows: Male Sprague-Dawley rats (Charles River), weighing 150–200 grams, received two blocks of five learning trials daily (1 AM, 1 PM), for four days. A trial consisted of placing a rat in a cage (Coulbourn Model E10-10, equipped with a removable shock gridfloor), facing a pole (wood, with parallel diagonal notches, mounted from the ceiling). The trial was started by closing the cage door and switching on the cage light. After 10 seconds, shock was applied through the gridfloor for 10 seconds by a Coulbourn Model E13-08 shocker. Footshock intensity ranged from 0.6 to 1.2 mA. At the end of the trial, the light and shock were turned off and the rat was removed from the cage. If the rat jumped on the pole prior to the onset of shock, it was considered to have avoided; if it jumped after the shock, it was considered to have escaped. Groups of 6 to 9 rats were subcutaneously treated with various doses of a compound or the corresponding vehicle 30 minutes prior to the first training trial of each block.

Active avoidance performance data were analyzed by regression analysis (see Snedecor and Cochran, *Statistical Methods*, 6th Edition, page 432) of the cumulative number of avoidances versus blocks of trials curve. The mean slope and SEM (Standard Error of the Mean) of this curve were calculated for each treatment group and taken as a measure of active avoidance performance. Drug effects were expressed as percent change in slope compared to the slope of the control curve. The results are summarized in Table XI.

TABLE XI

% ENHANCEMENT OF ACTIVE AVOIDANCE PERFORMANCE IN RATS

| Example | Drug Dose (mg/kg s.c.) | | | | | | |
|---|---|---|---|---|---|---|---|
| | 0.1 | 0.3 | 1 | 3 | 5 | 10 | 20 |
| 2 | — | — | — | — | 54* | 53* | 21 |
| 4 | +59* | +91* | +84* | +57 | — | — | — |

*Significantly different from control, P < 0.05, student's t-test.

Utility

The foregoing test results suggest that compounds of this invention have utility in the treatment of cognitive deficiencies and/or neurological function deficits and/or mood and mental disturbances, in patients suffering from nervous system disorders like Alzheimer's disease, Parkinson's disease, senile-dementia, multi-infarct dementia, Huntington's disease, mental retardation, Myasthenia Gravis etc. Compounds of this invention can be administered to treat said deficiencies by any means that produces contact of the active agent with the agent's site of action in the body of a mammal. The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. For use in the treatment of said diseases, a daily oral dosage of active ingredient can be about 0.001 to 100 mg/kg of body weight. Ordinarily a dose of 0.01 to 10 mg/kg per day in divided doses one to four times a day or in sustained release form effective to obtain the desired results.

Dosage forms (compositions) suitable for administration contain from about 1 milligram to about 100 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tables and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solution and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or asorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil was prepared and injected by means of a positive displacement pumpinto gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

What is claimed is:

1. A process for preparing a compound of formula:

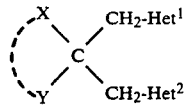

or a salt thereof, wherein:

X and Y are taken together to form a saturated or unsaturated carbocyclic or heterocyclic first ring and the shown carbon in said ring is α to at least one additional aromatic ring or heteroaromatic ring fused to the first ring, the total number of carbocyclic fused rings being 3-5, the sole heterocyclic substituents on said fused rings being Het[1] and Het[2];

one of Het[1] or Het[2] is 2, 3, or 4-pyridyl or 2, 4, or 5-pyrimidinyl and the other is selected from:
(a) 2, 3, or 4-pyridyl
(b) 2, 4, or 5-pyrimidinyl,
(c) 2-pyrazinyl,
(d) 3 or 4-pyridazinyl,
(e) 3 or 4-pyrazolyl, (f) 2 or 3-tetrahydrofuranyl, and
(g) 3-thienyl;
which comprises:
(a) contacting a compound of the formula

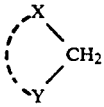

with a suitable base in an aprotic solvent, said base selected from sodamide, lithium diisopropylamide, sodium hydride, sodium alkoxide, potassium alkoxide, lithium alkoxide, potassium hydride, lithium 2,2,6,6-tetramethylpiper-idide, butyl lithium, and lithium, sodium or potassium hexamethyldisilazide;
(b) contacting the anion product from step (a) with a compound of the formula $$DCH_2-Het^1$$

wherein D is halogen, methanesulfonate, or p-toluenesulfonate;
(c) contacting the product from step (b) with a base selected from the group recited in step (a); and
(d) contacting the product from step (c) with a compound of the formula $$DCH_2-Het^2$$

wherein D is halogen, methanesulfonate, or p-toluenesulfonate.

* * * * *